US011951261B2

(12) United States Patent
Tamiya et al.

(10) Patent No.: US 11,951,261 B2
(45) Date of Patent: Apr. 9, 2024

(54) NITRIC OXIDE ADMINISTRATION DEVICE

(71) Applicant: Teijin Pharma Limited, Tokyo (JP)

(72) Inventors: Rei Tamiya, Tokyo (JP); Naoyuki Iida, Tokyo (JP); Shosaku Motohara, Tokyo (JP); Jun Matsui, Matsuyama (JP)

(73) Assignee: Teijin Pharma Limited, Tokyo (JP)

(*) Notice: Subject to any disclaimer, the term of this patent is extended or adjusted under 35 U.S.C. 154(b) by 540 days.

(21) Appl. No.: 17/287,346

(22) PCT Filed: Sep. 25, 2019

(86) PCT No.: PCT/JP2019/037661
§ 371 (c)(1),
(2) Date: Apr. 21, 2021

(87) PCT Pub. No.: WO2020/084992
PCT Pub. Date: Apr. 30, 2020

(65) Prior Publication Data
US 2021/0379320 A1 Dec. 9, 2021

(30) Foreign Application Priority Data
Oct. 25, 2018 (JP) .................. 2018-201147

(51) Int. Cl.
*A61M 16/12* (2006.01)
*A61M 16/00* (2006.01)
(Continued)

(52) U.S. Cl.
CPC .......... *A61M 16/12* (2013.01); *A61M 16/101* (2014.02); *A61M 16/20* (2013.01);
(Continued)

(58) Field of Classification Search
CPC .............. A61M 16/00; A61M 16/0063; A61M 16/0816; A61M 16/10; A61M 16/1005;
(Continued)

(56) References Cited

U.S. PATENT DOCUMENTS

| 2006/0180147 A1* | 8/2006 | Rounbehler ........ A61M 16/122 128/203.12 |
| 2010/0242734 A1 | 9/2010 | Maeda et al. |
| 2013/0177657 A1* | 7/2013 | Hilbig .................... A61K 33/00 422/120 |

FOREIGN PATENT DOCUMENTS

| EP | 3 871 726 A1 | 9/2021 |
| JP | 7-505073 A | 6/1995 |

(Continued)

OTHER PUBLICATIONS

International Search Report for PCT/JP2019/037661, dated Dec. 17, 2019 (PCT/ISA/210).

*Primary Examiner* — Joseph D. Boecker
(74) *Attorney, Agent, or Firm* — Sughrue Mion, PLLC

(57) ABSTRACT

A nitric oxide administration device 1 includes a first flow path 101 including a first intake port 101*a* and an oxygen supply port 101*b*, an oxygen generation unit 100 which is arranged in the first flow path 101 and which generates concentrated oxygen from air introduced via the first intake port 101*a*, the generated concentrated oxygen being supplied via the oxygen supply port 101*b*, a second flow path 201 which is branched from the first flow path 101 and which includes an NO supply port 201*b*, and an NO generation unit 200 which is arranged in the second flow path 201 and which generates NO from gas distributed from the first flow path 101, the generated NO being supplied via the NO supply port 201*b*.

11 Claims, 29 Drawing Sheets

(51) Int. Cl.
*A61M 16/10* (2006.01)
*A61M 16/20* (2006.01)
*C01B 21/20* (2006.01)

(52) U.S. Cl.
CPC ....... *C01B 21/203* (2013.01); *A61M 16/0063* (2014.02); *A61M 16/202* (2014.02); *A61M 2202/0208* (2013.01); *A61M 2202/0275* (2013.01)

(58) Field of Classification Search
CPC .. A61M 16/101; A61M 16/12; A61M 16/202; A61M 2202/0208; A61M 2202/0275; C01B 21/203
See application file for complete search history.

(56) References Cited

FOREIGN PATENT DOCUMENTS

| | | |
|---|---|---|
| JP | 2013-543430 A | 12/2013 |
| JP | 2016-516488 A | 6/2016 |
| JP | 2017-531539 A | 10/2017 |
| WO | 93/17741 A1 | 9/1993 |
| WO | 2009/063938 A1 | 5/2009 |
| WO | 2012/038860 A1 | 3/2012 |
| WO | 2014/143842 A1 | 9/2014 |
| WO | 2016/064863 A1 | 4/2016 |

\* cited by examiner

NITRIC OXIDE ADMINISTRATION DEVICE

CROSS REFERENCE TO RELATED APPLICATIONS

This application is a National Stage of International Application No. PCT/JP2019/037661, filed Sep. 25, 2019, claiming priority based on Japanese Patent Application No. 2018-201147, filed Oct. 25, 2018.

FIELD

The present invention relates to a nitric oxide administration device (NO administration device).

BACKGROUND

Pulmonary hypertension is a disease in which the blood pressure (pulmonary artery pressure) of the pulmonary artery, which is a blood vessel from the heart to the lungs, increases. Pulmonary hypertension is classified into groups 1 to 5 in the Nice Classification [2013]. Group 3 pulmonary hypertension is associated with pulmonary disease and hypoxemia. Long term oxygen therapy (LTOT) is one of the treatments for pulmonary hypertension. When long term oxygen therapy is given to a patient with pulmonary hypertension, the effect of partially suppressing the progression of pulmonary hypertension is shown due to the vasodilatory effect of relieving vascular spasms, but normalization of pulmonary arterial pressure cannot be expected. Conversely, nitric oxide (NO) is a vasodilator and can selectively dilate blood vessels around the ventilated alveoli. Thus, in hospitals, NO inhalation therapy using NO supplied from a cylinder is widespread in the perioperative period and in newborns.

Currently, NO inhalation therapy at home is not widespread because NO gas cylinders for medical use are expensive and NO handling is difficult. It is known that NO can stably be generated from oxygen and nitrogen present in air by discharge (such as corona discharge)(Patent Literature 1). Furthermore, as NO inhalation therapy, a nitric oxide administration device using electric discharge is known (Patent Literature 2). It has been reported that the inhalation of NO and the inhalation of concentrated oxygen in combination are effective for patients with group 3 pulmonary hypertension. Thus, there is an increasing need for nitric oxide administration devices for home use, and nitric oxide administration devices which can also administer concentrated oxygen.

For example, in the nitric oxide administration device described in Patent Literature 2, an oxygen concentrator, an oxygen generator, or an oxygen cylinder is arranged upstream of the nitric oxide administration device as an oxygen supply source.

CITATION LIST

Patent Literature

[PTL 1] Japanese Unexamined PCT Publication (Kohyo) No. H07-505073
[PTL 2] Japanese Unexamined PCT Publication (Kohyo) No. 2016-516488

SUMMARY

Technical Problem

NO is an unstable substance which reacts with oxygen at room temperature to generate nitrogen dioxide ($NO_2$). This reaction is more likely to proceed as the concentrations of NO and oxygen increase and the temperature decreases. $NO_2$ is also generated by reacting generated NO with unreacted oxygen during discharge before inhalation by a patient. Further, $NO_2$ is also generated during the reaction of generating NO by electric discharge. $NO_2$ is highly toxic, and the $NO_2$ generated in this manner is inhaled by the patient, albeit in small quantities. Even if the generated NO and $NO_2$ are not inhaled by the patient, they are exhausted into the surroundings, whereby the NO concentration and $NO_2$ concentration in the surroundings increase, which may cause harm to the human body.

In the nitric oxide administration device described in Patent Literature 2, since the oxygen supply source is arranged upstream, the oxygen concentration of gas flowing inside is higher than that of air. Thus, there is a risk that $NO_2$ is generated before inhalation the patient.

The present invention aims to provide a nitric oxide administration device which is configured so as to suppress the generation of $NO_2$.

Solution to Problem

According to an aspect of the present invention, there is provided a nitric oxide administration device comprising a first flow path including a first intake port and an oxygen supply port, an oxygen generation unit which is arranged in the first flow path and which generates concentrated oxygen from air introduced via the first intake port, the generated concentrated oxygen being supplied via the oxygen supply port, a second flow path which is branched from the first flow path and which includes an NO supply port, and an NO generation unit which is arranged in the second flow path and which generates NO from gas distributed from the first flow path, the generated NO being supplied via the NO supply port.

The oxygen generation unit and the NO generation unit may be housed in an interior of the same housing. There may further be provided a compressor arranged in the first flow path. The distributed gas may be air compressed by the compressor. The distributed gas may be hypoxic gas generated along with the generation of concentrated oxygen in the oxygen generation unit. The distributed gas may be concentrated oxygen generated by the oxygen generation unit. In the second flow path, hypoxic gas generated along with the generation of concentrated oxygen in the oxygen generation unit may be mixed with generated NO. A flow path switching valve for switching opening and closing of the flow path of the hypoxic gas from the first flow path to the second flow path may be arranged. An NO or $NO_2$ removal agent may be arranged upstream of the first flow path or in the vicinity of the first intake port. There may further be provided a cannula which is connected to the oxygen supply port and the NO supply port and which has an independent flow path. The NO generation unit may have a second intake port.

Advantageous Effects of Invention

According to the present invention, the common effect of providing a nitric oxide administration device which is configured so as to suppress the generation of $NO_2$ is exhibited.

DESCRIPTION OF EMBODIMENTS

Figure 1:
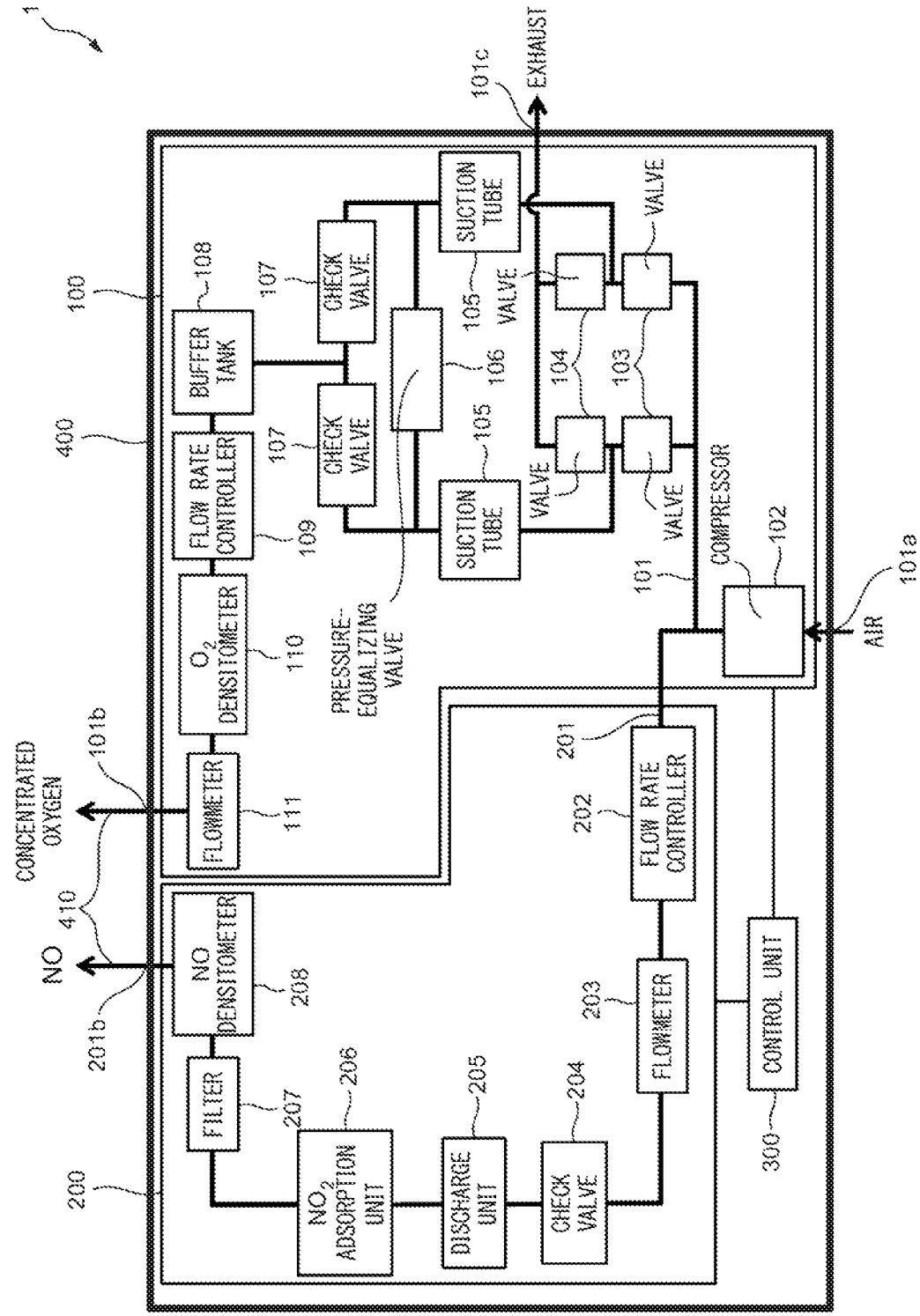
FIG. 1 is a schematic view of a nitric oxide administration device.

The embodiments of the present invention will be described in detail below while referring to the drawings. In the drawings, corresponding constituent elements have been assigned common reference signs.

FIG. 1 is a schematic view of a nitric oxide administration device 1. The nitric oxide administration device 1 comprises a first flow path 101 including an intake port 101a and an oxygen supply port 101b, an oxygen generation unit 100 which is arranged in the first flow path 101 and which generates concentrated oxygen from air introduced via the intake port 101a, a second flow path 201 which is branched from the first flow path 101 and which includes an NO supply port 201b, an NO generation unit 200 which is arranged in the second flow path 201 and which generates NO from gas distributed from the first flow path 101, a control unit 3W), and a housing 400. The oxygen generation unit 100, the NO generation unit 200, and the control unit 300 are housed in the interior of the same housing 400. The concentrated oxygen generated by the oxygen generation unit 100 is supplied via the oxygen supply port 101b and a cannula 410. The NO generated by the NO generation unit 200 is supplied via the NO supply port 201b and the cannula 410. The various operations of the oxygen generation unit 100 and the NO generation unit 200 are controlled by the control unit 300. The nitric oxide administration device 1 is connected to a power source via an unillustrated power cable.

In general, oxygen concentrators are devices which enable oxygen in air to be separated from nitrogen and concentrated. Examples of configurations of oxygen concentrators include oxygen-enriched membranes which separate oxygen and nitrogen in air using a separation membrane which allows more oxygen to permeate than nitrogen, and PSA-type devices which separate oxygen and nitrogen in air by filling one or more adsorption beds with an adsorbent capable of selectively adsorbing nitrogen and repeating pressurization and depressurization (for example, Japanese Unexamined Patent Publication (Kokai) No. 2008-238076). The oxygen generation unit 100 is configured to generate concentrated oxygen by the PSA method. However, concentrated oxygen may be generated by an oxygen-enriched membrane method or another method. Furthermore, oxygen may be directly supplied from an oxygen cylinder via a flow path different from the second flow path 201.

The oxygen generation unit 100 comprises a compressor 102 as an air compressor, a gas flow path switching unit composed of a pressure valve 103 and a pressure-reducing valve 104 arranged downstream of the compressor 102, and a suction tube 105 arranged downstream of the gas flow path switching unit. The suction tube 105 houses an adsorbent which preferentially adsorbs nitrogen over oxygen. The gas flow path switching unit selectively switches the flow path between the suction tube 105 and an exhaust port 101c. Downstream of the compressor 102, the first flow path 101 is branched into two, and the oxygen generation unit 100 has two sets of gas flow path switching units and suction tubes 105. The oxygen generation unit 100 may comprise three or more sets of gas flow path switching units and suction tubes 105. The oxygen generation unit 100 comprises, downstream of the two suction tubes 105, a pressure-equalizing valve 106 which connects the branched first flow paths 101, check valves 107 which are arranged downstream of the pressure-equalizing valve 106 and downstream of the respective two suction tubes 105, a buffer tank 108 arranged in the first flow path 101 which is merged downstream of the check valves 107, a flow rate controller 109 arranged downstream of the buffer tank 108, an $O_2$ densitometer 110 arranged downstream of the flow rate controller 109, and a flowmeter 111 arranged downstream of the $O_2$ densitometer 110.

The concentrated oxygen generation process by the oxygen generation unit 100 will be described.

Air introduced via the intake port 101a is compressed by the compressor 102. The air compressed by the compressor 102 (pressurized air) is supplied to one suction tube 105 by a gas flow path switching unit. Specifically, a pressure valve 103 corresponding to one suction tube 105 is opened, and the pressure-reducing valve 104 is closed. When the interior of the suction tube 105 is pressurized by the compressed air, the nitrogen in the supplied compressed air is adsorbed in the suction tube 105. This is referred to as an adsorption process. Oxygen in the compressed air flows out from the suction tube 105 to the downstream without being adsorbed in the suction tube 105, and is stored in the buffer tank 108 via the check valve 107.

At this time, since the pressure valve 103 corresponding to the other suction tube 105 is closed and the pressure-reducing valve 104 is open, the upstream side of the other suction tube 105 is open to the atmosphere through the exhaust port 101c, whereby the interior of the suction tube 105 is depressurized. Since the adsorbent has a property of releasing adsorbed nitrogen when the gas pressure decreases, the nitrogen released from the adsorbent is exhausted through the exhaust port 101c. This is referred to as a desorption process.

Next, the pressure-equalizing valve 106 is opened while maintaining the states of the two pressure valves 103 and the two pressure-reducing valves 104. As a result, oxygen flowing downstream from one suction tube 105 in the adsorption process is refluxed to the other suction tube 105 in the desorption process via the pressure-equalizing valve 106. By refluxing the concentrated oxygen, the partial pressure of nitrogen inside the other suction tube 105 is reduced, whereby the release of nitrogen from the adsorbent is promoted.

The oxygen generation unit 100 repeatedly switches the adsorption process and the desorption process between the two suction tubes 105 by the gas flow path switching unit, whereby concentrated oxygen can be obtained from air. The concentrated oxygen stored in the buffer tank 108 is supplied via the oxygen supply port 101b while the flow rate is controlled by the flow rate controller 109 based on the values of the 02 densitometer 110 and the flowmeter 111.

The NO generation unit 200 comprises, in the second flow path 201 branched from the first flow path 101 downstream of the compressor 102, a flow rate controller 202, a flowmeter 203 arranged downstream of the flow rate controller 202, a check valve 204 arranged downstream of the flowmeter 203, a discharge unit 205 arranged downstream of the check valve 204, an $NO_2$ adsorption unit 206 arranged downstream of the discharge unit 205, a filter 207 arranged downstream of the $NO_2$ adsorption unit 206, and an NO densitometer 208 arranged downstream of the filter 207.

A part of the air compressed by the compressor 102 is distributed from the first flow path 101 to the second flow path 201. The gas as distributed compressed air is supplied to the discharge unit 205 via the check valve 204 while the flow rate thereof is controlled by the flow rate controller 202 based on the value of the flowmeter 203. In the oxygen generation unit 100, the generation of concentrated oxygen according to the PSA method described above is accompanied by pressure fluctuations. Thus, the gas distributed from the first flow path 101 to the second flow path 201 is also influenced by the pressure fluctuations, but the pressure fluctuations in the second flow path 201 are suppressed by the flow rate controller 202.

Although not illustrated, the discharge unit 205 comprises a high voltage generation source and at least one electrode pair. The discharge unit 205 can generated NO from oxygen ($O_2$) and nitrogen ($N_2$) present in the gas flowing through the second flow path 201 by generating a discharge (such as corona discharge) between the electrode pair by a high voltage generation source. The method for generating NO is known as described in, for example, Japanese Unexamined Patent Publication (Kokai) No. 2004-167284 and Japanese Unexamined PCT Publication (Kohyo) No. 2017-531539. As the high voltage generation source, a transformer using the principle of an induction coil such as an ignition coil may be used, or a Cockcroft-Walton circuit may be used.

The generated NO reacts with oxygen in the gas to generate highly toxic $NO_2$. Furthermore, $NO_2$ is also generated during the reaction of generating NO by electric discharge. Thus, downstream of the discharge unit 205, $NO_2$ is adsorbed and removed by the $NO_2$ adsorption unit 206, which is an $NO_2$ removal unit. The $NO_2$ adsorption unit 206 contains, for example, soda lime (primarily calcium hydroxide), activated carbon, or zeolite. The $NO_2$ removal unit may be configured to remove $NO_2$ in the gas by another means other than adsorption.

The filter 207 arranged downstream of the $NO_2$ adsorption unit 206 is, for example, a HEPA (High-Efficiency Particulate Air Filter) filter. The filter 207 removes contaminants and dust in the gas. Examples of the contaminants and dust in the gas include fine particles of worn electrodes which are unintentionally released from the discharge unit 205 and powders such as soda lime which are unintentionally released from the $NO_2$ adsorption unit 206.

The NO densitometer 208 measures the NO concentration most downstream of the second flow path 201 in order to determine whether or not the NO concentration has no problem related to administration to the patient. The measurement result is collected in the control unit 300 and fed back to, for example, the flow rate controller 202 and the discharge unit 205. Specifically, control signals are transmitted from the control unit 300 to the flow rate controller 202 and the discharge unit 205, and the NO generation amount or concentration is adjusted.

The control unit 30) has one or more processors and peripheral circuits therefor, and controls the overall operation of the nitric oxide administration device 1 in an integrated manner. The control unit 300 performs processing based on a computer program stored in advance in a storage unit (not illustrated). During processing, the control unit 30 receives signals from various sensors such as the $O_2$ densitometer 110, the flowmeter 111, and the NO densitometer 208, and transmits the control signals to the compressor 102, the pressure valve 103, and the discharge unit 205. The control unit 30) may have an input/output unit, for example, a display unit such as a display, or an input interface such as operation buttons or a touch panel.

It has been reported that the combined use of NO inhalation and concentrated oxygen inhalation is effective for patients with group 3 pulmonary hypertension. According to the nitric oxide administration device 1, concentrated oxygen generated in the first flow path 101 by the oxygen generation unit 100 can be administered to the patient via the oxygen supply port 101b, and NO generated in the second flow path 201 by the NO generation unit 200 can be administrated to the patient via the NO supply port 201b. Specifically, patient administration can be performed using a cannula 410 which is connected to the oxygen supply port 101b and the NO supply port 201b and which has an independent flow path. Thus, NO and concentrated oxygen are mixed before being administered to the patient, whereby the generation of $NO_2$ due to the reaction between NO and concentrated oxygen is suppressed. The cannula 410 may be configured so that concentrated oxygen and NO are mixed and administered immediately before inhalation by the patient.

Since the oxygen generation unit 100 and the NO generation unit 20 are housed inside the housing 400, the control unit 300 and the power supply can be shared, whereby a single system which is small, lightweight, and saves power can be achieved. Further, in the nitric oxide administration device 1, since the oxygen generation unit 100 and the NO generation unit 200 share the compressor 102, the pressurized gas necessary for each generation can be supplied simultaneously.

The operation of nitric oxide administration device 1 shown in FIG. 1 is not linked to the respiration of the patient. In other words, the nitric oxide administration device 1 operates in a continuous flow mode in which NO is continuously supplied in the operating state. However, the nitric oxide administration device 1 can also be configured to operate in a synchronized flow mode which synchronizes the operation of the nitric oxide administration device 1 with the respiration of the patient. In this case, for example, as in the nitric oxide administration device 2 shown in FIG. 2, a micro-differential pressure sensor 209 is arranged downstream of the NO densitometer 208. By detecting the negative pressure due to the respiration of the patient with the micro-differential pressure sensor 209 and controlling the discharge unit 205 in synchronization therewith, the generation or stoppage of NO generate can be controlled and the administration or stoppage of NO can be controlled. Specifically, NO is supplied when the patient inhales, and NO is stopped when the patient exhales.

When the synchronized flow mode is used, the respiration of the patient may be detected with a respiration detection unit other than the micro-differential pressure sensor. Examples of other respiration detection units include oral and nasal thermistors provided in the mouth and nose of the patient to measure temperature changes due to airflow during respiration, and thoracoabdominal bands for detecting changes in chest circumference and abdominal circumference of the patient. The respiration detection unit may be applied to other nitric oxide administration devices described herein. Furthermore, NO administration or stoppage may be controlled by further arranging a shutoff valve between the filter 207 and the NO densitometer 208. By arranging a shutoff valve, the pressure inside the second flow path 201 upstream of the shutoff valve can be maintained higher. Due to the pressure difference between upstream and downstream when the shutoff valve is closed, the flow rate immediately after restarting of NO supply can be increased during NO inhalation of the patient, and administration can be completed in a relatively short time. Specifically, administration can be properly completed within the valid time of inhalation.

In the nitric oxide administration device 1, single or separated NO/$NO_2$ densitometers, which are capable of measuring NO and $NO_2$ concentrations, may be arranged in place of the NO densitometer 208. As a result, highly toxic $NO_2$ can also be measured. Furthermore, an NO measurement unit for measuring the concentration or substance amount of NO may be arranged in place of the NO densitometer 208. Furthermore, the $NO_2$ densitometer may be an $NO_2$ measurement unit which measures the concentration or substance amount of $NO_2$. Furthermore, a pressure gauge may be arranged in place of or in addition to the flowmeter 203. By monitoring the pressure of the second flow path 201 using the pressure gauge, the operating state of the nitric oxide administration device 1, for example, the presence or absence of abnormalities in the flow path, can be understood. Furthermore, the pressure-reducing valve may be arranged at the second flow path 201 upstream of the flow rate controller 202. By arranging the pressure-reducing valve, the gas compressed by the compressor 102 can be adjusted to the optimum pressure for NO generation and supply. Further, a buffer tank may be arranged in the second flow path 201 upstream of the flow rate controller 202. By arranging a buffer tank, pressure fluctuations accompanying the generation of concentrated oxygen according to the PSA method described above can be suppressed.

Figure 3:
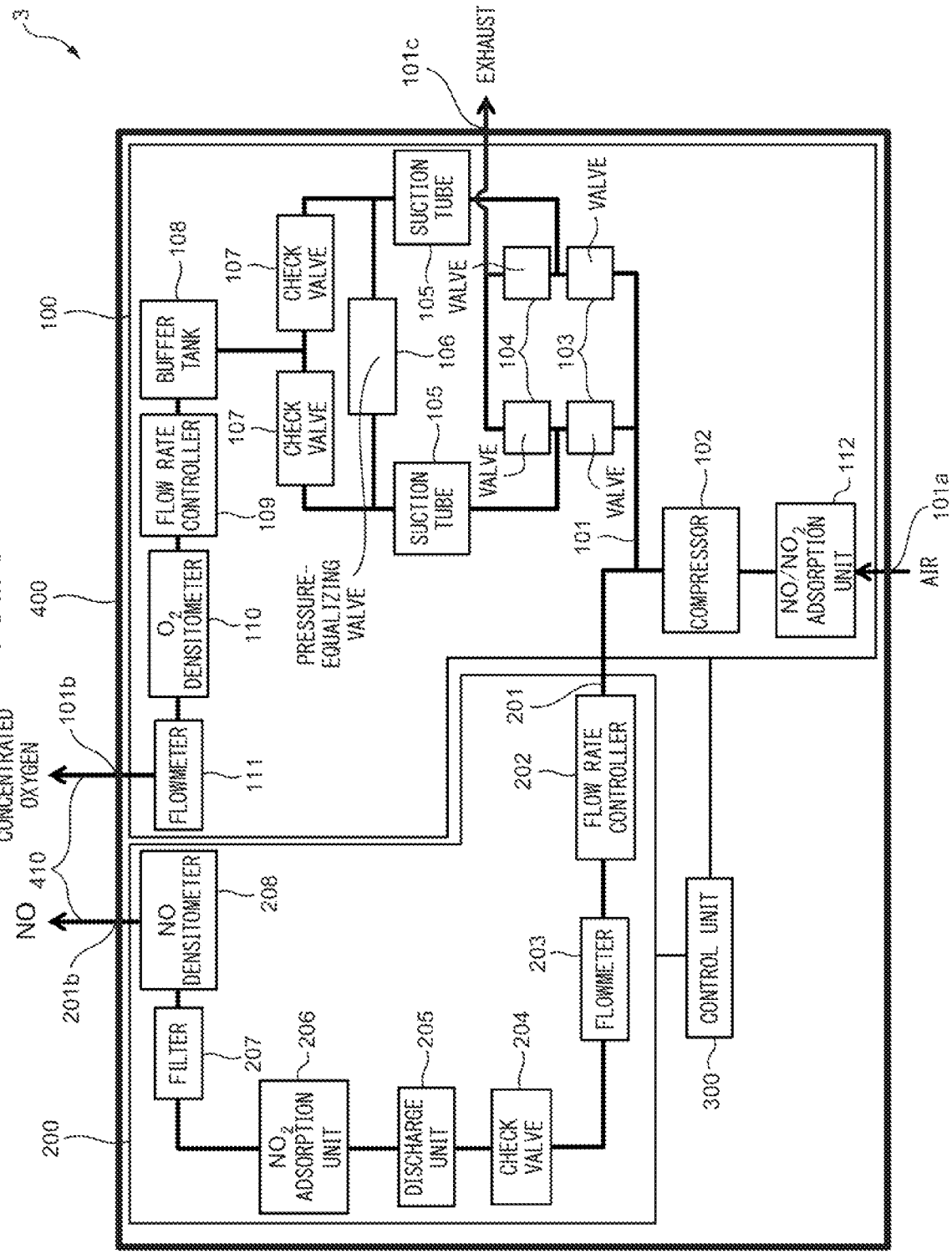
FIG. 3 is a schematic view of yet another nitric oxide administration device.

In particular in continuous flow mode, the gas containing NO which was not inhaled by the patient is released from the cannula 410 into the surroundings. The released NO reacts with oxygen in the air to generate highly toxic $NO_2$. In the nitric oxide administration device 3 as shown in FIG. 3, an NO/$NO_2$ adsorption unit 112 which is capable of adsorbing either or both of NO and $NO_2$, i.e., an NO/$NO_2$ removal unit, may be arranged in the first flow path 101 upstream of the compressor 102. The NO/$NO_2$ removal unit can have, for example, a configuration in which the soda lime (mainly calcium hydroxide), activated carbon, or zeolite described above and a powder filter are combined. Since NO and $NO_2$ contained in the air introduced into the nitric oxide administration device 3 via the intake port 101$a$ are removed by the NO/$NO_2$ adsorption unit 112, the concentration of NO and the concentration of $NO_2$ in the surroundings can be reduced.

Figure 4:
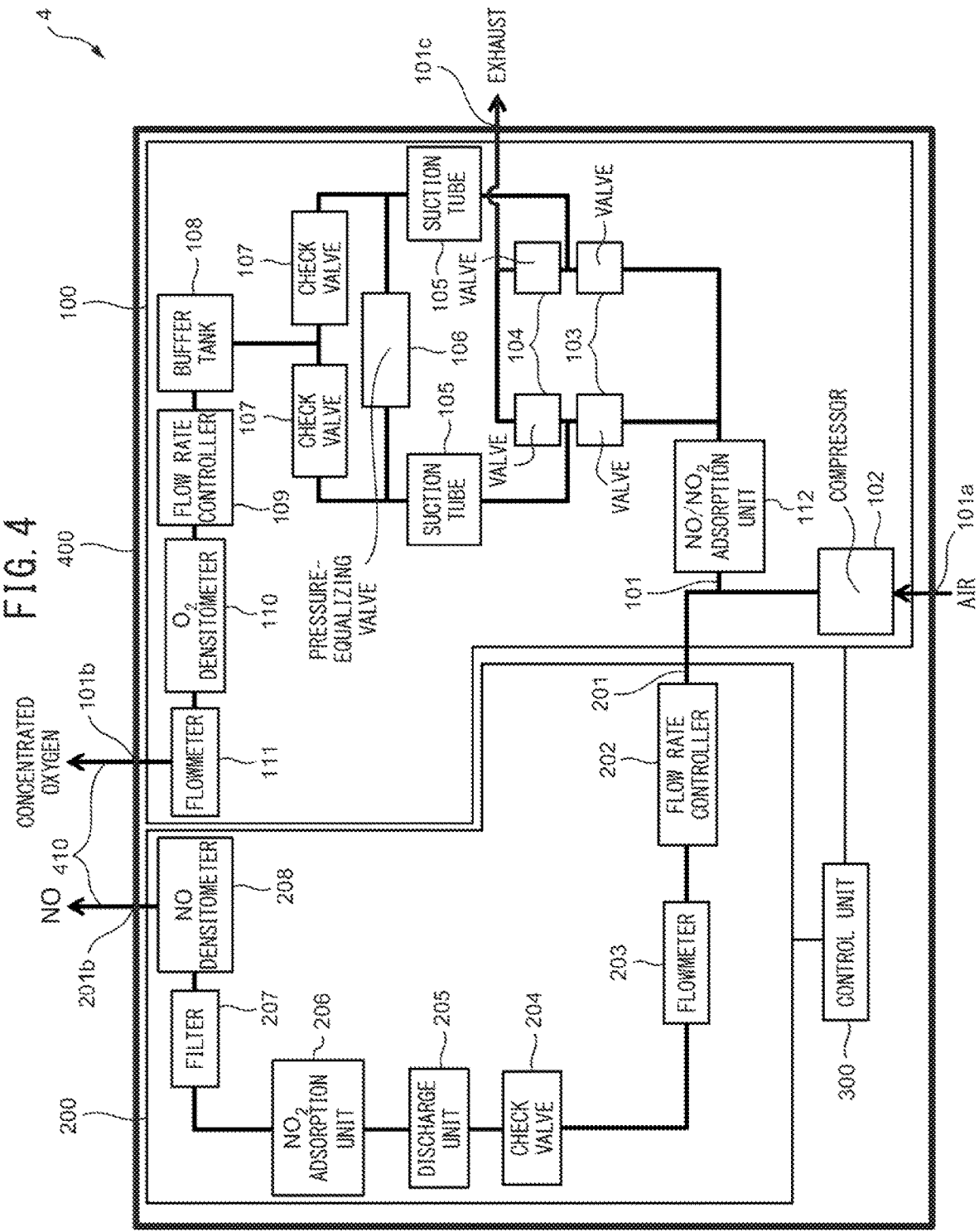
FIG. 4 is a schematic view of yet another nitric oxide administration device.

The NO/$NO_2$ adsorption unit 112 may be arranged in the first flow path 101 downstream of the compressor 102, as in the nitric oxide administration device 4 shown in FIG. 4, rather than in the first flow path 101 upstream of the compressor 102. Since the NO generation unit 200 comprises the $NO_2$ adsorption unit 206, by arranging the NO/$NO_2$ adsorption unit 112 in the oxygen generation unit 100, functional redundancy can be prevented. In short, the NO or $NO_2$ removal agent is arranged upstream of the first flow path 101 or in the vicinity of the intake port 101$a$. The NO/$NO_2$ adsorption unit 112 may be used in other oxygen generation units 100 described herein.

Describing the NO or $NO_2$ removal agent in more detail, the amount of NO administered to the patient is much smaller than the amount of concentrated oxygen administered to the patient. Furthermore, due to the characteristics of the concentrated oxygen and NO generation processes, the amount of air used to generate the amount of concentrated oxygen required for treatment is significantly higher than the amount of air used to generate the amount of NO required for treatment. Thus, by arranging the NO or $NO_2$ removal agent in the vicinity of the flow path through which the air for generating concentrated oxygen passes. i.e., upstream of the first flow path 101 or in the vicinity of the intake port 101$a$, NO and $NO_2$ can be removed efficiently.

The nitric oxide administration device 4 may further comprise an oxidizing means for oxidizing NO to $NO_2$ or a reducing means for reducing $NO_2$ to NO. By providing the nitric oxide administration device 4 with an oxidizing means or a reducing means, adsorption in the NO/$NO_2$ adsorption unit 112 can be further promoted. As the oxidizing means, gas containing oxygen having a higher concentration than in air may be used, or gas containing ozone having a higher concentration than in air may be used. Thus, the nitric oxide administration device 4 may further comprise an ozone generation means. Furthermore, as the reducing means, a heating device or an ultraviolet ray generator may be used. The oxidizing means and the reducing means may be used in other nitric oxide administration devices described herein.

Figure 5:
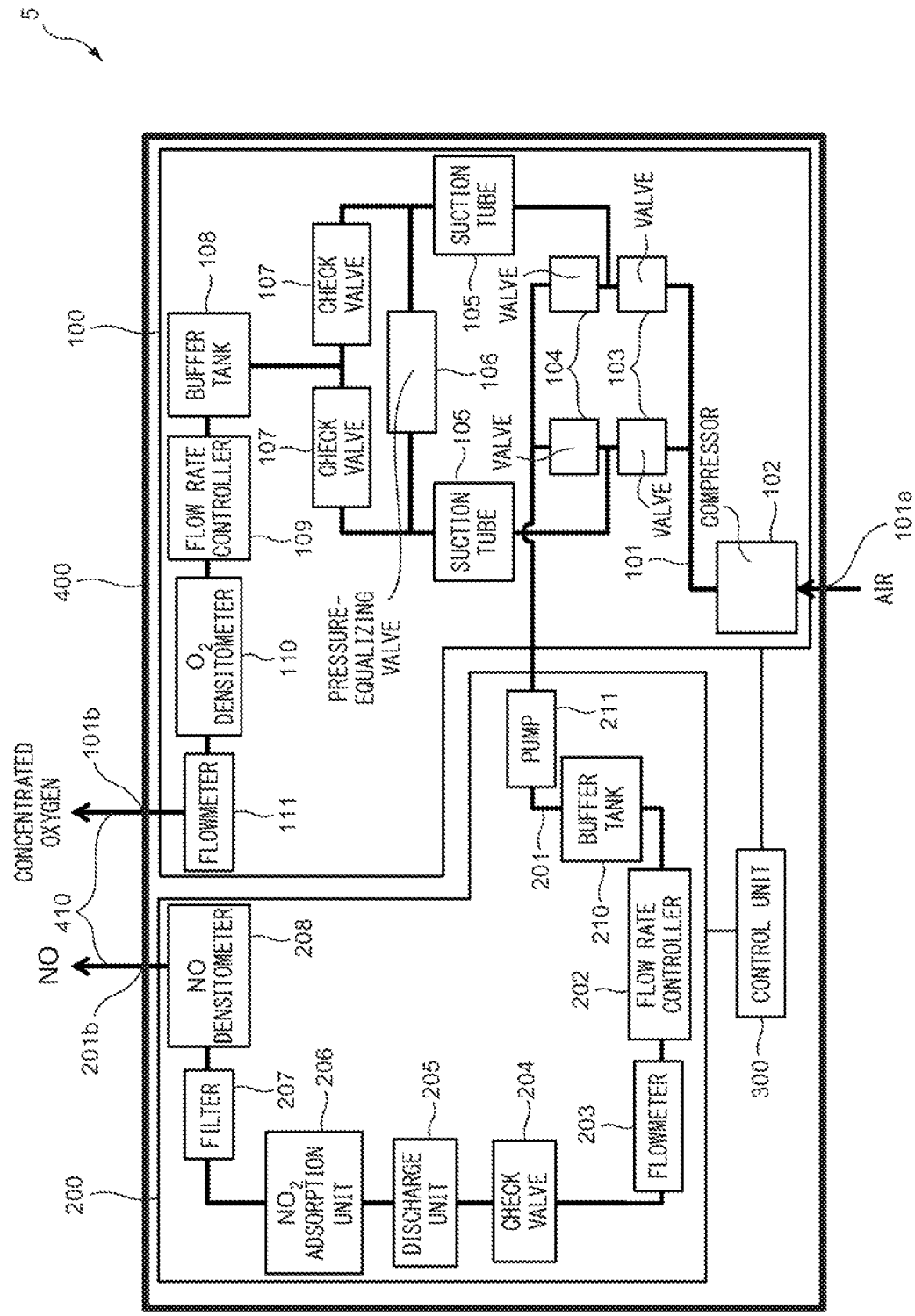
FIG. 5 is a schematic view of yet another nitric oxide administration device.

FIG. 5 is a schematic view of yet another nitric oxide administration device 5. For example, in the nitric oxide administration device 1 shown in FIG. 1, the second flow path 201 is branched from the first flow path 101 between the compressor 102 and the gas flow path switching unit. In the nitric oxide administration device 5 shown in FIG. 5, the second flow path 201 is branched from the first flow path 101 downstream of the pressure-reducing valve 104 of the gas flow path switching unit. Thus, in the desorption process in the oxygen generation unit 100, the gas (hypoxic gas) containing a large amount of nitrogen released from the adsorbent in the suction tube 105 is distributed from the first flow path 101 to the second flow path 201. Thus, since the oxygen concentration of the gas in the second flow path 201 becomes overall low, even if NO is generated by the discharge unit 205, the generation of $NO_2$ due to the reaction between NO and oxygen can be suppressed.

The NO generation unit 200 of the nitric oxide administration device 5 further differs as compared to the NO generation unit 200 of the nitric oxide administration device 1 shown in FIG. 1 in that there is provided a buffer tank 210 arranged upstream of the flow rate controller 202 and a pump 211 arranged upstream of the buffer tank 210. By providing the NO generation unit 200 of the nitric oxide administration device 5 with a pump 211, in the desorption process of the oxygen generation unit 100 arranged upstream, hypoxic gas released from the suction tube 105 can be sufficiently ventilated. Furthermore, in the NO generation unit 200, the gas in the second flow path 201 can be pressurized to a pressure appropriate for the generation and supply of NO. By providing the NO generation unit 200 of the nitric oxide administration device 5 with the buffer tank 210, the gas distributed from the first flow path 101 can be stored.

It should be noted that the pump 211 may be arranged in the second flow path 201 more downstream than the discharge unit 205, for example, downstream of the $NO_2$ adsorption unit 206, in this case, as described above, in the desorption process of the oxygen generation unit 100 arranged further upstream, the hypoxic gas released from the suction tube 105 can be sufficiently ventilated, and the movement of gas to discharge unit 205 can be performed at a lower pressure. By moving the gas at a lower pressure, the generation of $NO_2$ by the reaction between NO and oxygen can be suppressed. It should be noted that the nitric oxide administration device 5 may not comprise the pump 211.

Figure 6:
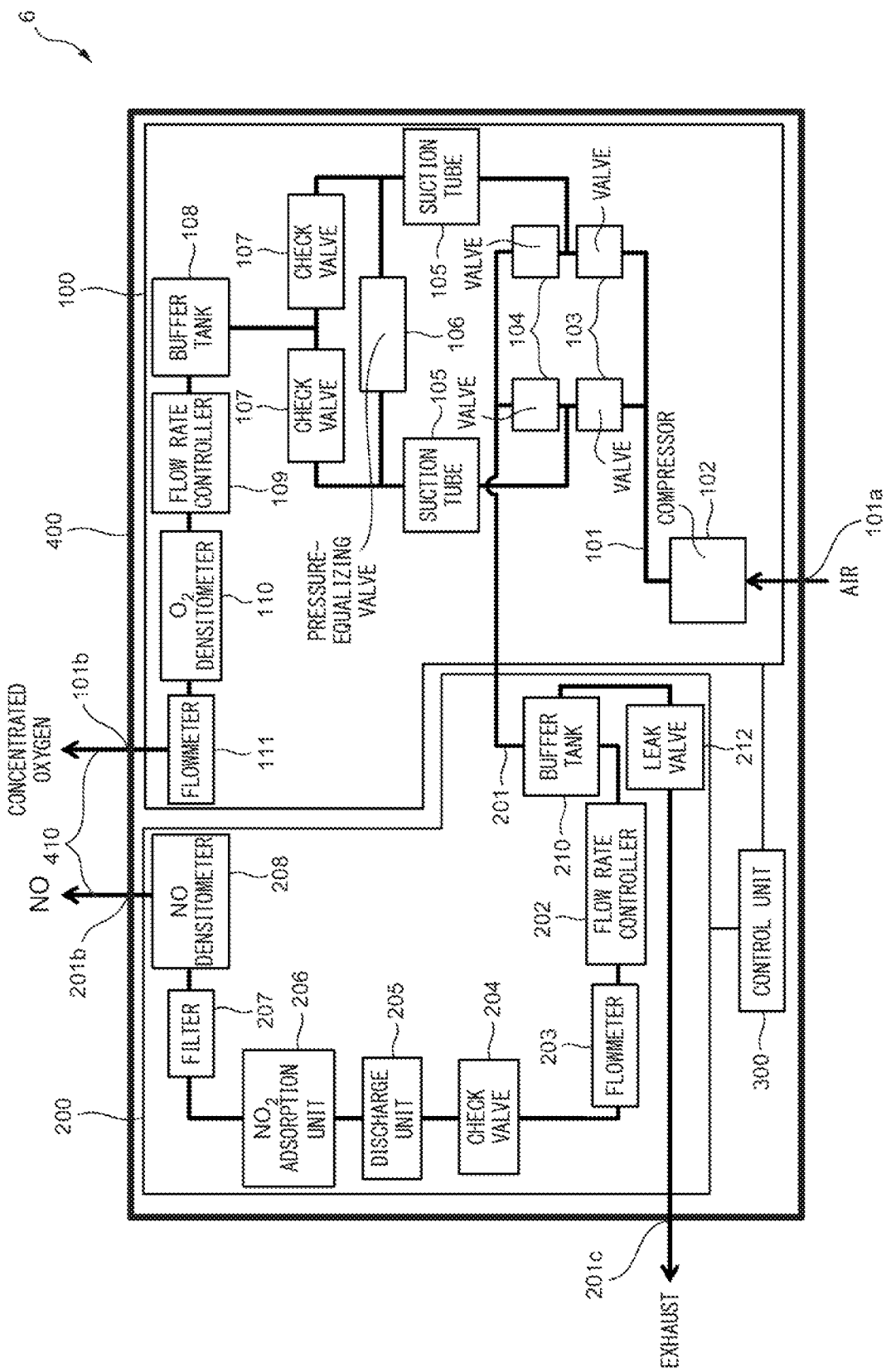
FIG. 6 is a schematic view of yet another nitric oxide administration device.

FIG. 6 is a schematic view of yet another nitric oxide administration device 6. The nitric oxide administration device 6 differs as compared with the nitric oxide administration device 5 shown in FIG. 5 in that the pump 211 is not provided, and a leak valve 212 is provided. The leak valve 212 is connected to the buffer tank 210 and can exhaust excess gas stored in the buffer tank 210 from the exhaust port 201c.

Figure 7:
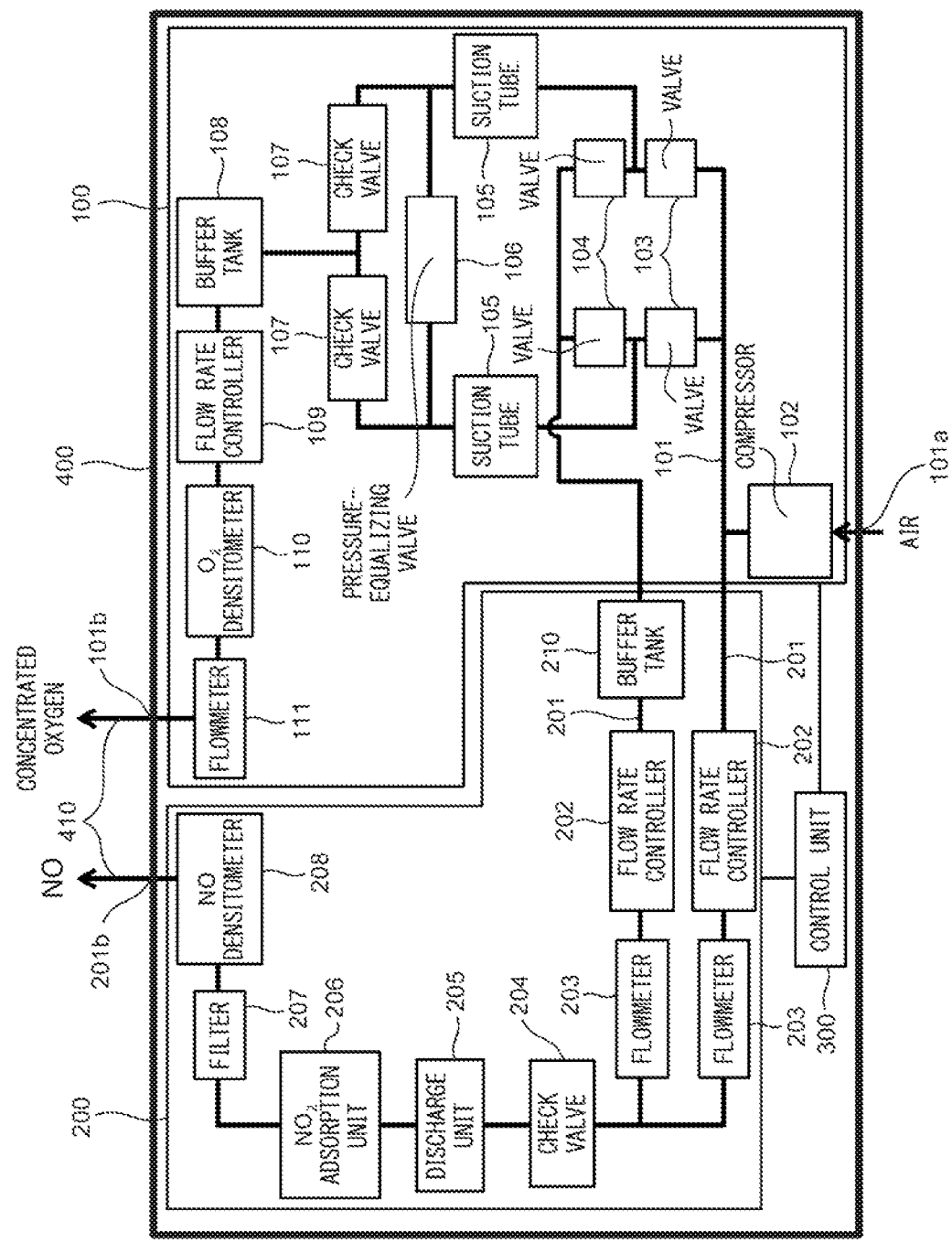
FIG. 7 is a schematic view of yet another nitric oxide administration device.

FIG. 7 is a schematic view of yet another nitric oxide administration device 7. The nitric oxide administration device 7 differs as compared to the nitric oxide administration device 5 shown in FIG. 5 in that the pump 211 is not provided and the second flow path 201 is also branched from the first flow path 101 downstream of the compressor 102. The second flow path 201 branched from the first flow path 101 downstream of the compressor 102 and the second flow path 201 branched from the first flow path 101 downstream of the pressure-reducing valve 104 of the gas flow path switching unit are combined upstream of the check valve 204. The flow rate controller 202 and the flowmeter 203 are arranged in the second flow path 201 branched from the first flow path 101 downstream of the compressor 102. By also branching the second flow path 201 from the first flow path 101 downstream of the compressor 102, the hypoxic gas described above and gas as compressed air can be mixed, whereby the oxygen concentration and NO concentration reaching the discharge unit 205 can be adjusted.

In the nitric oxide administration device 7, a pressure-reducing valve may be arranged in the second flow path 201 between the compressor 102 and the flow rate controller 202. As a result, the mixing ratio of the hypoxic gas and gas as compressed air can be changed, the oxygen concentration and NO concentration can be adjusted, and the pressure can be adjusted to appropriate levels for the generation and supply of NO. Further, the pump 211 may be arranged in the second flow path 201 upstream of the buffer tank 210 as in the nitric oxide administration device 5 shown in FIG. 5.

Figure 8:
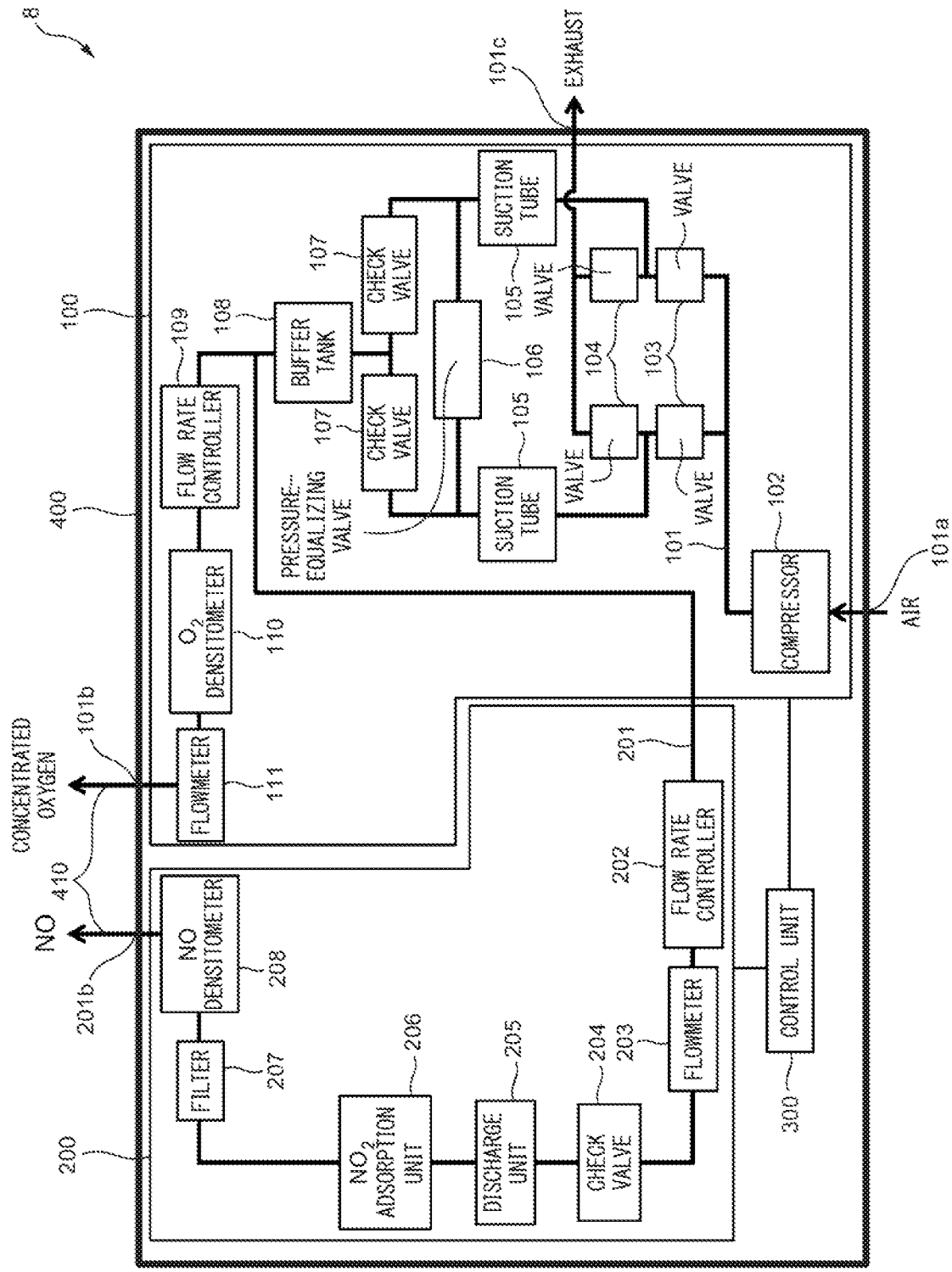
FIG. 8 is a schematic view of yet another nitric oxide administration device.

FIG. 8 is a schematic view of yet another nitric oxide administration device 8. In the nitric oxide administration device 8, the second flow path 201 is branched from the first flow path 101 between the buffer tank 108 and the flow rate controller 109. Thus, the gas (concentrated oxygen gas) containing a large amount of concentrated oxygen generated in the oxygen generation unit 100 is distributed from the first flow path 101 to the second flow path 201. In a general oxygen concentrator for adult use, concentrated oxygen having a concentration of approximately 90% or more is supplied, but in some oxygen concentrators, such as a in pediatric use, concentrated oxygen having a concentration of approximately 40% is supplied. In such a relatively low concentration oxygen concentrator, the risk of $NO_2$ generation due to contact between the concentrated oxygen and the NO is relatively low, and the NO generation efficiency can be increased depending on the configuration of the discharge unit and the discharge conditions.

The pump 211 may be arranged in the flow path 201 upstream of the flow rate controller 202. Furthermore, the pump 211 may be arranged in the second flow path 201 more downstream than the discharge unit 205, for example, downstream of the $NO_2$ adsorption unit 206.

Figure 9:
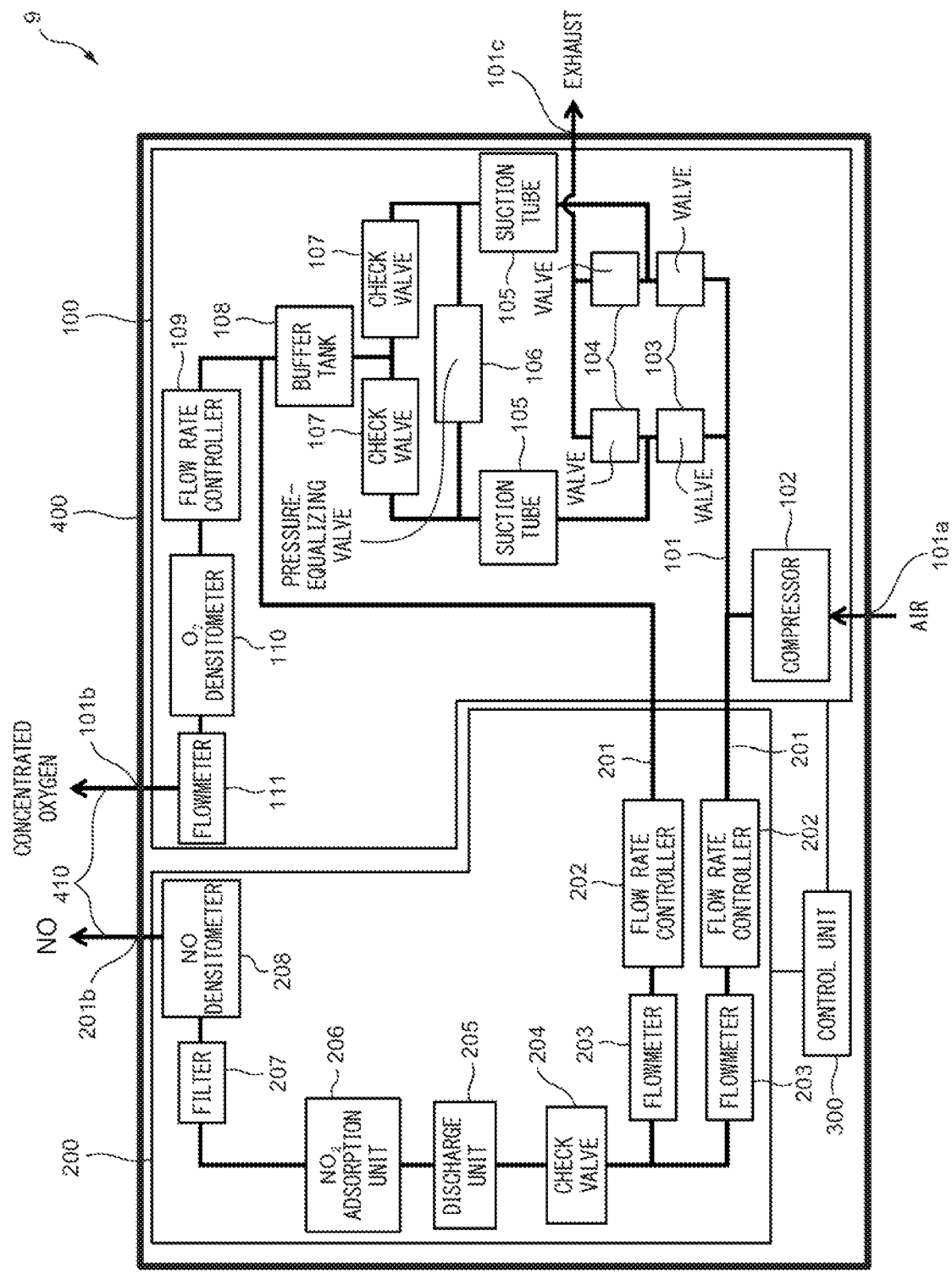
FIG. 9 is a schematic view of yet another nitric oxide administration device.

FIG. 9 is a schematic view of yet another nitric oxide administration device 9. The nitric oxide administration device 9 differs as compared to the nitric oxide administration device 5 shown in FIG. 8 in that the second flow path 201 is also branched from the first flow path 101 downstream of the compressor 102. The flow rate controller 202 and the flowmeter 203 are arranged in the second flow path 201 branched from the first flow path 101 downstream of the compressor 102. By also branching the second flow path 201 from the first flow path 101 downstream of the compressor 102, the concentrated oxygen gas described above and the gas as compressed air can be mixed, whereby the oxygen concentration and NO concentration reaching the discharge unit 205 can be adjusted.

In the nitric oxide administration device 9, a pressure-reducing valve may be arranged in the second flow path 201 between the compressor 102 and the flow rate controller 202. Furthermore, the pump 211 may be arranged upstream of the flow rate controller 202 in the second flow path 201 branched from the first flow path 101 between the buffer tank 108 and the flow rate controller 109.

Figure 10:
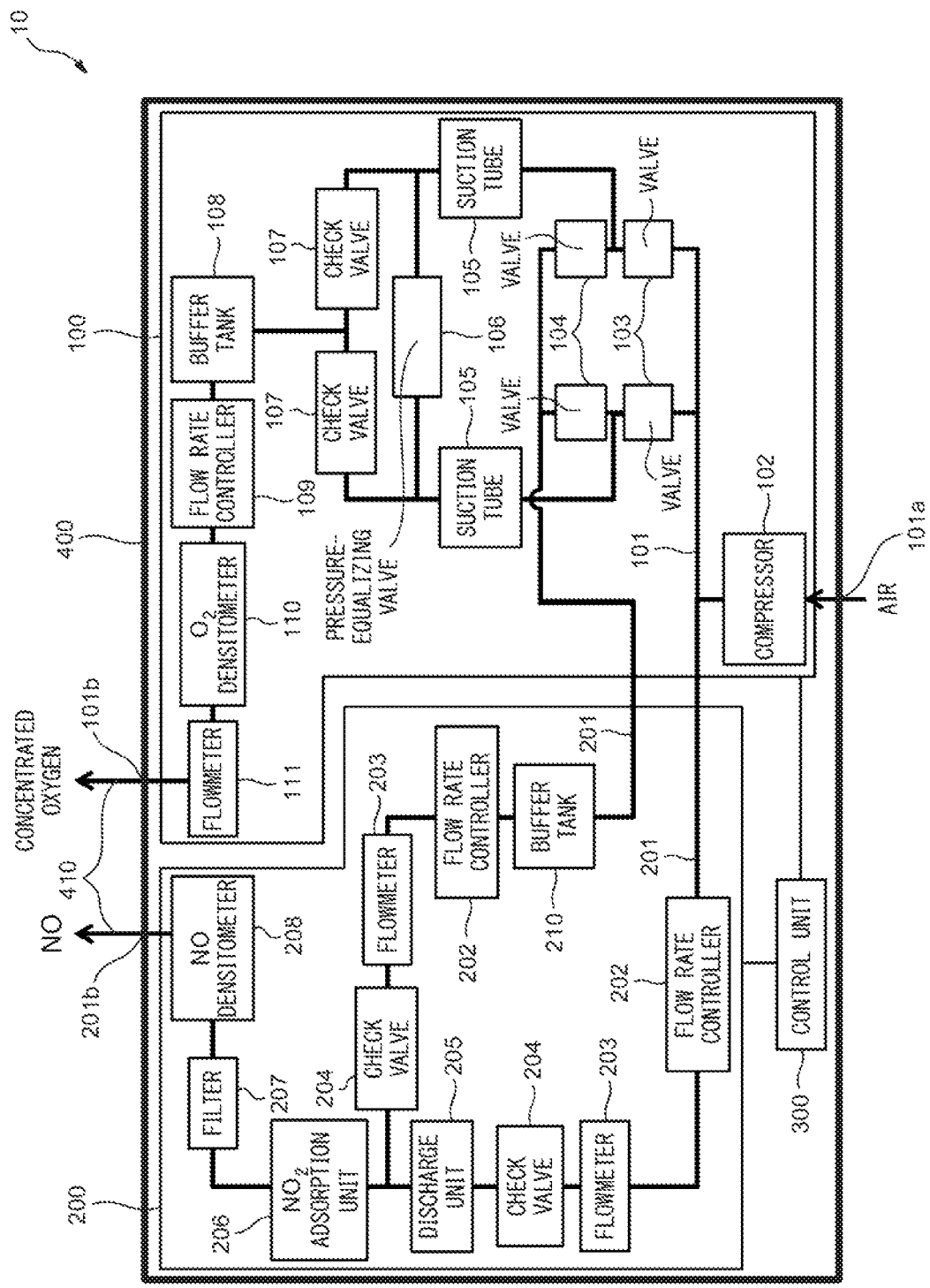
FIG. 10 is a schematic view of yet another nitric oxide administration device.

FIG. 10 is a schematic view of yet another nitric oxide administration device 10. In the nitric oxide administration device 10, like the nitric oxide administration device 7 shown in FIG. 7, the second flow path 201 is branched from the first flow path 101 between the compressor 102 and the gas flow path switching unit and is branched from the first flow path 101 downstream of the pressure-reducing valve 104 of the gas flow path switching unit. Thus, the hypoxic gas released from the adsorbent in the desorption process in the oxygen generation unit 100 is distributed from the first flow path 101 to the second flow path 201.

The nitric oxide administration device 10 differs as compared to the nitric oxide administration device 7 shown in FIG. 7 in that, in the second flow path 201 branched from the first flow path 101 downstream of the pressure-reducing valve 104 of the gas flow path switching unit, the flowmeter 203 joins the other second flow path 201 between the discharge unit 205 and the $NO_2$ adsorption unit 206 via the check valve 204. Thus, the hypoxic gas generated along with the generation of concentrated oxygen in the oxygen generation unit 100 is mixed with the generated NO in the second flow path 201 downstream of the discharge unit 205.

In the second flow path 201 downstream of the discharge unit 205, by mixing hypoxic gas, the oxygen concentration of the gas in the second flow path 201 becomes low overall. Thus, the generation of $NO_2$ due to the reaction of NO and oxygen is suppressed. In the nitric oxide administration device 10 shown in FIG. 10, NO is generated in the discharge unit 205 using a part of the compressed air contained in the oxygen by the compressor 102. Thus, the NO generation efficiency is higher than in the case in which NO is generated under hypoxic gas, for example, as in the nitric oxide administration device 5 shown in FIG. 5. Therefore, according to the nitric oxide administration device 10, the generation of $NO_2$ due to the reaction between NO and oxygen can be suppressed without lowering the generation efficiency of NO.

In the nitric oxide administration device 10, a pressure-reducing valve may be arranged in the second flow path 201 between the compressor 102 and the flow rate controller 202. The micro-differential pressure sensor 209 may be arranged in the second flow path 201 between the filter 207 and the NO densitometer 208. Further, as in the nitric oxide administration device 5 shown in FIG. 5, the pump 211 may be arranged in the second flow path 201 upstream of the buffer tank 210.

Figure 11:
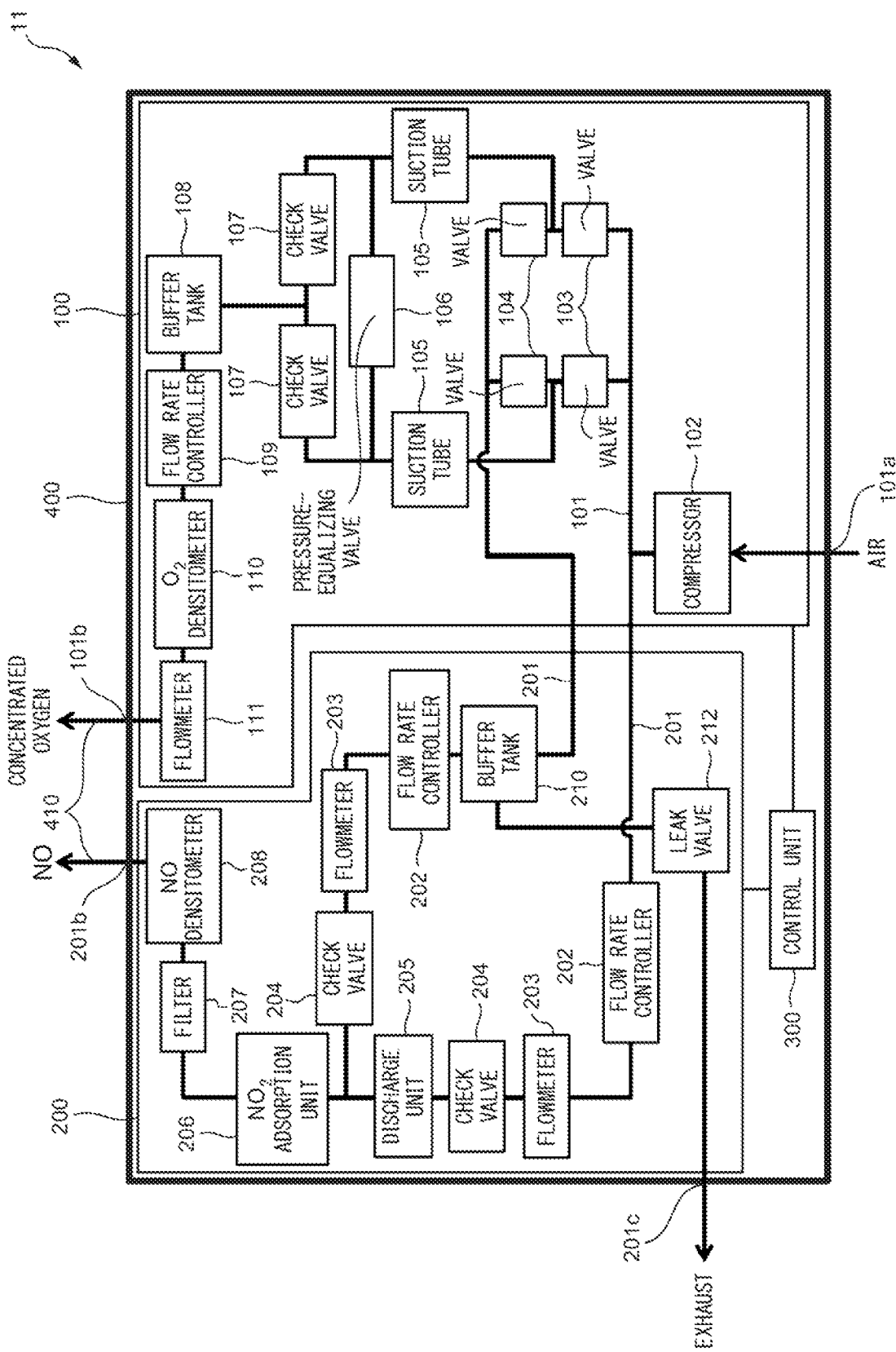
FIG. 11 is a schematic view of yet another nitric oxide administration device.

FIG. 11 is a schematic view of yet another nitric oxide administration device 11. The nitric oxide administration device 11 differs as compared with the nitric oxide administration device 10 shown in FIG. 10 in that a leak valve 212 is provided. The leak valve 212 is connected to the buffer tank 210 and can exhaust excess gas stored in the buffer tank 210 from the exhaust port 201c.

Figure 12:
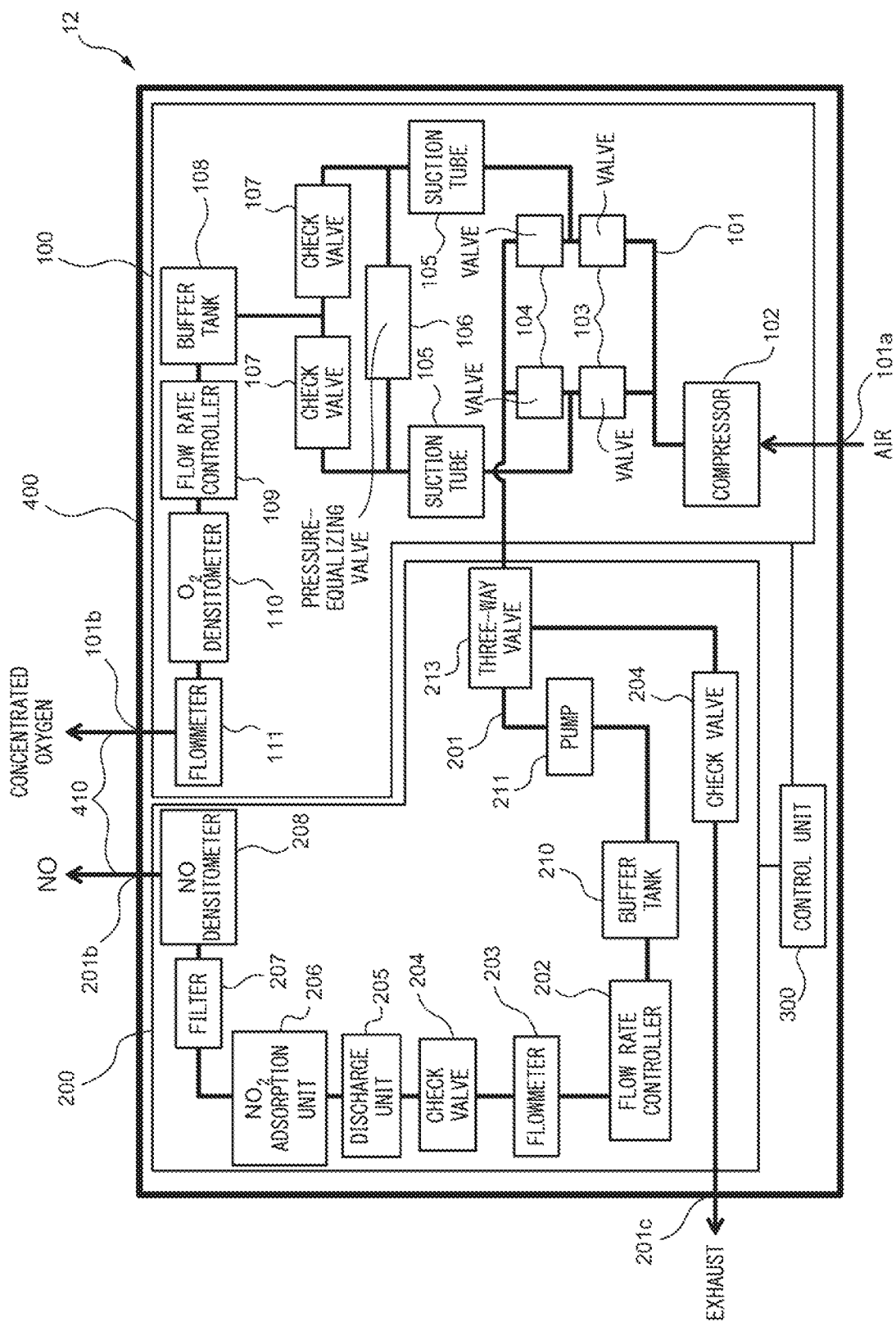
FIG. 12 is a schematic view of yet another nitric oxide administration device.

FIG. 12 is a schematic view of yet another nitric oxide administration device 12. The nitric oxide administration device 12 differs as compared to the nitric oxide administration device 5 shown in FIG. 5 in that a three-way valve 213 is arranged upstream of the pump 211, and the second flow path 201 branched from the three-way valve 213 extends to the exhaust port 201c via the check valve 204. In other words, in the second flow path 201, due to the three-way valve 213, the flow path to the NO supply port 201b and the flow path to the exhaust port 201c can be selectively switched. Thus, the three-way valve 213 constitutes a flow path switching valve for switching the opening and closing of the flow path of the hypoxic gas from the first flow path 101 to the second flow path 201.

The oxygen concentration of the gas distributed to the second flow path 201 by the gas flow path switching unit, i.e., the oxygen concentration of the gas (hypoxic gas) containing a large amount of nitrogen released from the adsorbent in the suction tube 105 in the desorption process in the oxygen generation unit 100, is not constant. The oxygen concentration of the gas distributed to the second flow path 201 fluctuates upward and downward periodically, like the pressure fluctuations along with the PSA generation of concentrated oxygen.

Thus, at the timing when the oxygen concentration is relatively high, the gas is exhausted from the exhaust port 201c by switching the three-way valve 213 to the exhaust port 201c side. Conversely, at the timing when the oxygen concentration is relatively low, gas is stored in the buffer tank 210 by switching the three-way valve 213 to the NO supply port 201b side. As a result, the pressure fluctuations and the oxygen concentration fluctuations in the second flow path 201 are suppressed. By arranging the pump 211 downstream of the three-way valve 213, the distribution of gas to the second flow path 201 can be promoted. The pump 211 can be arranged at any position as long as it is in the second flow path 201 downstream of the three-way valve 213.

Figure 13:
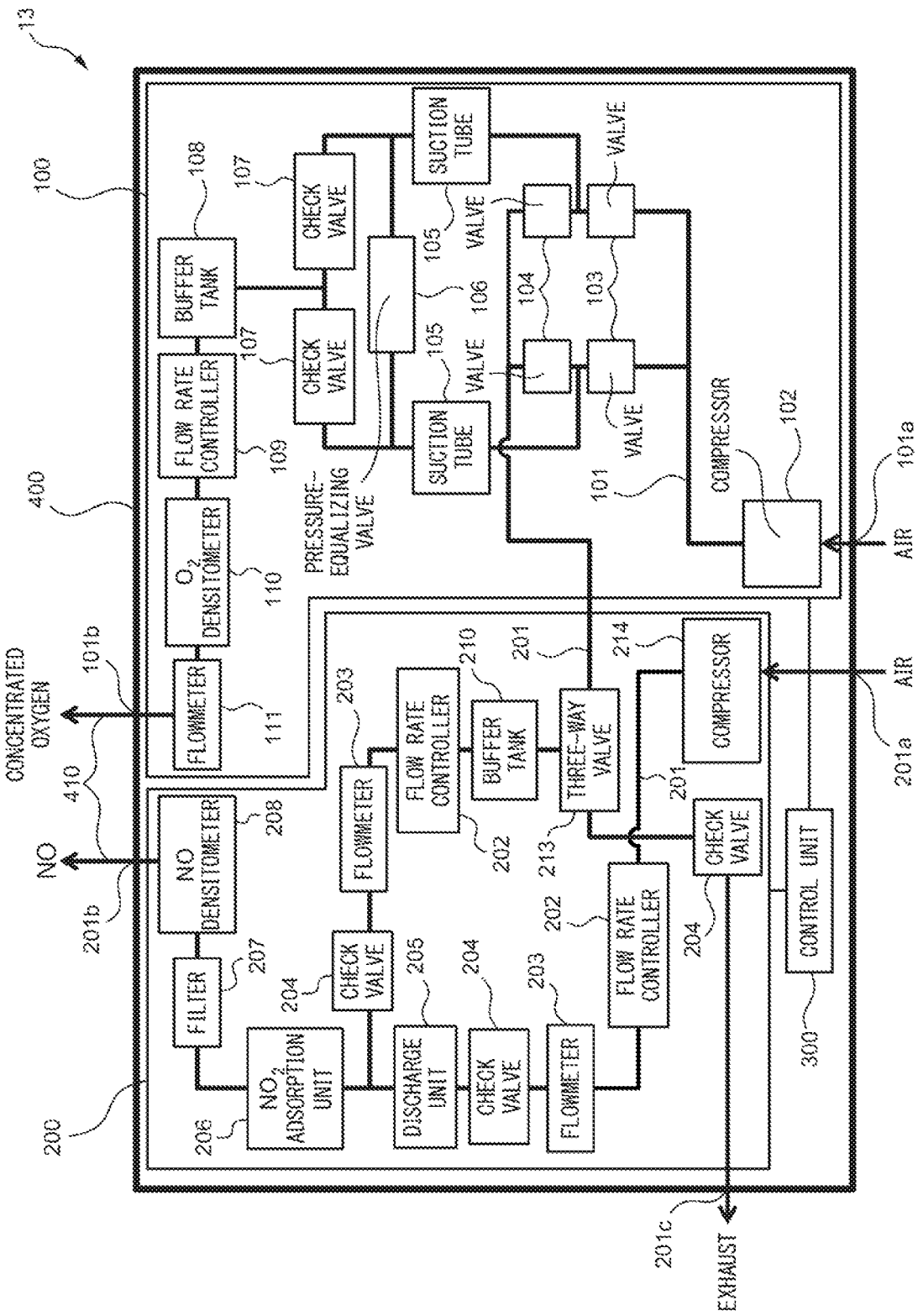
FIG. 13 is a schematic view of yet another nitric oxide administration device.

FIG. 13 is a schematic view of yet another nitric oxide administration device 13. The nitric oxide administration device 13 differs as compared to the nitric oxide administration device 11 shown in FIG. 11 in that the check valve 204 is arranged in place of the leak valve 212 and the three-way valve 213 is arranged upstream of the buffer tank 210. In other words, in the second flow path 201 branched from the first flow path 101 downstream of the gas flow path switching unit, the now path to the NO supply port 201 and the flow path to the exhaust port 201c can be selectively switched by the three-way valve 213. As a result, as described while referring to FIG. 12 pressure fluctuations and oxygen concentration fluctuations in the second flow path 201 can be suppressed.

Further, the nitric oxide administration device 13 differs significantly as compared to the nitric oxide administration device 11 shown in FIG. 11 in that the second flow path 201 including the intake port 201a is connected to the flow rate controller 202 via a compressor 214 instead of the second flow path 201 branched from the first flow path 101 between the compressor 102 and the gas flow path switching unit. In other words, in the nitric oxide administration device 13, the oxygen generation unit 100 and the NO generation unit 200 comprise independent compressor 102 and compressor 214, respectively.

The pressure and flow rate of the gas used in the generation of NO in the NO generation unit 200 are less than the pressure and flow rate of the gas used in the generation of concentrated oxygen in the oxygen generation unit 100. Thus, the compressor 214 of the NO generation unit 200 requires less pressure and flow rate than the compressor 102 of the oxygen generation unit 100, and can be thus smaller in size. By controlling the compressor 102 and the compressor 214 independently, air can be introduced at a pressure and a flow rate suitable for the generation of concentrated oxygen and the generation of NO.

The nitric oxide administration device 13 comprises the intake port 201a as a second intake port in addition to the intake port 101a as a first intake port in the oxygen generation unit 100, whereby NO can be generated from air introduced via the intake port 201a. Further, in the nitric oxide administration device 13, the generation of $NO_2$ due to the reaction of NO and oxygen can be suppressed by the hypoxic gas distributed from the first flow path 101 to the second flow path 201.

According to the nitric oxide administration devices shown in FIGS. 1 to 13 described above, Since NO and concentrated oxygen are generated separately and administered to the patient, the common effect of suppressing the generation of $NO_2$ is exhibited.

Figure 14:
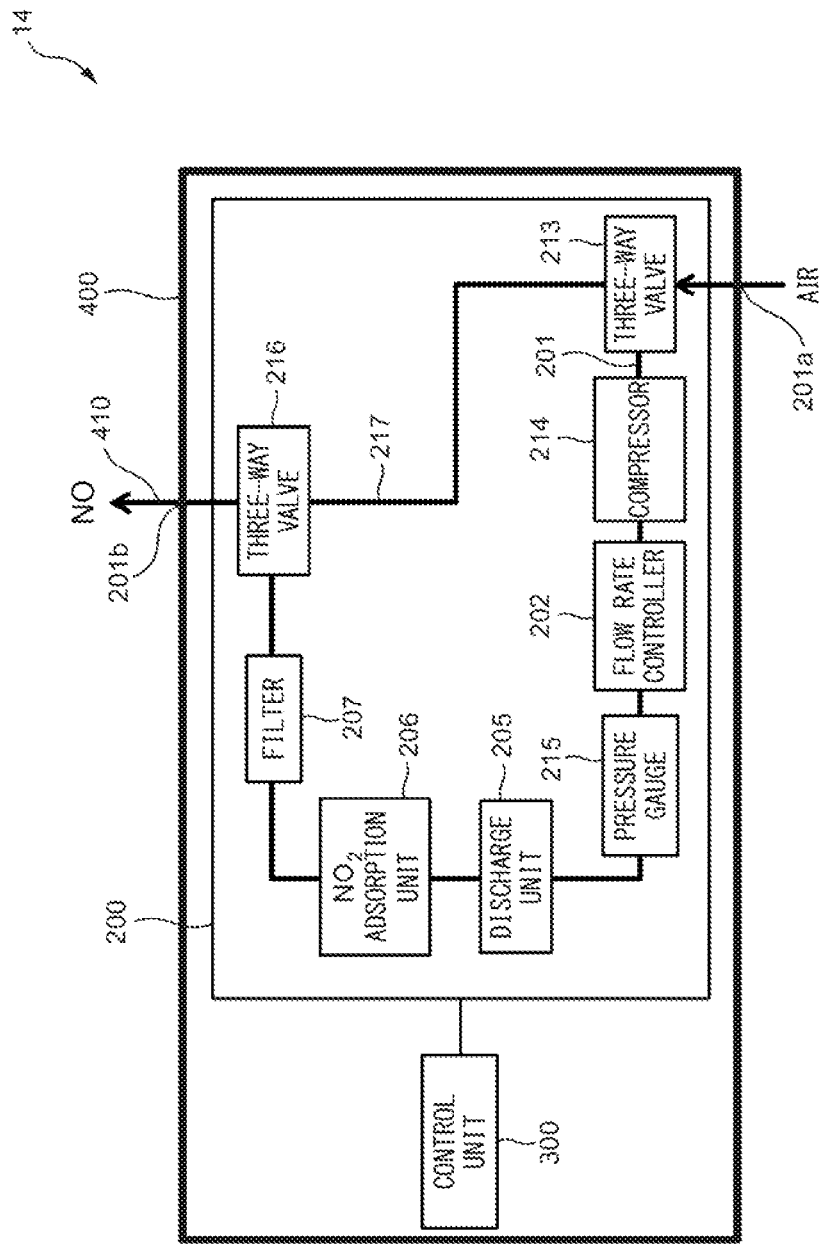
FIG. 14 is a schematic view of yet another nitric oxide administration device.

FIG. 14 is a schematic view of yet another nitric oxide administration device 14.

The nitric oxide administration device 14 comprises the second flow path 201 including the intake port 201a and the NO supply port 201b, the NO generation unit 200 which is arranged in the second flow path 201 and which generates NO from air introduced via the intake port 201a, the control unit 300, and the housing 400. The NO generation unit 200 and the control unit 300 are housed in the interior of the housing 400. The NO generated by the NO generation unit 200 is supplied via the NO supply port 201b. The various operations of the NO generation unit 200 are controlled by the control unit 300.

The NO generation unit 200 comprises, in the second flow path 201, the three-way valve 213 arranged downstream of the intake port 201a, the compressor 214 as an air compressor arranged downstream of the three-way valve 213, the flow rate controller 202 arranged downstream of the compressor 214, a pressure gauge 215 arranged downstream of the flow rate controller 202, the discharge unit 205 described above arranged downstream of the pressure gauge 215, the $NO_2$ adsorption unit 206 described above arranged downstream of the discharge unit 205, the filter 207 described above arranged downstream of the $NO_2$ adsorption unit 206, and a three-way valve 216 arranged downstream of the filter 207.

As described above, $NO_2$ is highly toxic and is also generated by reacting the generated NO with unreacted oxygen during discharge in the discharge unit 205 before inhalation by the patient. Thus, for example, if NO is generated in the discharge unit 205 and stays in the second flow path 201, $NO_2$ will be generated during that time. In the nitric oxide administration device 14, by providing the three-way valve 213 and the three-way valve 216, gas is refluxed in the interior of the nitric oxide administration device 14 to suppress increases in the concentration of $NO_2$ contained in the gas. In other words, switching of the flow path from downstream of the $NO_2$ adsorption unit 206 to the NO supply port 201b and the flow path from downstream of the $NO_2$ adsorption unit 206 to upstream of the discharge unit 205 can be performed, preferably selectively.

Specifically, regarding the gas containing NO generated by the discharge unit 205, $NO_2$ in the gas is adsorbed by the $NO_2$ adsorption unit 206 arranged downstream of the discharge unit 205. When the gas containing NO downstream of the $NO_2$ adsorption unit 206 is not immediately administered to the patient, the three-way valve 216 is switched so that the downstream of the second flow path 201 and a bypass flow path 217 communicate with each other. Simultaneously, the three-way valve 213 is switched, and the bypass flow path 217 and upstream of the second flow path 201 communicate with each other. Thus, the gas containing NO generated by the discharge unit 205 is introduced from downstream of the filter 207 to upstream of the second flow path 201 via the bypass flow path 217, and thereafter, refluxes the interior of the nitric oxide administration device 14 while being pressurized by the compressor 214. Conversely, by switching the three-way valve 216 to the NO supply port 201b side and switching the three-way valve 213 to the intake port 201a side, administration to the patient can be started.

Figure 15:
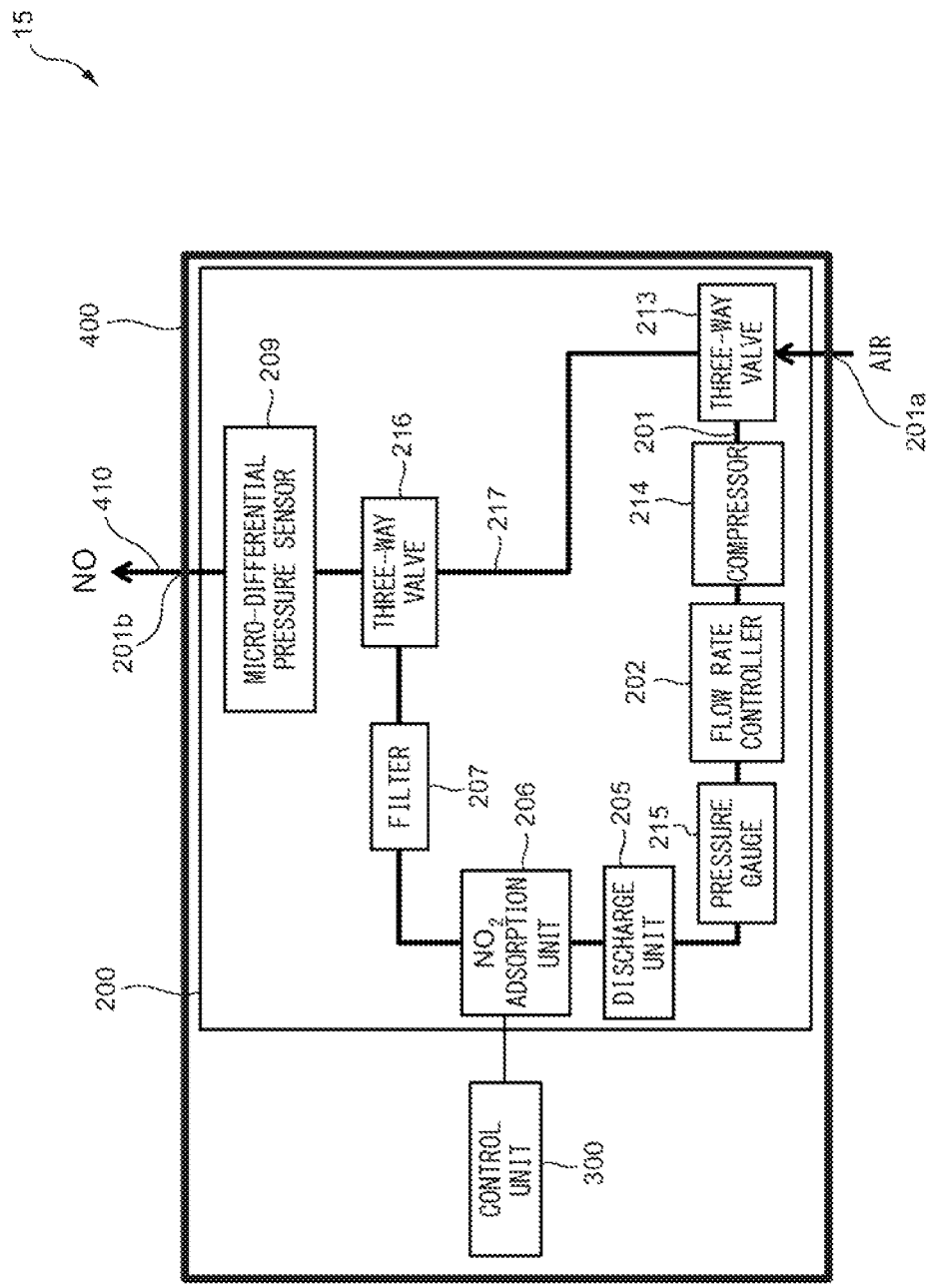
FIG. 15 is a schematic view of yet another nitric oxide administration device.

It should be noted that in the nitric oxide administration device 14, the switching of the three-wave valve 213 and the three-way valve 216, i.e., reflux, is performed intermittently at predetermined timings. However, the nitric oxide administration device 14 may be configured so as to perform switching in synchronization with the respiration of the patient. In this case, the micro-differential pressure sensor 209 is arranged between the three-way valve 216 and the NO supply port 201b as in, for example, the nitric oxide administration device IS shown in FIG. 15. Respiration of the patient is detected by the micro-differential pressure sensor 209, and switching of the three-way valve 213 and the three-way valve 216 can be performed. Control of the discharge unit 205 can be performed using the micro-differential pressure sensor 209.

Furthermore, in the nitric oxide administration device 14 shown in FIG. 14, the flow rate controller 202 may be arranged upstream of the three-way valve 213, and the discharge unit 205 may be arranged in the second flow path 201 between the three-way valve 213 and the compressor 214. By arranging the discharge unit 205 further upstream, since the interval in which the gas containing the generated NO moves at low pressure becomes long, the generation of $NO_2$ due to the reaction of NO and oxygen is suppressed.

Figure 16:
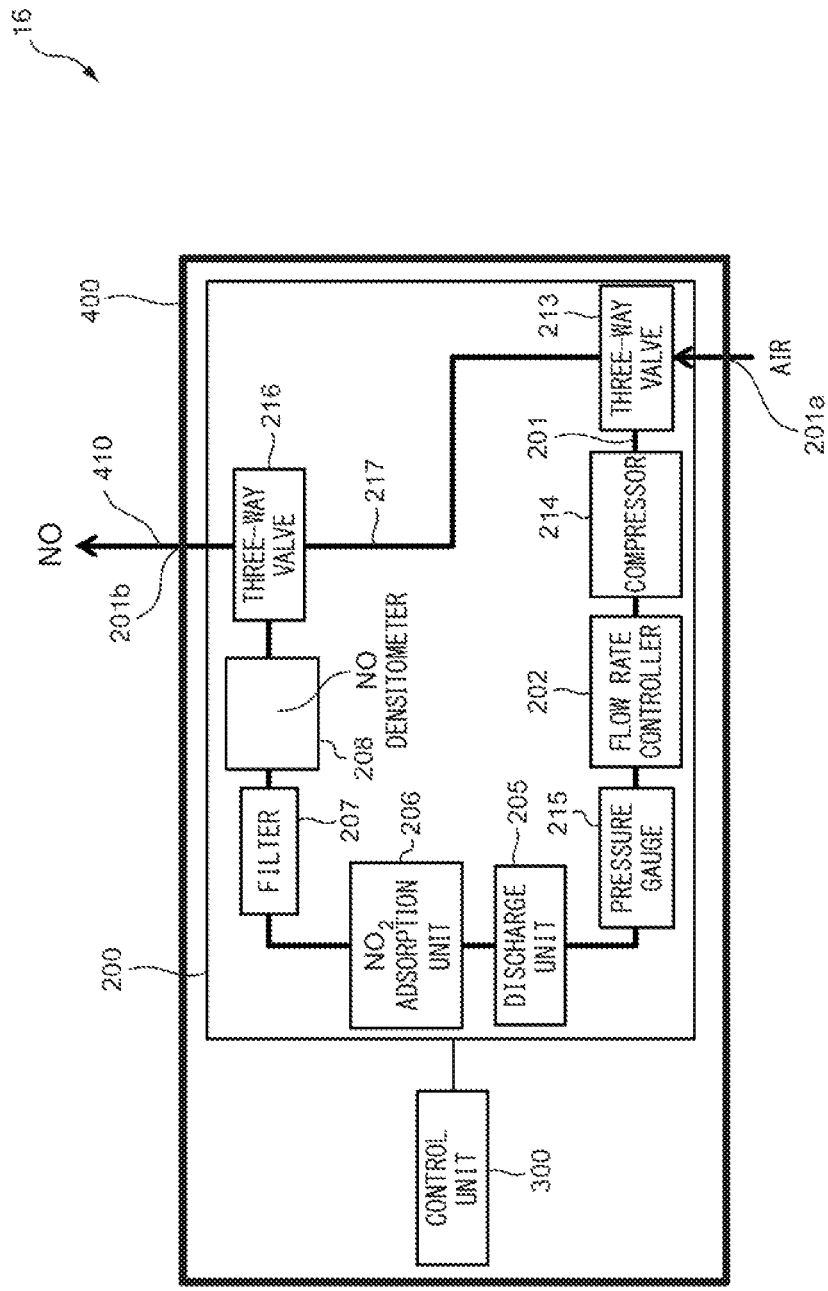
FIG. 16 is a schematic view of yet another nitric oxide administration device.

As in the nitric oxide administration device 16 shown in FIG. 16, the NO densitometer 208 may be arranged in the second flow path 201 between the filter 207 and the three-way valve 216. Furthermore, the NO densitometer 208 may be arranged between the three-way valve 16 and the NO supply port 201b. The NO densitometer 208 measures the NO concentration most downstream of the second flow path 201, and measures whether or not the NO concentration is problematic for administration to the patient. The results thereof are fed back to, for example, the flow rate controller 202 and the discharge unit 205, and the generation amount and concentration of NO are adjusted.

Figure 17:
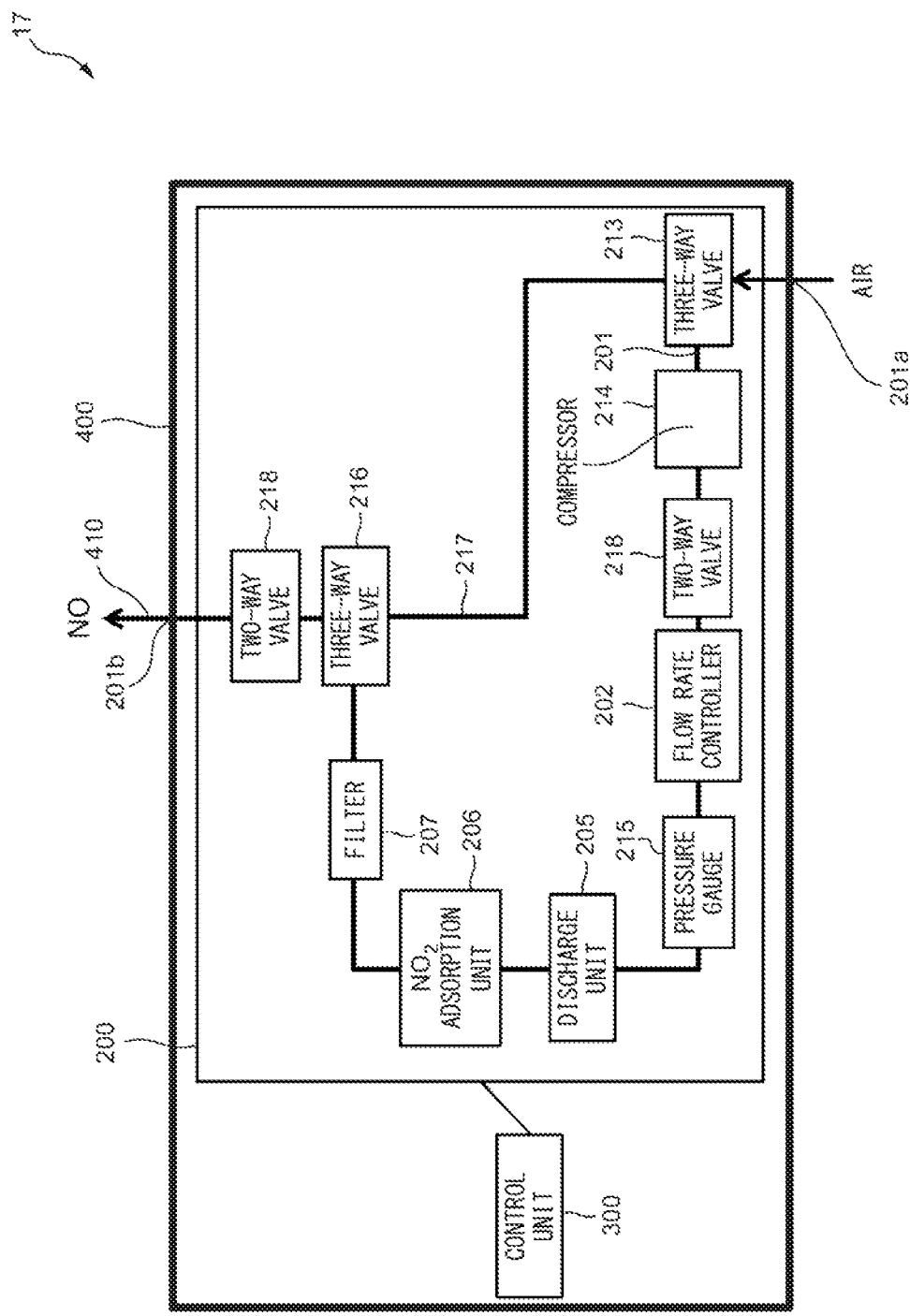
FIG. 17 is a schematic view of yet another nitric oxide administration device.

FIG. 17 is a schematic view showing yet another nitric oxide administration device 17. The nitric oxide administration device 17 differs as compared to the nitric oxide administration device 14 shown in FIG. 14 in that two-way valves 218 are further arranged in the second flow path 201 between the compressor 214 and the flow rate controller 202 and downstream of the three-way valve 216. In the case of a patient having a high respiration frequency, the residence time of the gas containing generated NO is lower in the synchronized flow mode than in the case of a patient having a low respiration frequency. Thus, it may not be necessary to reflux the gas inside the nitric oxide administration device to suppress the increase in the concentration of $NO_2$ contained in the gas. In the nitric oxide administration device 17 shown in FIG. 17, since a two-way valve 218 is further arranged downstream of the three-way valve 216. i.e., upstream of the NO supply port 201b, in the case of a patient having a high respiration frequency, the three-way valve 216 is switched to the flow path on the NO supply port 201b side and the opening and closing of the two-way valve 218 upstream of the NO supply port 201b is switched, whereby the gas containing NO can be administered to the patient without refluxing of the gas. Furthermore, since the time waiting for inhalation changes slightly for each respiration, the maximum pressure of the flow path prior to administration also changes for each respiration. By arranging the two-way valve 218 in the second flow path 201 between the compressor 214 and the flow rate controller 202 downstream of the compressor 214 as shown in FIG. 17, the maximum pressure of the gas in the second flow path 201 prior to administration can be controlled to be constant. Thus, the dosage to the patient can be controlled to the desired amount without controlling the opening and opening time of the two-way valve 218 or three-way valve 216 upstream of the NO supply port 201b in accordance with the fluctuations of the pressure in the flow path. It should be noted that it is not necessary to arrange the two-way valve 218 in the second flow path 201 between the compressor 214 and the flow rate controller 202. Conversely, in another nitric oxide administration device having a bypass flow path described herein, a two-way valve 218 may be arranged in the flow path downstream of the compressor 214 like the nitric oxide administration device 17 shown in FIG. 17.

It should be noted that the frequency of respiration is determined by whether the frequency of respiration, for example, the respiratory rate per minute or unit time, is higher or lower than a predetermined respiratory rate. The predetermined respiratory rate is determined from the permissible values of the decrease in NO concentration or the increase in the concentration of $NO_2$.

Figure 18:
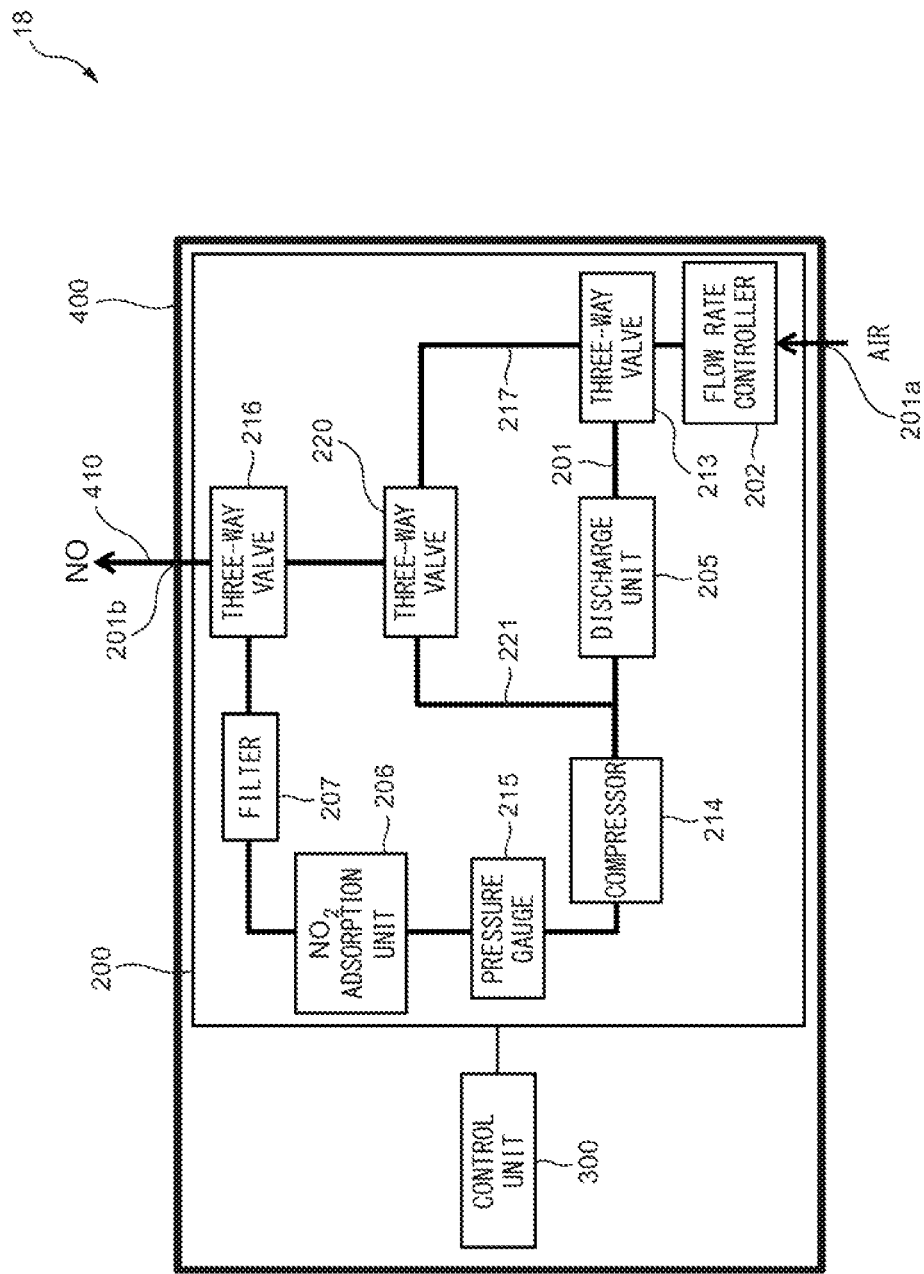
FIG. 18 is a schematic view of yet another nitric oxide administration device.

FIG. 18 is a schematic view of yet another nitric oxide administration device 18. The nitric oxide administration device 18 differs as compared to the nitric oxide administration device 14 shown in FIG. 14 in that the flow rate controller 202 is arranged upstream of the three-way valve 213 and the discharge unit 205 is arranged in the second flow path 201 between the three-way valve 213 and the compressor 214. Further, in the nitric oxide administration device 18, a three-way valve 220 is arranged in the bypass flow path 217, and a bypass flow path 221 is further branched from the bypass flow path 217.

As described above, when the gas containing NO downstream of the $NO_2$ adsorption unit 206 is not immediately administered to the patient, the three-way valve 216 is switched so that the downstream of the second flow path 201 and the bypass flow path 217 communicate with each other. At this time, when the fluctuations in the concentrations of NO and $NO_2$ are small and no further generation of NO is necessary, the three-way valve 220 is switched, and the bypass flow path 217 and the second flow path 201 downstream of the discharge unit 205 communicate with each other via the bypass flow path 221. The reflux path can be shortened by refluxing to the downstream of discharge unit 205.

Figure 19:
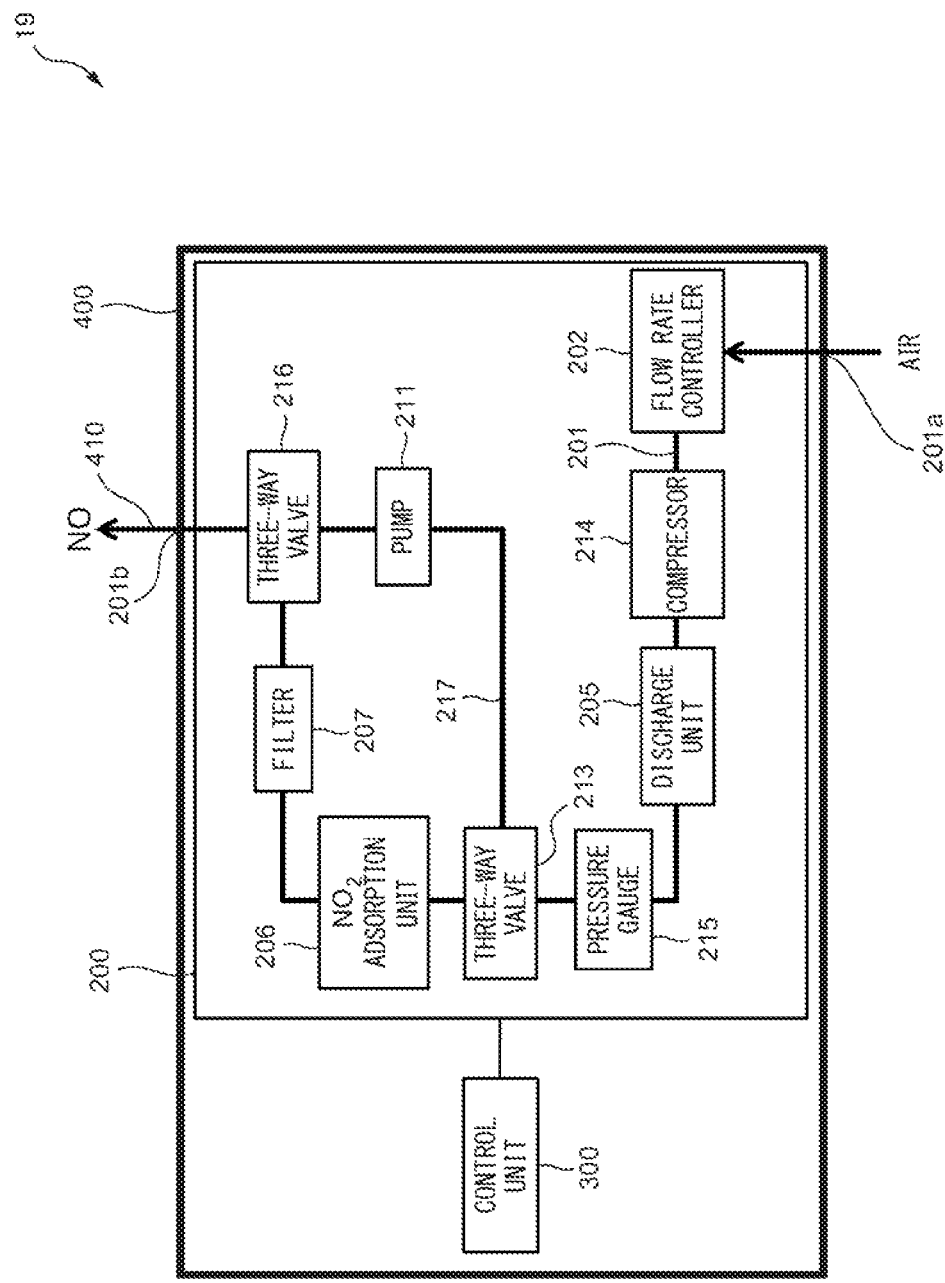
FIG. 19 is a schematic view of yet another nitric oxide administration device.

FIG. 19 is a schematic view of yet another nitric oxide administration device 19. The nitric oxide administration device 19 differs as compared to the nitric oxide administration device 14 shown in FIG. 14 in that the flow rate controller 202 is arranged downstream of the intake port 201a and the discharge unit 205 is arranged between the compressor 214 and the pressure gauge 215. Further, in the nitric oxide administration device 19, the three-way valve 213 is arranged between the $NO_2$ adsorption unit 206 and the pressure gauge 215.

As described above, when the gas containing NO downstream of the $NO_2$ adsorption unit 206 is not immediately administered to the patient, the three-way valve 216 is switched, and the downstream of the second flow path 201 and the bypass flow path 217 communicate with each other. Simultaneously, the three-way valve 213 is switched, and the bypass flow path 217 and the second flow path 201 communicate with each other via the pump 211. Thus, in the nitric oxide administration device 19, the reflux path of the gas containing NO generated by the discharge unit 205 can be shortened as compared to the nitric oxide administration device 18 shown in FIG. 18.

When the fluctuations in the concentrations of NO and $NO_2$ are small and no further generation of NO is necessary, by refluxing to the downstream of discharge unit 205, the reflux pathway can be shortened, and the generation of $NO_2$ due to the reaction of NO and oxygen is suppressed. In particular, in the nitric oxide administration device 18 shown in FIG. 18, both the case in which it is necessary to reflux through the discharge unit 205 and the case in which it is not necessary to reflux through the discharge unit 205 can be handled.

The nitric oxide administration devices shown in FIGS. 14 to 19 described above comprise a three-way valve 216 which selectively switches a flow path from downstream of the $NO_2$ adsorption unit 206 to the NO supply port 201b and a flow path from downstream of the $NO_2$ adsorption unit 206 to upstream of the $NO_2$ adsorption unit 206. Thus, the three-way valve 216 is configured as a first flow path switching unit which switches the opening and closing of the flow path from at least downstream of the $NO_2$ removal unit to the supply port. For example, by the first flow path switching unit, switching to the flow path from downstream of the $NO_2$ removal unit to the supply port when the patient inhales is performed using, for example, the start of inhalation as a trigger, and switching to the flow path from downstream of the $NO_2$ removal unit to upstream of the $NO_2$ removal unit when the patient exhales is performed using, for example, the start of exhalation as a trigger. From the trigger of the start of inhalation of the patient, the flow path from downstream of the $NO_2$ removal unit to upstream of the $NO_2$ removal unit may be switched after a predetermined time has elapsed. The gas inhaled immediately before the end of inhalation does not reach the alveoli, and thus, does not contribute to the therapeutic effect, and is exhaled into the surroundings at the time of exhalation. Thus, the flow path from downstream of the $NO_2$ removal unit to upstream of the $NO_2$ removal unit may be switched before the end of inhalation.

Furthermore, the opening time of the first flow path switching unit or the amount of air drawn from the intake port 201a may be adjusted so as to increase when the respiratory rate per unit time of the patient is less than a predetermined value, or may be adjusted so as to decrease when the respiratory rate per unit time of the patient is higher than a predetermined value. The drawing of air from the intake port 201a may be performed in accordance with the administration of NO to the patient. The discharge by the discharge unit 205 may be performed in accordance with the administration of NO to the patient or the drawing of air from the intake port 201a. At the time of administration of NO to the patient or at the time of drawing of air from the intake port 201a, discharge by the discharge unit 205 may be performed so as to generate more NO than at other times. Discharge by the discharge unit 205 may be performed so as to maintain the NO concentration at times other than the time of administration of NO to the patient or the time of drawing of air from the intake port 201a. When the amount of air drawn from the intake port 201a is greater than a predetermined value, or when the residence time of the gas is longer than a predetermined value, the discharge by the discharge unit 205 may be performed so as to generate more NO. The flow rate of at least a portion of the flow path between the discharge unit 205 and the NO supply port 201b may be adjusted in accordance with the total volume of the flow path.

Further, in the nitric oxide administration device 18 shown in FIG. 18, there is provided a three-way valve 220 which selectively switches, from downstream of the $NO_2$ adsorption unit 206, the flow path to upstream of the discharge unit 205 and the flow path to downstream of the discharge unit 205. Thus, the three-way valve 220 constitutes a second flow path switching unit. The second flow path switching unit switches to the flow path upstream of the discharge unit 205 when the respiration frequency of the patient is lower than a predetermined frequency, and switches to the flow path downstream of the discharge unit 205 when the respiration frequency of the patient is higher than the predetermined frequency.

There is further provided an $NO_2$ measurement unit which measures the concentration or substance amount of $NO_2$ in the flow path, and when the concentration or substance amount of $NO_2$ measured by the $NO_2$ measurement unit is lower than a predetermined first value, switching to the flow path from downstream of the $NO_2$ removal unit to the NO supply port 201b may be performed by the first flow path switching unit, and when the concentration or substance amount of $NO_2$ measured by the $NO_2$ measurement unit is greater than the predetermined first value, switching to the flow path from downstream of the $NO_2$ removal unit to upstream of the $NO_2$ removal unit may be performed by the first flow path switching unit.

There is further provided an NO measurement unit which measures the concentration or substance amount of NO in the flow path, and when the concentration or substance amount of NO measured by the NO measurement unit is lower than a predetermined second value, switching to the flow path to upstream of the discharge unit 205 may be performed by the second flow path switching unit, and when the concentration or substance amount of NO measured by the NO measurement unit is higher than the predetermined second value, switching to the flow path to downstream of the discharge unit 205 may be performed by the second flow path switching unit.

As in the NO densitometer 208 shown in FIG. 16, the NO measurement unit or $NO_2$ measurement unit is preferably arranged between the filter 207 and the three-way valve 216. As a result, the concentration or substance amount of NO or $NO_2$ can be measured immediately prior to administration to the patient, whereby the dosage can be more appropriately adjusted. The NO measurement unit or $NO_2$ measurement unit may be arranged between the three-way valve 216 and the NO supply port 201b.

According to the nitric oxide administration devices shown in FIGS. 14 to 19 described above, the common effect of suppressing increases in the $NO_2$ concentration is exhibited. Though the nitric oxide administration devices shown in FIGS. 14 to 19 do not comprise an oxygen generation unit 1M, they may comprise an oxygen generation unit 100 like the nitric oxide administration device 1 shown in FIG. 1, etc. Further, the $NO_2$ adsorption unit may be arranged in the flow path more downstream than the NO supply port 201b, as in the nitric oxide administration device described later with reference to FIG. 25. In this case, the upstream side of the $NO_2$ adsorption unit is connected to the NO supply port 201b via an extension tube, and the downstream side of the $NO_2$ adsorption unit is connected to the upstream end of the cannula 410.

Figure 20:
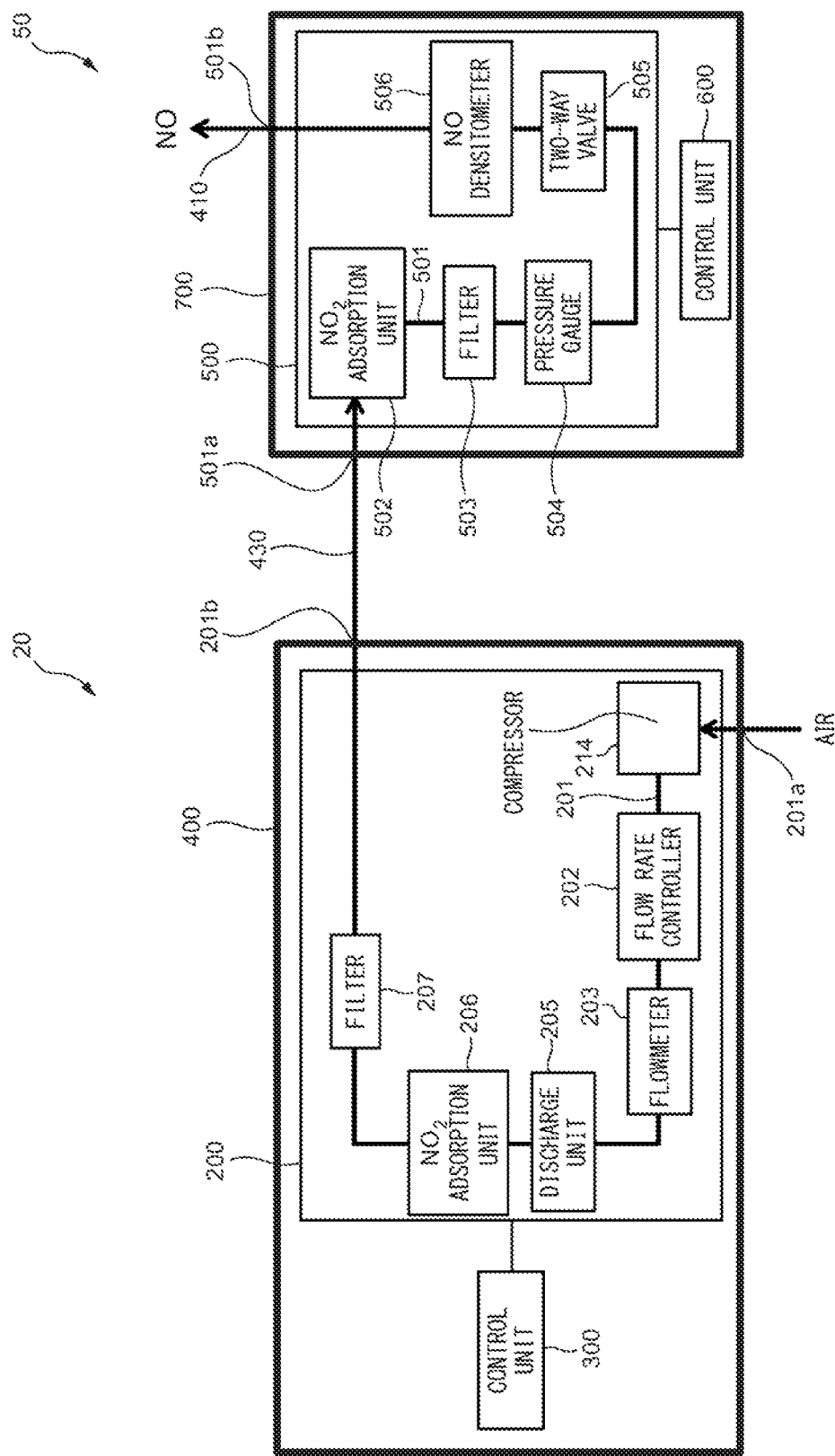
FIG. 20 is a schematic view of a nitric oxide administration device and relay administration device.

FIG. 20 is a schematic view of a nitric oxide administration device 20 and relay administration device 50. The relay administration device 50 is connected to the nitric oxide administration device 20, which supplies NO generated from air.

The nitric oxide administration device 20 comprises the second flow path 201 including the intake port 201a and the NO supply port 201b, the NO generation unit 200, which is arranged in the second flow path 201 and which generates NO from air introduced via the intake port 201a, the control unit 300, and the housing 400. The NO generation unit 200 and the control unit 300 are housed in the interior of the housing 400. The NO generated by the NO generation unit 200 is supplied via the NO supply port 201b. The various operations of the NO generation unit 200 are controlled by the control unit 300.

The NO generation unit 200 comprises, in the second flow path 201, the compressor 214 as an air compressor arranged downstream of the intake port 201a, the flow rate controller 202 arranged downstream of the compressor 214, the flowmeter 203 arranged downstream of the flow rate controller 202, the discharge unit 205 described above arranged downstream of the flowmeter 203, the $NO_2$ adsorption unit 206 described above arranged downstream of the discharge unit 205, and the filter 207 described above arranged downstream of the $NO_2$ adsorption unit 206.

The upstream side of the relay administration device 50 is connected to the NO supply port 201b via the extension tube 430, and the downstream side of the relay administration device 50 is connected to the upstream end of the cannula 410. The relay administration device 50 comprises a third flow path 501 including an upstream side connection end 501a and a downstream side connection end 501b, a dosage adjustment unit 500 arranged in the third flow path 501 and which adjusts the dosage of gas introduced via the upstream side connection end 501a, a control unit 600, and a housing 700. The NO generation unit 200 and the control unit 300 are housed in the interior of the housing 400.

The gas adjusted by the dosage adjustment unit 500 is supplied via the downstream side connect end 501b. The various operations of the dosage adjustment unit 500 are controlled by the control unit 600. The relay administration device 50 is connected to a power source via a power cable (not illustrated). However, the relay administration device 50 may have a battery which can be housed in the interior of the housing 700 and used as a power source. In place of the control unit 600, the nitric oxide administration device 20 and the relay administration device 50 may be electrically connected so that the various operations of the dosage adjustment unit 500 are controlled by the control unit 300.

The dosage adjustment unit 500 comprises, in the third flow path 501, an $NO_2$ adsorption unit 502 arranged downstream of the upstream side connection end 501a, a filter 503 arranged downstream of the $NO_2$ adsorption unit 502, a pressure gauge 504 arranged downstream the of filter 503, a two-way valve 505, which is an adjustment valve, arranged downstream of the pressure gauge 504, and an NO densitometer 506 arranged downstream of the two-way valve 505. The $NO_2$ adsorption unit 502 and the filter 503 are identical to the $NO_2$ adsorption unit 206 and filter 207 described above, respectively.

As described above, $NO_2$ is highly toxic and is generated by the reaction of the generated NO with unreacted oxygen during discharge prior to inhalation by the patient. Thus, depending on the usage environment of the nitric oxide administration device, the longer the cannula, the longer the time during which NO and oxygen may react becomes, and thus, at the same flow rate, the amount of NO actually administered to the patient decreases. By using the relay administration device 50 together with the nitric oxide administration device 20, the dosage immediately prior to administration to the patient can be adjusted and the absolute amount of NO administered to the patient can be adjusted.

The NO concentration immediately prior to administration to the patient is measured by the NO densitometer 506 arranged most downstream in the relay administration device 50. When it is determined by the control unit 600 that the dosage is small, the opening and time of the two-way valve 505 are adjusted based on the value of the pressure gauge 504, and the dosage is increased by increasing the flow rate. Conversely, when it is determined by the control unit 600 that the dosage is large, the opening and time of the two-way valve 505 are adjusted based on the value of the pressure gauge 504, and the dosage is lowered by reducing the flow rate.

The relay administration device 50 comprises the $NO_2$ adsorption unit 502, whereby it is possible to adsorb $NO_2$ generated after $NO_2$ is adsorbed by the $NO_2$ adsorption unit 206 of the nitric oxide administration device 20. Furthermore, the relay administration device 50 comprises the filter 503, whereby it is possible to remove dirt and dust in the gas introduced to the relay administration device 50 via the extension tube 430.

Figure 2:
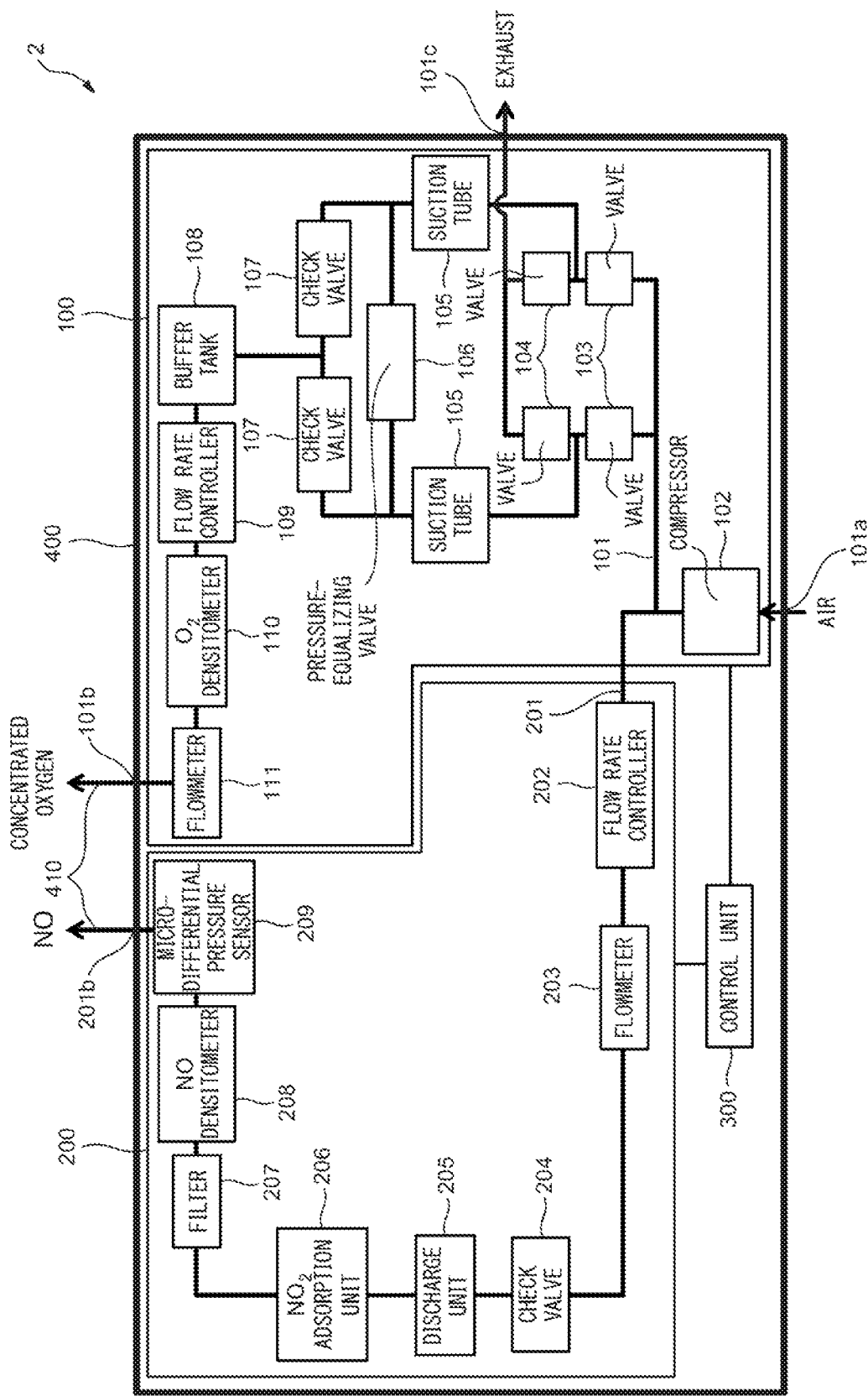
FIG. 2 is a schematic view of another nitric oxide administration device.

In the nitric oxide administration device 2, which comprises the micro-differential pressure sensor 209, as shown in FIG. 2, when the cannula 410 and the extension tube 430 are connected to the nitric oxide administration device 2 without a relay administration device 50, depending on the length of the extension tube 430, the time until respiration is detected and the delay time of the administration become long, whereby the administration of NO may not be completed during the effective inhalation period. Thus, a micro-differential pressure sensor is arranged downstream of the NO densitometer 506 to detect the negative pressure due to patient respiration. By controlling the two-way valve 505 in synchronization with this, the flow or stoppage of NO may be controlled, and the administration or stoppage of NO may be controlled. As a result, the delay time of respiration detection and administration in accordance with the extension tube length can be shortened. In place of a micro-differential pressure sensor, another respiration detection unit such as oral and nasal thermistors may be used. The patient respiration detected by the respiration detection unit may be transmitted to the relay administration device 50 by wire or wirelessly as a signal of respiration information to control the two-way valve 505.

In place of the NO densitometer 506, an $NO/NO_2$ densitometer may be arranged. Furthermore, a pump may be arranged in the in the third flow path 501 upstream of the two-way valve 505. By arranging a pump, pressurization to an appropriate pressure for NO supply can be performed.

Figure 21:
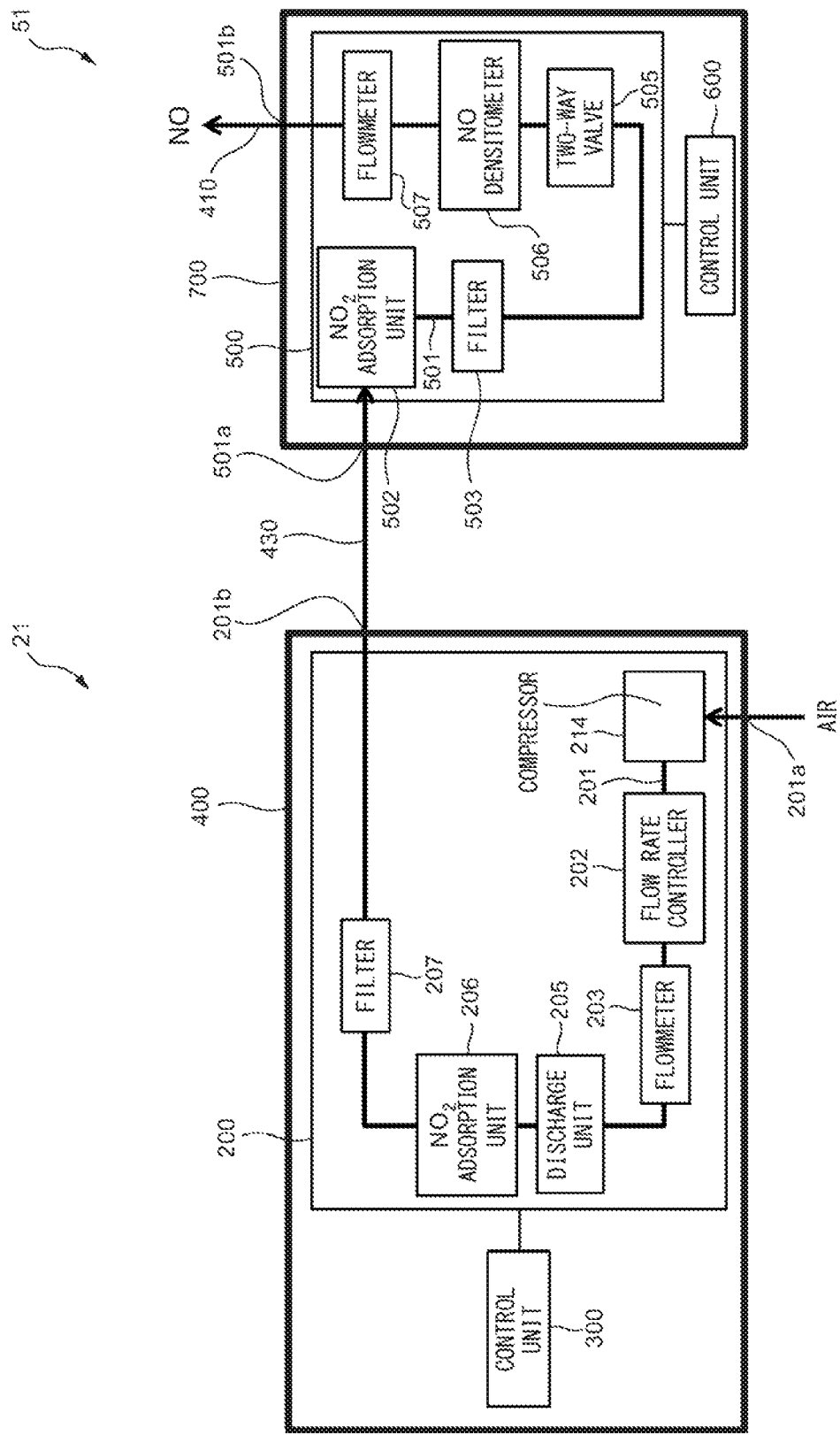
FIG. 21 is a schematic view of another nitric oxide administration device and relay administration device.

FIG. 21 is a schematic view of another nitric oxide administration device 21 and a relay administration device 51. The relay administration device 51 differs as compared to the relay administration device 50 shown in FIG. 20 in that it comprises a flowmeter 507 in the third flow path 501 downstream of the NO densitometer 506 in place of not comprising the pressure gauge 504. By including a flowmeter 507, the dosage can be appropriately controlled. It should be noted that, together with the flowmeter 507, the pressure gauge 504 may be provided.

The relay administration devices shown in FIGS. 20 and 21 described above comprise an NO concentration measurement unit, a flowmeter or pressure gauge, a control unit which calculates the dosage of NO to be administered to the patient based on the NO concentration measured by the NO concentration measurement unit and the value of the flowmeter or the pressure gauge, an adjustment valve which is configured to increase the flow rate when the calculated dosage is less than a predetermined value and reduce the flow rate when the calculated dosage is larger than a predetermined value. The adjustment valve may supply NO when the patient inhales and stop the supply of NO when the patient exhales.

According to the relay administration devices shown in FIGS. 20 and 21 described above, the common effect wherein the dosage of NO can be adjusted is exhibited. By further providing an $NO_2$ adsorption unit, the common effect wherein the $NO_2$ inhaled by the patient is reduced is exhibited. In particular, the relay administration device can be used in connection with an arbitrary nitric oxide administration device which supply NO generated from air as well as the nitric oxide administration devices shown in FIGS. 20 and 21 described above. Further, the relay administration device may separately have an outlet for discharging excess gas containing NO which is not administered to the patient. A removal unit for removing NO or $NO_2$ in the excess gas may be further provided. Though the nitric oxide administration devices shown in FIGS. 20 and 21 do not comprise the oxygen generation unit 100, an oxygen generation unit 100 may be provided, like the nitric oxide administration device 1 shown in FIG. 1, etc.

The nitric oxide administration device and the relay administration device can be configured as a nitric oxide administration system as a whole. In this case, the nitric oxide administration system comprises a nitric oxide administration device comprising a second flow path 201 and an NO generation unit 200 including a discharge unit 205, a relay administration device having a third flow path 501, an extension tube 430, a cannula 410, a respiration detection unit for detecting respiration of the patient, i.e., a respiration detection device. The relay administration device is arranged in the third flow path 501 and further includes a two-way valve, i.e., an adjustment valve, for adjusting the dosage of NO by controlling the opening and opening time in response to patient respiration detected by the respiration detection device.

The NO densitometer of the relay administration device may be arranged downstream of the discharge unit 205 of the nitric oxide administration device rather than the relay administration device. In this case, the opening and opening time of the two-way valve 505 may be controlled in accordance with the NO concentration measured by the NO densitometer arranged in the nitric oxide administration device. Furthermore, the opening and the opening time of the two-way valve 505 may be controlled in accordance with a predetermined NO concentration or the length of the extension tube 430 connected thereto. In order to set or change the various control parameters of the nitric oxide administration device and the relay administration device, the system may comprise the input interface described above, which prompts to input or causes the user to select a flow path specification of the extension tube 430.

Figure 22:
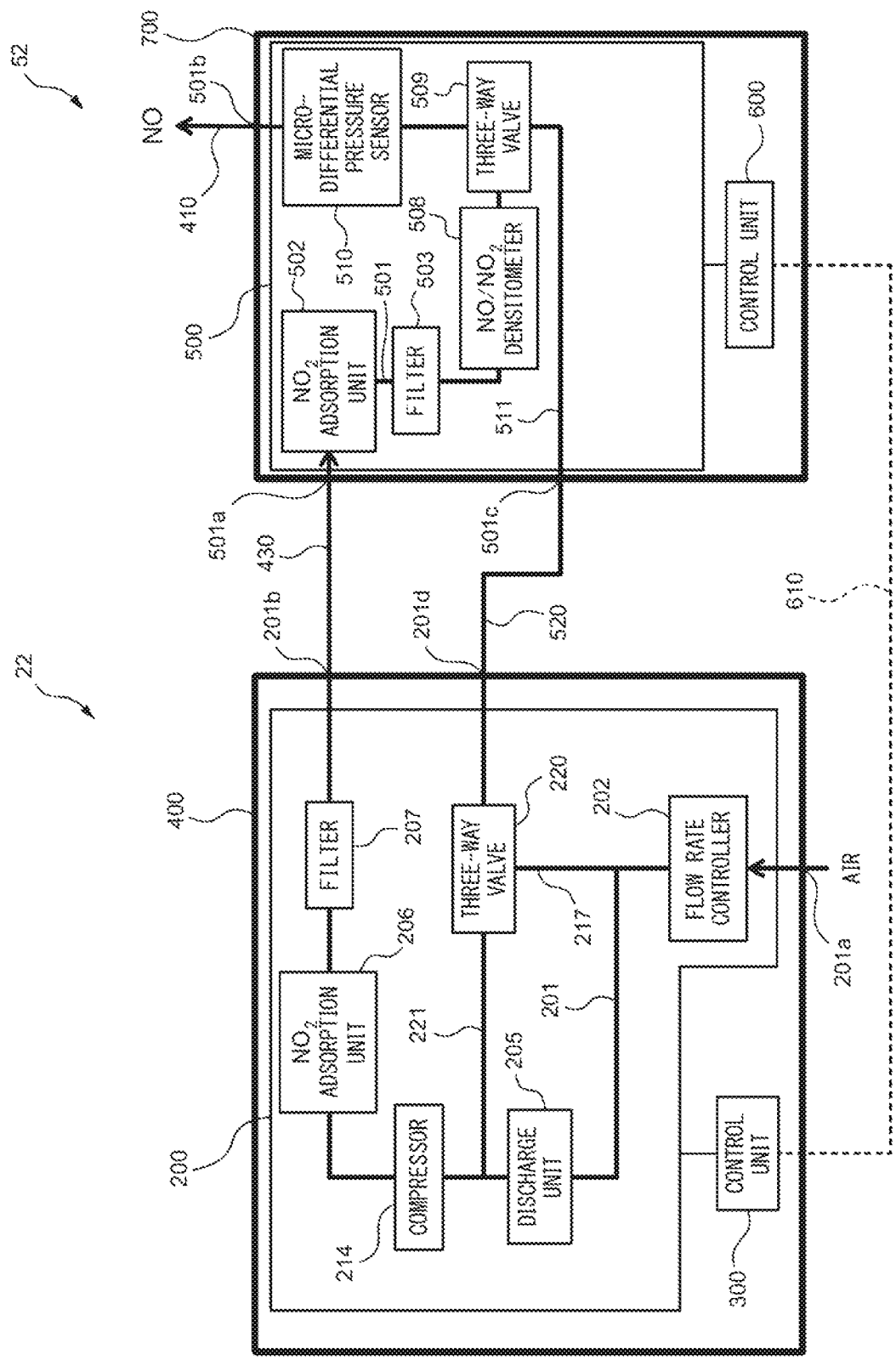
FIG. 22 is a schematic view of yet another nitric oxide administration device and relay administration device.
Figure 23:
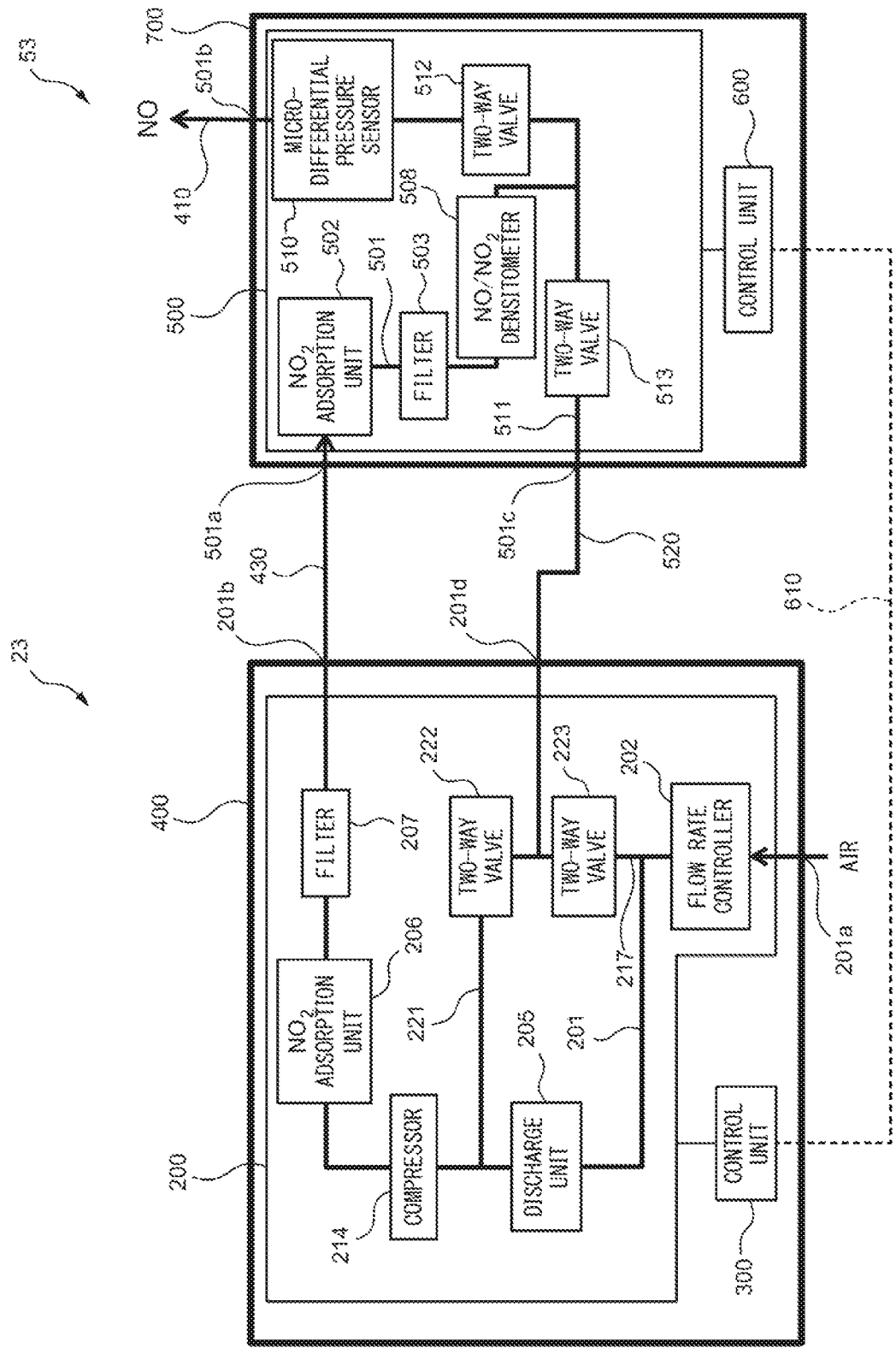
FIG. 23 is a schematic view of yet another nitric oxide administration device and relay administration device.
Figure 24:
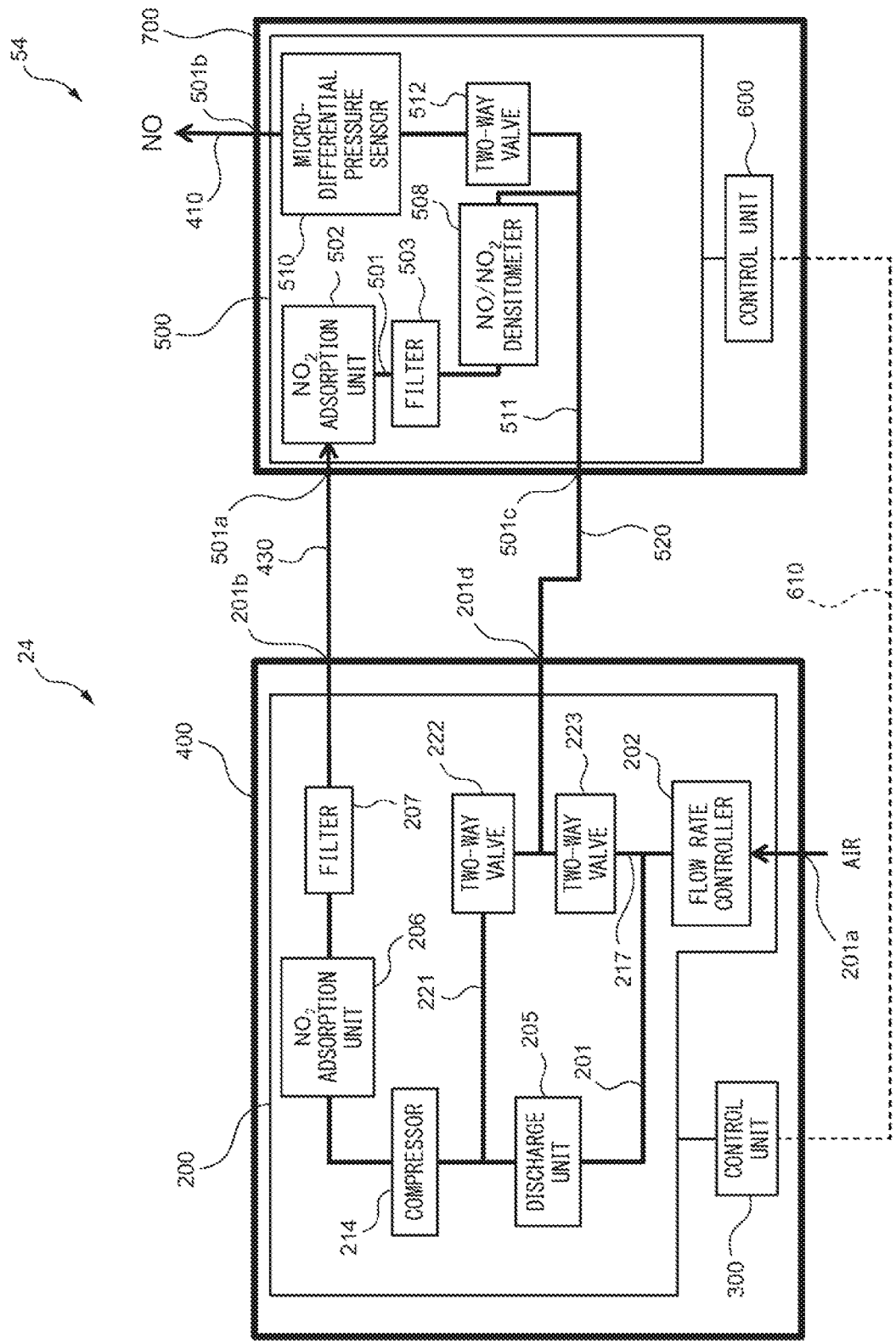
FIG. 24 is a schematic view of yet another nitric oxide administration device and relay administration device.

FIG. 22 is a schematic view of yet another nitric oxide administration device 22 and relay administration device 52, FIG. 23 is a schematic view of yet another nitric oxide administration device 23 and relay administration device 53, and FIG. 24 is a schematic view of yet another nitric oxide administration device 24 and relay administration device 54. The nitric oxide administration devices and the relay administration devices shown in FIGS. 22 to 24 differ as compared to the nitric oxide administration devices and the relay administration devices shown in FIGS. 20 and 21, as a whole, in that gas is refluxed from the relay administration device to the nitric oxide administration device by providing a bypass flow path. Specifically, the nitric oxide administration devices shown in FIGS. 22 to 24 differ as compared to the nitric oxide administration devices shown in FIGS. 14 to 19 in that they comprise a relay administration device and gas is refluxed from the relay administration device to the nitric oxide administration device via a bypass flow path. Thus, the nitric oxide administration devices and relay administration devices shown in FIGS. 22 to 24 have both the advantages of the relay administration device described above and the advantages of reflux through the bypass flow path.

The nitric oxide administration device 22 shown in FIG. 22 comprises a second flow path 201 including the intake port 201a and the NO supply port 201b, the NO generation unit 200 arranged in the second flow path 201 which generates NO from air introduced via the intake port 201a, the control unit 300, and the housing 400. The NO generation unit 200 and the control unit 300 are housed within the housing 400. The various operations of the NO generation unit 200 are controlled by the control unit 300.

The NO generation unit 200 comprises, in the second flow path 201, the flow rate controller 202 arranged downstream of the intake port 201a, the discharge unit 205 arranged downstream of the flow rate controller 202, the compressor 214 arranged downstream of the discharge unit 205, the $NO_2$ adsorption unit 206 arranged downstream of the compressor 214, the filter 207 described above arranged downstream of $NO_2$ adsorption unit 206, and the three-way valve 220 for selectively switching between the second flow path 201 upstream of the discharge unit 205 and the second flow path 201 downstream of the discharge unit 205.

The upstream side of the relay administration device 52 is connected to the NO supply port 201b via the extension tube 430, and the downstream side of the relay administration device 52 is connected to the upstream end of the cannula 410. The relay administration device 52 comprises the third flow path 501 including an upstream connection end 501a and the downstream connection end 501b, the dosage adjustment unit 500 arranged in the third flow path 501 for adjusting the dosage of the gas introduced via the upstream connection end 501a, the control unit 600, and the housing 700.

The gas adjusted by the dosage adjustment unit 500 is supplied via the downstream side connection end 501b. The various operations of the dosage adjustment unit 500 are controlled by the control unit 600. A communication path 610 is established between the control unit 300 of the nitric oxide administration device 22 and the control unit 600 of the relay administration device 52 by wire or wirelessly. The relay administration device 52 is connected to a power supply via a power cable (not illustrated). However, the relay administration device 52 may have a battery which can be housed in the interior of the housing 700, which may serve as the power source. In place of the control unit 600, the nitric oxide administration device 22 and the relay administration device 52 may be electrically connected, and the various operations of the dosage adjustment unit 500 may be controlled by the control unit 300.

The relay administration device 52 comprises, in the third flow path 501, the $NO_2$ adsorption part 502 arranged downstream of the upstream connection end 501a, the filter 503 arranged downstream of the $NO_2$ adsorption part 502, the $NO/NO_2$ densitometer 508 arranged downstream of the filter 503, a three-way valve 509 arranged downstream of the $NO/NO_2$ densitometer 508, and a micro-differential pressure sensor 510 arranged downstream of the three-way valve 509. Further, in the third flow path 501, the bypass flow path 511 branched from the three-way valve 509 extends to the bypass upstream side connection end 501c. In the third flow path 501, the flow path to the downstream side connection end 50) b and the flow path to the bypass upstream side connection end 501c are selectively switched by the three-way valve 509. The bypass upstream connection end 501c of the relay administration device 52 is connected to the bypass downstream side connection end 201d of the nitric oxide administration device 22 via the bypass tube 520. The second flow path 201 extending from the bypass downstream side connection end 201d is connected to the three-way valve 220. The three-way valve 509 constitutes a first flow path switching unit for switching the opening and closing of the flow path from at least downstream of the $NO_2$ removal unit to the cannula 410. Furthermore, the three-way valve 220 constitutes a second flow path switching unit.

As described above, when the gas containing NO is not immediately administered to the patient downstream of $NO_2$ adsorption unit 502 of the relay administration device 52, the three-way valve 509 is switched, and the third flow path 501 and the second flow path 201 communicate with each other via the bypass tube 520. Specifically, by switching the three-way valve 509, the gas of the relay administration device 52 can be refluxed to the nitric oxide administration device 22. At this time, the fluctuations in the concentrations of NO and $NO_2$ are small, and when the generation of further NO is not necessary, the three-way valve 220 is switched, and the second flow path 201 downstream of the discharge unit 205 communicates via the bypass flow path 221. By refluxing to downstream of the discharge unit 205, the reflux path can be shortened. Conversely, if further NO generation is required, the three-way valve 220 is switched, and the second flow path 201 upstream of the discharge unit 205 communicates via the bypass flow path 217.

The nitric oxide administration device 23 and the relay administration device 53 differ as compared to the nitric oxide administration device 22 and the relay administration device 52 shown in FIG. 22 in that there are provided two two-way valves, i.e., the two-way valve 222 and the two-way valve 223 in place of the three-way valve 220, and there are provided two other two-way valves, i.e., the two-way valve 512 and the two-way valve 513 in place of the three-way valve 509.

Specifically, in the nitric oxide administration device 23, the second flow path 201 extending from the bypass downstream side connection end 201d communicates with the flow path between the two-way valve 222 and the two-way valve 223. As a result, the second flow path 201 extending from the bypass downstream side connection end 201d can not only selectively communicate between the second flow path 201 upstream of the discharge unit 205 and the second flow path 201 downstream of the discharge unit 205, but also may not communicate therewith or may communicate therewith. Similarly, in the relay administration device 53, the third flow path 501 extending from the upstream connection end 501a communicates with the flow path between the two-way valve 512 and the two-way valve 513. As a result, the third flow path 501 extending from the upstream connection end 501a can not only selectively communicate between the flow path to the downstream side connection end 501b and the flow path to the bypass upstream connection end 501c, but also may not communicate therewith or may communicate therewith. The two-way valve 512 and the two-way valve 513 constitute a first flow path switching unit for switching the opening and closing of the flow path from at least downstream of the $NO_2$ removal unit to the cannula 410. Furthermore, the two-way valve 222 and the two-way valve 223 constitute a second flow path switching unit.

The nitric oxide administration device 24 and the relay administration device 54 differ as compared to the nitric oxide administration device 23 and the relay administration device 53 shown in FIG. 23 only in that they do not comprise the two-way valve 513. Since the relay administration device 54 does not comprise the two-way valve 513, the gas of the relay administration device 52 can always be refluxed to the nitric oxide administration device 22 regardless of the opening and closing of the two-way valve 512. The two-way valve 512 constitutes a first flow path switching unit. Furthermore, the two-way valve 222 and the two-way valve 223 constitute a second flow path switching unit. By constituting the first flow path switching unit from one two-way valve 512, the flow path itself for reflux between the third flow path 501 and the second flow path 201 via the bypass tube 520 can function as a buffer tank. As a result, when the gas in the relay administration device 54 is administered to the patient by opening the two-way valve 513, since the gas in the reflux flow path is also released simultaneously, the administration time can be shortened.

It should be noted that the configuration in which the two three-way valves are each replaced with two two-way valves, as described with reference to FIG. 23, and the configuration in which the three-way valve on the upstream side is replaced with two two-way valves, the three-way valve on the downstream side is replaced with one two-way valve, and the flow path always refluxes to the flow path on the upstream side, as described with reference to FIG. 24, can also be applied to the nitric oxide administration devices shown in FIGS. 14 to 19. Specifically, the first flow path switching unit may be composed of one three-way valve or one or two two-way valves, and the second flow path switching unit may be composed of one three-way valve or two two-way valves. In particular, only the three-way valve 216 may be omitted in the nitric oxide administration device 17 shown in FIG. 17. As a result, the gas of the nitric oxide administration device 17 can always be refluxed regardless of the opening and closing of the two-way valve 218 arranged upstream of the NO supply port 201b. In this case, the two-way valve 218 arranged upstream of the NO supply port 201b constitutes a first flow path switching unit for switching the opening and closing of the flow path from downstream of the $NO_2$ removal unit to the supply port. Furthermore, it is preferable that at least one of the nitric oxide administration device and the relay administration device have an $NO_2$ removal unit for removing $NO_2$. Specifically, the relay administration device may not have an $NO_2$ removal unit.

When the nitric oxide administration device and the relay administration device compose a single nitric oxide administration system as a whole, the nitric oxide administration system comprises a flow path for refluxing upstream of the $NO_2$ removal unit, and the relay administration device comprises a first flow path switching unit for switching the opening and closing of the flow path from downstream of the $NO_2$ removal unit to the cannula. The first flow path switching unit corresponds to the adjustment valve described above.

As described above, switching of the first flow path switching unit, or switching of the first flow path switching unit and the second flow path switching unit, i.e., reflux, is intermittently performed at a predetermined timing. However, reflux may be performed in synchronization with the respiration of the patient. In this case, the respiration of the patient is detected by a micro-differential pressure sensor, for example, the micro-differential pressure sensor 510, and switching of the first flow path switching unit or switching of the first flow path switching unit and the second flow path switching unit can be performed. The micro-differential pressure sensor may be used to control the discharge unit 205. This will be described below with reference to FIG. 14.

At least at the time of administration, i.e., in response to administration to the patient, air is introduced from the intake port 201a and air drawing is performed. Specifically, the three-way valve 213 and the three-way valve 216 are switched so as to close the bypass flow path 217, and the compressor 214 or the flow controller 202 is controlled so that more air is drawn. As a result, decreases in pressure and flow rate in the flow path during administration can be alleviated, whereby the administration time can be shortened. Furthermore, at least at the time of administration, i.e., depending on administration to the patient, discharge by the discharge unit 205 is performed. By performing discharge in conjunction with the introduction of air, fluctuations in the concentration of NO can be suppressed, whereby gas having a more stable NO concentration can be administered in a short time.

At the time of administration or air drawing, the discharge of the discharge unit 205 is controlled by the control unit 300 so that more NO is generated as compared with other times. Specifically, more NO can be generated by increasing the frequency of discharge (frequency, i.e., the number of discharges per unit time), increasing the energy per discharge (one pulse) (current and voltage), increasing the discharge time per discharge, increasing the total number of discharges per administration, or increasing the number of electrodes for discharge. Conversely, other than at the time of administration or other than at the time of air drawing, a discharge to compensate for decreases in the NO concentration over time, i.e., for maintaining the NO concentration, may be performed. Naturally, the amount of NO generation at the time of administration is greater than the amount of NO generation at the time of administration other than at the time of administration or at the time of air drawing. Furthermore, at the time of administration or at the time of air drawing, the NO concentration is stabilized by determining the amount of NO to be generated in accordance with the amount of air drawing from the intake port 201a.

The intake of air from the intake port 201a is controlled in synchronism with the respiration of the patient detected by the micro-differential pressure sensor, i.e., in synchronism with administration. Specifically, by increasing the amount of air drawn at the time of administration, decreases in pressure in the flow path can be alleviated, whereby the administration time can be shortened. Further, the residence time of the gas can be shortened by reducing the amount of air drawn and increasing the reflux when the gas is not administered. As a result, increases in $NO_2$ concentration can be suppressed. In order to increase the reflux rate, the three-way valve 213 and the three-way valve 216 are switched so as to open the bypass flow path 217.

Thus, the closing and opening of the bypass flow path 217 is performed in synchronization with the respiration of the patient detected by the micro-differential pressure sensor, and in response, the control of the compressor 214 or the flow controller 202 and the control of the discharge unit 205 are performed.

Depending on the length of the cannula 410 and the presence or absence of the relay administration device, the volume of the entire flow path increases, and as a result, the time during which the gas is resident in the flow path increases. As a result, there is a risk that the concentration of NO will be reduced by the generated NO and oxygen reacting to become $NO_2$. To compensate for this, control is performed to increase the overall generation amount of NO or to reduce the residence time of the gas in the flow path. In particular, in order to reduce the residence time of the gas in the flow path, the flow rate of a portion of the flow path between at least the discharge unit 205 and the outlet of the cannula 410, preferably, the flow rate of the entire flow path, is increased by increasing the rotation speed of the compressor 214 or control is performed by the flow controller 202 in such a manner that the amount of air drawn is reduced at the time of reflux and increased at the time of non-reflux, i.e., administration. As a result, even if the volume of the entire flow path increases, since the residence time of the gas from the discharge unit 205 to the outlet of the cannula 410 is maintained constant, there is an advantage in that the amount of NO generated can be made constant before and after the volume increase of the entire flow path. Conversely, when the residence time increases even when the reflux amount is increased, it can be further compensated by increasing the amount of NO generation. Furthermore, when the dosage to the patient increases, the dosage per administration is increased or the NO concentration at the time of administration is increased. In this case, it is desirable that the concentration of $NO_2$ in the flow path not be increased so that the amount of $NO_2$ administered to the patient does not increase. Thus, as described above, in order to reduce the residence time of the gas in the flow path, the flow rate of a portion of the flow path between at least the discharge unit 205 and the outlet of the cannula 410 is increased, or preferably, the flow rate of the entire flow path is increased to increase the reflux rate.

In short, the discharge by the discharge unit 205 is performed so as to generate NO corresponding to the volume of the entire flow path. Furthermore, the residence time of the gas is determined in accordance with the volume of the entire flow path. The residence time of the gas is determined in accordance with the dosage to the patient.

Figure 25:
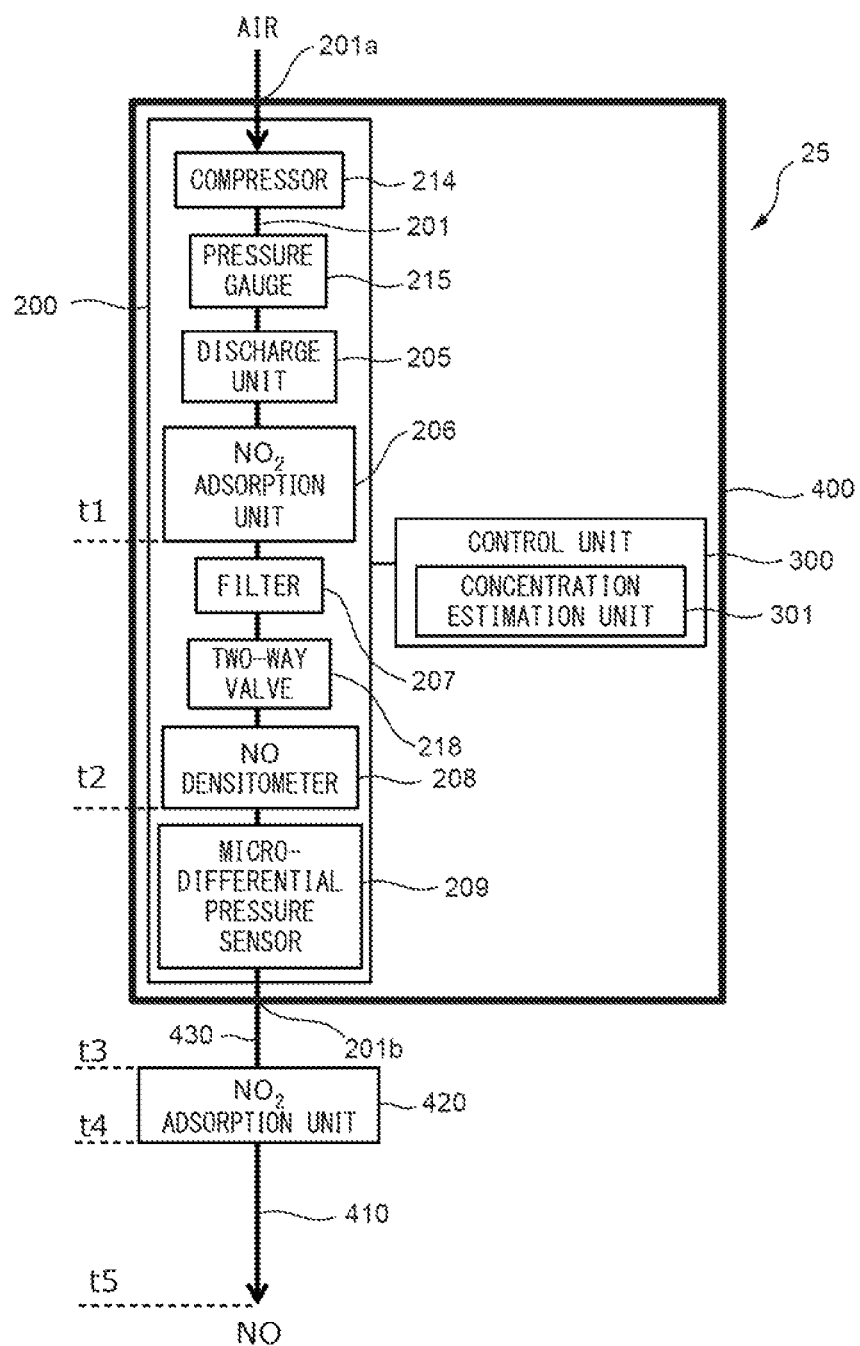
FIG. 25 is a schematic view of yet another nitric oxide administration device.

FIG. 25 is a schematic view of yet another nitric oxide administration device 25.

The nitric oxide administration device 25 comprises the second flow path 201 including the intake port 201a and the NO supply port 201b, the NO generation unit 200 arranged in the second flow path 201 and which generates NO from air introduced via the intake port 201a, the control unit 300, and the housing 400. The NO generation unit 200 and the control unit 300 are housed in the interior of the housing 400. The NO generated by the NO generation unit 200 is supplied via the NO supply port 201b. The various operations of the NO generation unit 200 are controlled by the control unit 300.

The NO generation unit 200 includes, in the second flow path 201, the compressor 214 as an air compressor arranged downstream of the intake port 201a, the pressure gauge 215 arranged downstream of the compressor 214, the discharge unit 205 described above arranged downstream of the pressure gauge 215, the $NO_2$ adsorption unit 206 described above arranged downstream of the discharge unit 205, the filter 207 described arranged downstream of the $NO_2$ adsorption unit 206, the two-way valve 218 arranged downstream of the filter 207, the NO densitometer 208 arranged downstream of the two-way valve 218, and the micro-differential pressure sensor 209 arranged downstream of the NO densitometer 208. A two-way valve may be replaced with another type of adjustment valve capable of adjusting flow rate.

The nitric oxide administration device 25 further comprises an $NO_2$ adsorption unit 420. The upstream side of the $NO_2$ adsorption unit 420 is connected to the NO supply port 201b via an extension tube 430, and the downstream side of the $NO_2$ adsorption unit 420 is connected to the upstream end of the cannula 410.

Though the length of the flow path of the gas flowing inside the nitric oxide administration device 25, i.e., the second flow path 201, is generally constant, the length of the flow path of the gas flowing outside the nitric oxide administration device 25, i.e., the length of the cannula 410, including the cannula connected to the nitric oxide administration device, i.e., the extension tube 430, is variable, depending on the environment of use of the nitric oxide administration device, etc. The longer the cannula, the longer NO and oxygen can react, whereby more $NO_2$ can be generated. Thus, a method for estimating the concentrations of NO and $NO_2$ at the actual point of administration, considering the cannula length, will be described below.

The control unit 300 of the nitric oxide administration device 25 comprises a concentration estimation unit 301 for estimating the concentrations of NO and $NO_2$ at a predetermined position based on the oxygen concentration, the NO concentration measured by the NO densitometer 208, which is an NO concentration measurement unit, and the residence time of the gas between $NO_2$ adsorption unit 206 and the predetermined position.

To estimate the concentrations, the following prerequisites are set. First, the $NO_2$ adsorption unit 206 and $NO_2$ adsorption unit 420 have the capability to adsorb all of the $NO_2$ in the flowing gas, thus zeroing the concentration of $NO_2$ in the gas immediately after passage. Specifically, the $NO_2$ adsorption unit 206 and the $NO_2$ adsorption unit 420 are designed to have such sufficient adsorption capability, or alternatively, the concentration estimating portion 301 estimates that the concentration of $NO_2$ in the gases is zero. At this time, as actions of the $NO_2$ adsorption unit 206 and the $NO_2$ adsorption unit 420, an amount of NO equal to that of the adsorbed $NO_2$ is reduced as compared with that in gas.

To calculate the residence time of the gas, the flow path specification such as the volume of the interior of the nitric oxide administration device 25 (in particular, between the $NO_2$ adsorption unit 206 and the NO densitometer 208 and between the $NO_2$ adsorption unit 206 and the NO supply port 201b) is known. In continuous flow mode, the residence time is determined by dividing the flow path volume by the flow rate. In the synchronized flow mode, the residence time is determined by dividing the flow path volume by the flow rate obtained by multiplying one dose by the respiratory rate per minute or unit time. In the continuous flow mode and the synchronized flow mode, for example, a table based on the operating state of the compressor 214 or the relationship between the output value of the pressure gauge 215 or the micro-differential pressure sensor 209 and the measured value of the flowmeter may be prepared in advance, and the residence time may be determined by referring to or correcting the table.

The acceptable value (limit value) of $NO_2$ administered to the patient is set to a predetermined value, for example, 0.5 ppm or less. Further, the NO generated by the discharge unit 205 is a very small amount, for example, 100 ppm, and the $NO_2$, which is the main by-product at the extent of discharge, is approximately 10% of the NO generation amount. Thus, oxygen which is reduced when NO is generated from air by discharging, and oxygen which is reduced when $NO_2$ is generated by reacting with NO are very trace amounts. Thus, since the change in the concentration of oxygen in the gas can be ignored, the concentration of oxygen is set to a value of the oxygen concentration in the atmosphere which is generally known, for example, 21%. It should be noted that an oxygen concentration measurement unit may be arranged to measure the oxygen concentration in at least one location in the flow path, and the value thereof may be used as a concentration at an arbitrary point of the flow path.

In the use of the nitric oxide administration device 25, in the continuous flow mode, the history of the flow rate is maintained. In the use of the nitric oxide administration device 25, in the synchronized flow mode which is synchronized with the respiration of the patient, the histories of a single-dosage, dosage time, and dosage interval (awaiting inhalation) time are maintained. The single-dosage may be calculated from the opening time of the two-way valve 218, or the pressure fluctuations measured by the pressure gauge 215, etc. Furthermore, the nitric oxide administration device 25 may comprise the flowmeter 203, and in this case, the single-dosage may be calculated from an instantaneous flow rate. The history of the NO concentration measured by the NO densitometer 208 is maintained.

From the reaction rate equation of the chemical reaction, k is set as the reaction rate constant, and the concentration Y ppm of NO after a lapse of a predetermined time, i.e., after a lapse of t minutes, is calculated from the following formula (1). Similarly, the concentration X ppm of $NO_2$ after a lapse of a predetermined time, i.e., after a lapse of t minutes is calculated from the following formula (2). It should be noted that the reaction rate constant is determined in advance by experimentation, etc.

[Math 1]

$$Y[\text{ppm}] = \frac{1}{\frac{1}{[NO(\text{ppm})]_{t=0}} + 2k \times [O_2(\%)] \times t} = \frac{1}{\frac{1}{[NO(\text{ppm})]_{t=0}} + 1.707 \times 10^{-5} \times [O_2(\%)] \times t} \quad \text{formula (1)}$$

[Math 2]

$$X[\text{ppm}] = \frac{[NO(\text{ppm})]_{t=0} \times t}{t + \frac{1}{2k \times [NO(\text{ppm})]_{t=0} \times [O_2(\%)]}} = \frac{[NO(\text{ppm})]_{t=0} \times t}{t + \frac{1}{1.707 \times 10^{-5} \times [NO(\text{ppm})]_{t=0} \times [O_2(\%)]}} \quad \text{formula (2)}$$

Based on the above conditions and formulas, at time t=t5, the steps of estimating the concentrations of NO and $NO_2$ at the outlet of cannula 410 of gas Gt5 passing through the outlet of cannula 410 will be described.

First, from the flow path specification and the history of the flow rate, the time t1 when the gas Gt5 leaves the $NO_2$ adsorption unit 206, the time t2 when the gas Gt5 leaves the NO densitometer 208, the time 3 when the gas Gt5 enters the $NO_2$ adsorption unit 420, the time t4 when the gas Gt5 leaves the $NO_2$ adsorption unit 420, and the time t5 when the gas passes through the outlet of the cannula 410 are calculated. Specifically, in the synchronized flow mode, when the current time t=t5, the sum of the most recent dosages up to time t5 is calculated, and the number of repetitions of administration N1 corresponding to the volume between the $NO_2$ adsorption unit 206 and the outlet of the cannula 410 is calculated. The time t1 when the gas Gt5 leaves the $NO_2$ adsorption unit 206 is calculated from the number of repetitions of administration N1, and the histories of the time of administration and the administration interval time. In the same manner, the times t2 to t4 can be obtained. Conversely, in the case of continuous flow mode, times t1 to t4 can be calculated from the integrated value of the latest flow rate to time t and the time when the volumes between the outlet of the cannula 410 and each point coincide.

At the current time t, in the case in which the gas has not reached the outlet of the cannula 410, i.e., in the case in which the current time t<t5, the time of each upstream point through which the gas has already passed and the time of each point through which the gas will pass can be calculated. Specifically, in the synchronized flow mode, the time of each upstream point through which the gas has already passed can be determined, as in the case of the time t=t5, based on the histories of the volume up to the each upstream point from the dosage up to the current time t, the administration time and the administration interval time, and the current position to the upstream point. Regarding each downstream point through which the gas will pass and the time t5 when the gas leaves the outlet of the cannula 410, for example, the average flow rate can be calculated based on the administration time, the administration interval time, and the dosage within a predetermined time, and can be calculated by dividing the volume from the current position to each point downstream by the average flow rate. Conversely, in continuous flow mode, the time of each upstream point though which the gas has already passed can be calculated, as in the case of the time t=t5, as the time when the integrated value of the current flow rate up to time t, and the volume between the current position and the each point match. Regarding each downstream point through which the gas will flow and the time t5 when the gas leaves the outlet of the cannula 410, for example, it can be calculated by calculating the average flow rate within a predetermined time and dividing the volume from the current position to each point of the downstream by the average flow rate. When calculating the time of each upstream point, rather than calculating the time actually lapsed from the sum of the most recent dosage, the average flow rate is calculated based on the administration time, the administration interval time, and the dosage within the predetermined time, and may be calculated by dividing the volume from the current position to each upstream point by the average flow rate.

Then, the NO concentration y1 of the gas Gt5 at time t1 is estimated as an inverse problem from the oxygen concentration (e.g., 21%), the maintained NO concentration history, the residence time (t2−t1) of the gas Gt5 between the $NO_2$ adsorption unit 206 and the NO densitometer 208, and formula (1).

The NO concentration y3 and the $NO_2$ concentration x3 at time t3 when the gas Gt5 has flowed into the $NO_2$ adsorption unit 420 are then estimated as direct problems from the residence time (t3−t1) between the $NO_2$ adsorption unit 206 and the $NO_2$ adsorption unit 420, the oxygen concentration, the NO concentration y1 of the gas Gt5 at the estimated time t1, and formulas (1) and (2). It should be noted that the NO concentration y3 may be estimated using the residence time (t3−t2) between the NO densitometer 208 and the $NO_2$ adsorption unit 420 and the maintained NO concentration history.

The NO concentration y4 and the $NO_2$ concentration x4 at time t4 when the gas Gt5 leaves from the $NO_2$ adsorption unit 420 are then estimated. As described above, in the $NO_2$ adsorption unit 420, all of the $NO_2$ in the gas Gt5 is adsorbed and an equal amount of NO is reduced. When the time (t4−t3) required for passage inside the $NO_2$ adsorption unit 420 is long, for example, an $NO_2$ concentration generated during passage may be estimated from the NO concentration y3 immediately before passage, the oxygen concentration, the time (t4−t3) required for passage, and the equation (2), and a part or all of the $NO_2$ may be adsorbed. Similarly, NO may be adsorbed in an amount equal to the $NO_2$ generated and adsorbed during passage.

Next, the NO concentration y and the $NO_2$ concentration x at the outlet of the cannula 410 are estimated from the NO concentration y4 and $NO_2$ concentration x4 at time t4 when the gas Gt leaves the $NO_2$ adsorption unit 420, the oxygen concentration, the residence time (t−t4) between the $NO_2$ adsorption unit 420 and the outlet of the cannula 410, and formulas (1) and (2) as direct problems.

Depending on the estimated NO concentration y and the $NO_2$ concentration x at the outlet of the cannula 410, the discharge parameters of the discharge unit 205 may be changed so as to increase or decrease the NO concentration y, or stoppage may be performed when an abnormality occurs in the value of the NO concentration y or $NO_2$ concentration x. In continuous flow mode, for example, the output of the compressor 214 or the opening or opening time of the two-way valve 218 may be adjusted to adjust the dosage of the gas to match the prescribed amount. In synchronized flow mode, the single-dosage of gas may be adjusted to match the prescribed amount.

In the nitric oxide administration device 25, the $NO_2$ adsorption unit 420 may be omitted. Furthermore, in the case of continuous flow mode, the nitric oxide administration device 25 may comprise a flowmeter instead of the pressure gauge 215, and the two-way valve 218 and the micro-differential pressure sensor 20) may be omitted. The nitric oxide administration device 25 may comprise a flowmeter in addition to the pressure gauge 215 in the case of synchronized flow mode. This facilitates calculation of the single-dose.

Figure 26:
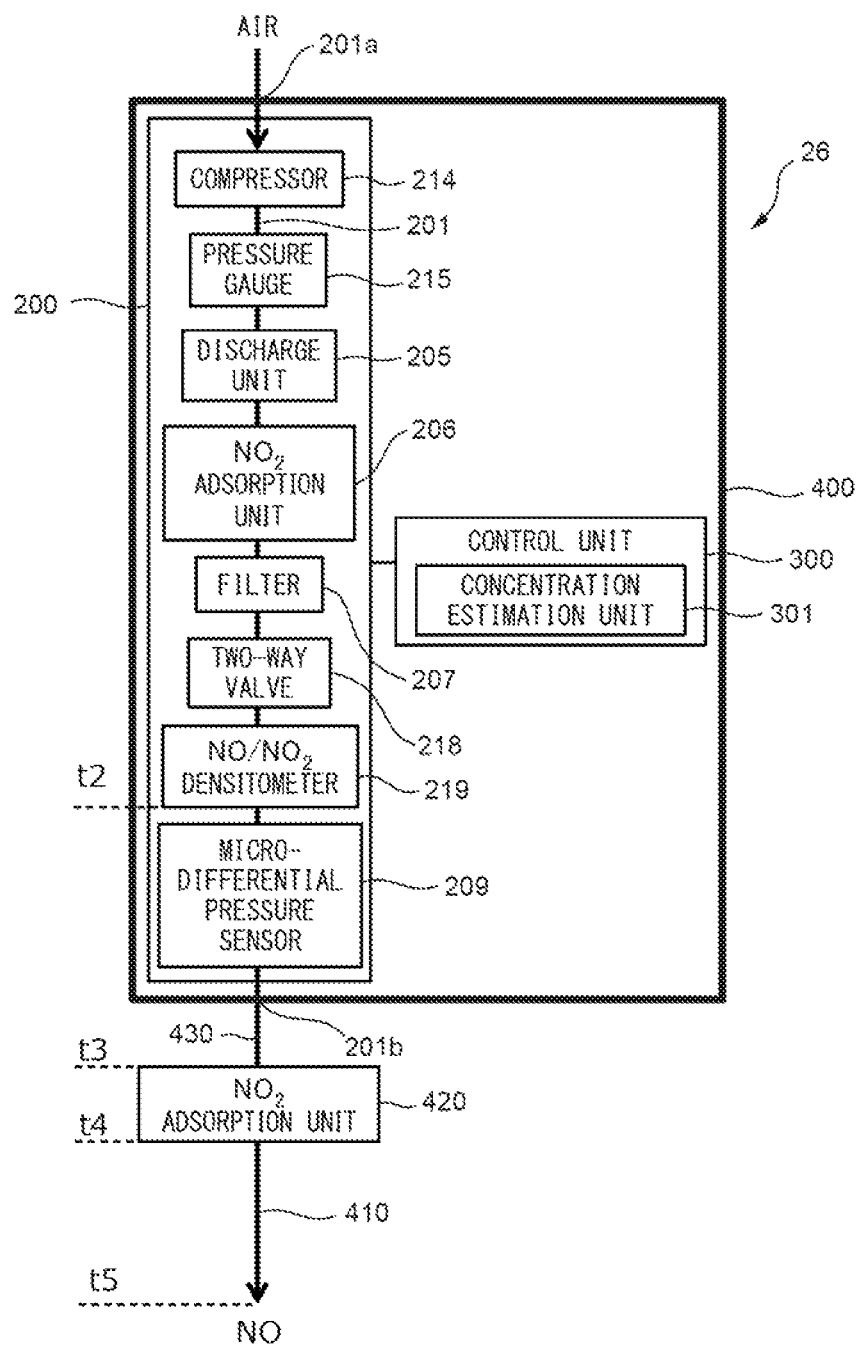
FIG. 26 is a schematic view of yet another nitric oxide administration device.

FIG. 26 is a schematic view of yet another nitric oxide administration device 26. The nitric oxide administration device 26 differs as compared to the nitric oxide administration device 25 shown in FIG. 25 only in that it comprises an $NO/NO_2$ densitometer 219 in place of the NO densitometer 208. As explained with reference to FIG. 25, another method for estimating the concentrations of NO and $NO_2$ at the actual point of administration, also considering the cannula length, is described below.

To estimate the concentrations, the following prerequisites are set. To calculate the residence time of the gas, a flow path specification such as the volume of the interior of the nitric oxide administration device 26 (in particular, between the $NO/NO_2$ densitometer 219 and the NO supply port 201b) is known. In addition, the acceptable value (limit value) of $NO_2$ administered to the patient is set to a predetermined value, for example, 0.5 ppm or less. Furthermore, NO generated by the discharge unit 205 is a very small amount, e.g., 100 ppm, and the $NO_2$, which is a main by-product, at the extent of discharge is approximately 10% of the NO generation amount. Thus, oxygen which is reduced when NO is generated from air by discharging, and oxygen which is reduced when $NO_2$ is generated by reacting with NO are very trace amounts. Thus, since the change in the concentration of oxygen in the gas can be ignored, the concentration of oxygen is set to a value of the oxygen concentration in the atmosphere which is generally known, for example, 21%. It should be noted that an oxygen concentration measurement unit may be arranged to measure the oxygen concentration in at least one location in the flow path, and the value thereof may be used as a concentration at an arbitrary point of the flow path. The adsorption characteristics of the $NO_2$ adsorption unit 206 need not be particularly defined in advance. However, as described above, the $NO_2$ adsorption unit 420 has a capability of adsorbing all of the $NO_2$ in the passing gas.

In the use of the nitric oxide administration device 26, in continuous flow mode, the history of the flow rate is maintained. In the use of the nitric oxide administration device 26, in synchronized flow mode, which is synchronized with the respiration of the patient, the histories of the single-dosage, the administration time, and the administration interval (awaiting inhalation) time are maintained. The single-dosage may be calculated from the opening time of the two-way valve 218 and pressure fluctuations measured by the pressure gauge 215, etc. Further, the nitric oxide administration device 26 may comprise the flowmeter 203, and in this case, the single-dosage may be calculated from an instantaneous flow rate. In addition, the histories of the NO concentration and $NO_2$ concentration measured by the $NO/NO_2$ densitometer 219 are maintained.

First, from the flow path specification and the history of the flow rate, the time t2 when the gas Gt5 leaves the $NO/NO_2$ densitometer 219, the time t3 when the gas Gt5 enters the $NO_2$ adsorption unit 420, and the time t4 when the gas Gt5 leaves the $NO_2$ adsorption unit 420 are calculated. Specifically, in synchronized flow mode, when the current time t=t5, the sum of the most recent dosages up to time t5 is calculated, and the administration number N2 corresponding to the volume between the $NO/NO_2$ densitometer 219 and the outlet of the cannula 410 is calculated. The time t2 at which the gas Gt5 leaves the $NO/NO_2$ densitometer 219 is calculated from the administration number N2, and the histories of the administration time and the administration interval time. In the same manner, the times t3 and t4 can be determined. Conversely, in the case of continuous flow mode, times t2 to t4 can be calculated from the time when the integrated value of the latest flow rate up to time t and the volume between the outlet of cannula 410 and each point match.

At the current time t, in the case in which the gas has not reached the outlet of the cannula 410, i.e., in the case in which the current time t<t5, the time of each upstream point through which the gas has already passed and the time of each point through which the gas will pass can be calculated. Specifically, in the synchronized flow mode, the time of each upstream point through which the gas has already passed can be determined, as in the case of the time t=t5, based on the histories of the volume up to the each upstream point from the dosage up to the current time t, the administration time and the administration interval time, and the current position to the upstream point. Regarding each downstream point through which the gas will pass and the time t5 when the gas leaves the outlet of the cannula 410, for example, the average flow rate can be calculated based on the administration time, the administration interval time, and the dosage within a predetermined time, and can be calculated by dividing the volume from the current position to each point downstream by the average flow rate. Conversely, in continuous flow mode, the time of each upstream point though which the gas has already passed can be calculated, as in the case of the time t=t5, as the time when the integrated value of the current flow rate up to time t, and the volume between the current position and the each point match. Regarding each downstream point through which the gas will flow and the time t5 when the gas leaves the outlet of the cannula 410, for example, it can be calculated by calculating the average flow rate within a predetermined time and dividing the volume from the current position to each point of the downstream by the average flow rate. When calculating the time of each upstream point, rather than calculating the time actually lapsed from the sum of the most recent dosage, the average flow rate is calculated based on the administration time, the administration interval time, and the dosage within the predetermined time, and may be calculated by dividing the volume from the current position to each upstream point by the average flow rate.

Then, the NO concentration y3 and $NO_2$ concentration x3 immediately after the gas Gt flows into the $NO_2$ adsorption unit 420 are estimated as direct problems from the residence time (t3–t2) between the $NO/NO_2$ densitometer 219 and the $NO_2$ adsorption unit 420, the oxygen concentration (for example, 21%), the NO concentration y2 and the $NO_2$ concentration x2 of the gas Gt5 at time t2, as well as formulas (1) and (2).

The NO concentration y4 and $NO_2$ concentration x4 at time t4 when the gas Gt5 leaves the $NO_2$ adsorption unit 420 are the estimated. As described above, all of the $NO_2$ in the gas Gt5 is adsorbed in the $NO_2$ adsorption unit 420 and an equal amount of NO is reduced. It should be noted that when the time (t4–t3) required for the gas to pass through the interior of the $NO_2$ adsorption unit 420 is long, for example, the $NO_2$ concentration generated during the passage may be estimated from the NO concentration y3 immediately before passage, the oxygen concentration, the time required for the passage (t4–t3), and formula (2), and a part or all of the $NO_2$ may be adsorbed. Similarly, NO may be adsorbed in an amount equal to the $NO_2$ generated and adsorbed during passage.

Next, the NO concentration y and the $NO_2$ concentration x at the outlet of the cannula 410 are estimated from the NO concentration y4 and $NO_2$ concentration x4 at the time 4 when the gas Gt5 leaves the $NO_2$ adsorption unit 420, the oxygen concentration, the residence time (t-t4) between the $NO_2$ adsorption unit 420 and the outlet of the cannula 410, and formulas (1) and (2) as direct problems.

Depending on the estimated NO concentration y and the $NO_2$ concentration x at the outlet of the cannula 410, the discharge parameters of the discharge unit 205 may be changed so as to increase or decrease the NO concentration y, or stoppage may be performed when an abnormality occurs in the value of the NO concentration y or the $NO_2$ concentration x. In continuous flow mode, for example, the output of the compressor 214 or the opening or opening time of the two-way valve 218 may be adjusted to adjust the dosage of the gas to match the prescribed amount. In synchronized flow mode, the single-dose of gas may be adjusted to match the prescribed amount.

According to the nitric oxide administration devices shown in FIGS. 25 and 26 described above, the common effect wherein the concentrations of NO and $NO_2$ can be estimated is exhibited. Furthermore, the concentrations of NO and $NO_2$ can be estimated in the same manner in predetermined positions other than the outlet of the cannula 410. For example, the concentration estimation unit 301 of the control unit 300 may have an input interface that prompts to input or causes the user to select the flow path specification for the flow path from the NO supply port 201b to the outlet of the cannula 410 including components to be connected such as the cannula 410, the extension tube 430, and $NO_2$ adsorption unit 420. Specifically, according to the input interface of the concentration estimation unit 301, the residence time of the gas can be changed in accordance with the flow path specification between the NO supply port 201b and the outlet of the cannula 410 including the components to be connected such as the cannula 410, the extension tube 430, and $NO_2$ adsorption unit 420.

It should be noted that in the method of prompting to input or causing the select of the flow path specification of the flow path from the NO supply port 201b to the outlet of the cannula 410 described above, when the input or selection of the flow path specification is not appropriately performed, the accuracy of the concentration estimation is reduced. Thus, when the components such as the cannula 410, the extension tube 430, and $NO_2$ adsorption unit 420 to be connected are connected to the NO supply port 201b, the flow path information such as the cannula 410, the extension tube 430, and $NO_2$ adsorption unit 420 to be arranged may be automatically transmitted to the concentration estimation unit 301 using a sensor such as a contact sensor, a magnetic sensor, an IC tag reader, or a barcode reader, a switch, or a reader as an input interface. Furthermore, by arranging a pressure gauge upstream of the connected cannula 410, the extension tube 430, or the $NO_2$ adsorption unit 420 as an input interface, the types of the components to be connected such as the cannula 410, the extension tube 430, and the $NO_2$ adsorption unit 420 may be automatically determined from the pressure of the flow path during gas flow, i.e., the pressure loss. In other words, the concentration estimation unit 301 may have a table of pressure loss corresponding to the type of cannula and components to be used.

In the nitric oxide administration devices shown in FIGS. 25 and 26, the $NO_2$ adsorption unit 206 may be omitted. Thus, only the $NO_2$ adsorption unit 420 is an $NO_2$ adsorption unit to be maintained, resulting in easy maintenance. In the nitric oxide administration devices shown in FIGS. 25 and 26, the two-way valve 218 and the micro-differential pressure sensor 209 may be omitted. Further, the NO densitometer 208 of the nitric oxide administration device 25 shown in FIG. 25 may be arranged upstream of the $NO_2$ adsorption unit 206, and the $NO/NO_2$ densitometer 219 of the nitric oxide administration device 26 shown in FIG. 26 may be arranged upstream of the $NO_2$ adsorption unit 206.

Based on the estimated NO concentration, the amount of NO generation may be controlled. Furthermore, the method for estimating the concentrations of NO and $NO_2$ at the actual administration point described above may be applied to the relay administration devices described later. Specifically, between the NO supply port 201b and the outlet of the cannula 410, there may be provided an adjustment valve, for example, a two-way valve, configured to adjust the opening and/or the opening time such that the flow rate is increased when the estimated NO concentration is less than a predetermined value and the flow rate is reduced when the estimated NO concentration is larger than a predetermined value. The adjustment valve may allow the supply of NO when the patient inhales and stop the supply of NO when the patient exhales. The opening time of the adjustment valve may be adjusted to be greater when the respiration rate per unit time of the patient is less than a predetermined value, and may be adjusted to be less when the respiration rate per unit time of the patient is greater than a predetermined value. Though the nitric oxide administration devices shown in FIGS. 25 and 26 do not comprise an oxygen generation unit 100, they may comprise an oxygen generation unit 100 like the nitric oxide administration device 1 shown in FIG. 1, etc.

Figure 27:
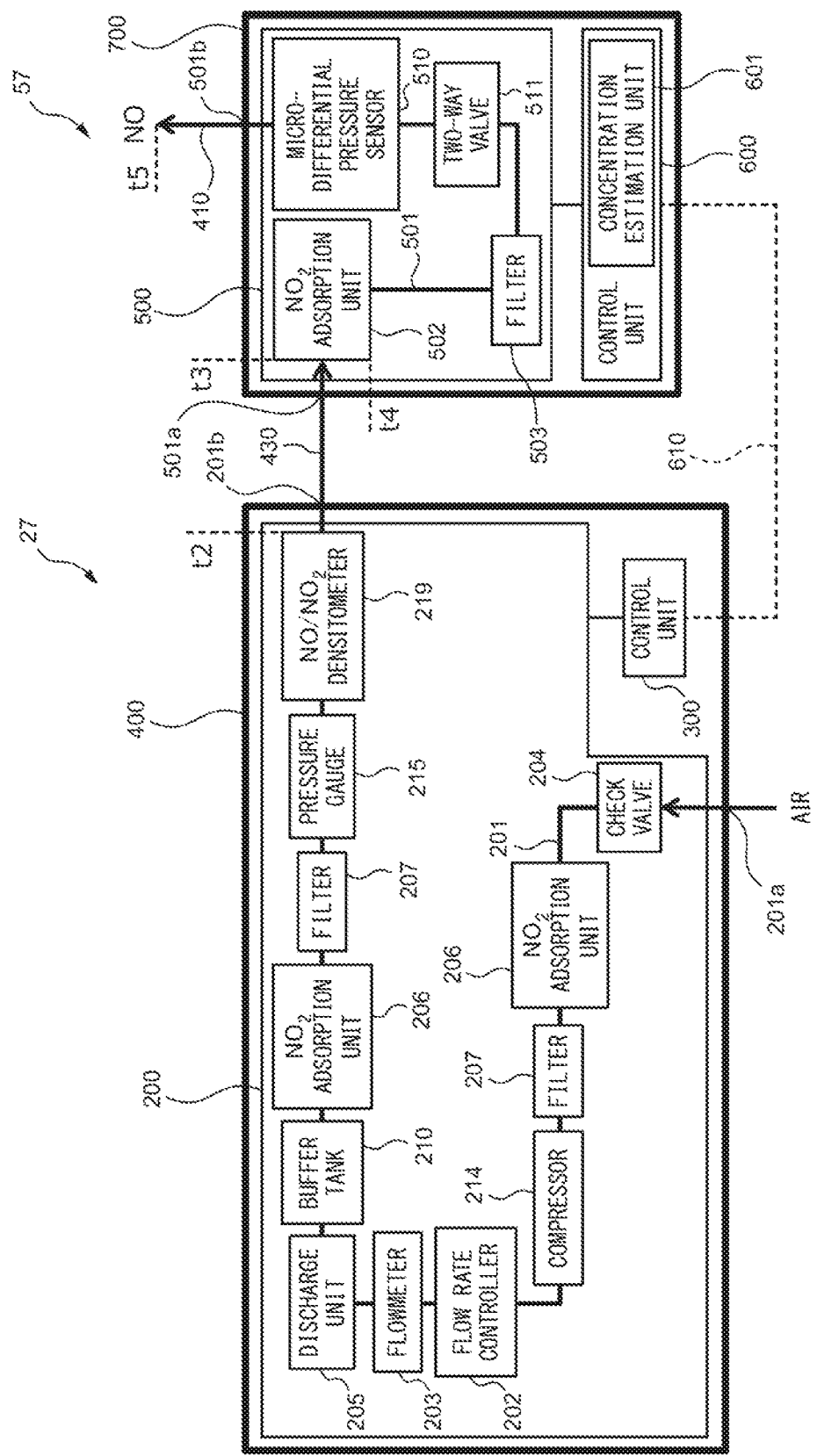
FIG. 27 is a schematic view of yet another nitric oxide administration device and relay administration device.

FIG. 27 is a schematic view of yet another nitric oxide administration device 27 and relay administration device 57. In the nitric oxide administration devices shown in FIGS. 25 and 26, the length of the cannula was also considered for estimating the concentrations of NO and $NO_2$ at the actual administration point. In the nitric oxide administration device 27 and the relay administration device 57 shown in FIG. 27, the concentrations of NO and $NO_2$ at the actual administration point are estimated taking the relay administration device 57 into consideration.

The nitric oxide administration device 27 comprises the second flow path 201 including the intake port 201a and the NO supply port 201b, the NO generation unit 200 arranged in the second flow path 201 and which generates NO from air introduced via the intake port 201a, the control unit 3M), and the housing 400. The NO generation unit 200 and the control unit 300 are housed in the interior of the housing 400. The various operations of the NO generation unit 200 are controlled by the control unit 300.

The NO generation unit 200 comprises, in the second flow path 201, the check valve 204 arranged downstream of the intake port 201a, the $NO_2$ adsorption unit 206 arranged downstream of the check valve 204, the filter 207 arranged downstream of the $NO_2$ adsorption unit 206, the compressor 214 arranged downstream of the filter 207, the flow controller 202 arranged downstream of the compressor 214, the flowmeter 203 arranged downstream of the flow controller 202, the discharge unit 205 arranged downstream of the flowmeter 203, the buffer tank 210 arranged downstream of the discharge unit 205, the $NO_2$ adsorption unit 206 arranged downstream of the buffer tank 210, the filter 207 arranged downstream of the $NO_2$ adsorption unit 206, the pressure gauge 215 arranged downstream of the filter 207, and the $NO/NO_2$ densitometer 219 arranged downstream of the pressure gauge 215.

The upstream side of the relay administration device 57 is connected to the NO supply port 201b via the extension tube 430, and the downstream side of the relay administration device 57 is connected to the upstream end of the cannula 410. The relay administration device 57 comprises a third flow path 501 including the upstream connection end 501a and the downstream connection end 501b, the dosage adjustment unit 500 arranged in the third flow path 501 and which adjusts the dosage of the gas introduced the upstream connection end 501a, the control unit 600, and the housing 700.

The gas adjusted by the dosage adjustment unit 500 is supplied via the downstream side connection end 501b. The various operations of the dosage adjustment unit 500 are controlled by the control unit 60M. The communication path 610 is established between the control unit 300 of the nitric oxide administration device 27 and the control unit 600 of the relay administration device 57 by wire or wirelessly. The relay administration device 57 is connected to a power supply via a power cable (not illustrated). However, the relay administration device 57 may have a battery that can be housed in the interior of the housing 700, and may be a power source. In place of the control unit 600, the nitric oxide administration device 27 and the relay administration device 57 may be electrically connected, and the various operations of the dosage adjustment unit 500 may be controlled by the control unit 300.

The relay administration device 57 comprises the $NO_2$ adsorption part 502 arranged downstream of the upstream connection end 501a in the third flow path 501, the filter 503 arranged downstream of the $NO_2$ adsorption part 502, the two-way valve 512 arranged downstream of the filter 503, and the micro-differential pressure sensor 510 arranged downstream of the two-way valve 512.

The control unit 600 of the relay administration device 57 comprises a concentration estimation unit 601 for estimating the concentrations of NO and $NO_2$ at a predetermined position based on the oxygen concentration, the NO concentration measured by the $NO/NO_2$ densitometer 219 of the nitric oxide administration device 27, which is an NO concentration measurement unit, and the residence time of the gas between the $NO_2$ adsorption unit 502 and the predetermined position.

The $NO/NO_2$ densitometer 219 and the $NO_2$ adsorption unit 502 of FIG. 27 correspond to the $NO/NO_2$ densitometer 219 and the $NO_2$ adsorption unit 420 of FIG. 26, respectively. Thus, the concentration estimation method described with reference to FIGS. 25 and 26 can also be applied as-is to the nitric oxide administration device 27 and the relay administration device 57 shown in FIG. 27.

First, from the flow path specification and the history of the flow rate, the time t2 when the gas Gt5 leaves the $NO/NO_2$ densitometer 219, the time t3 when the gas Gt5 enters the $NO_2$ reservoir 502, the time t4 when the gas Gt5 leaves the $NO_2$ reservoir 502 are calculated. Specifically, in synchronized flow mode, when the current time t=t5, the sum of the most recent dosages up to time t5 is calculated, and the administration number N3 corresponding to the volume between the $NO/NO_2$ densitometer 219 and the outlet of the cannula 410 is calculated. The time t2 when the gas Gt5 leaves the $NO/NO_2$ densitometer 219 is calculated from the administration number N3 and the histories of the administration time and the administration interval time. In the same manner, the times t3 and t4 can be determined. Conversely, in the case of continuous flow mode, the times t2 to t4 can be calculated from the integrated value of the most recent flow rate up to time t and the time when the volume between the outlet of the cannula 410 and each point matches.

At the current time t, in the case in which the gas has not reached the outlet of the cannula 410, i.e., in the case in which the current time t<t5, the time of each upstream point through which the gas has already passed and the time of each point through which the gas will pass can be calculated. Specifically, in the synchronized flow mode, the time of each upstream point through which the gas has passed can be determined based on the histories of the volume up to the upstream point from the dosage up to the current time t, the administration time and the administration interval time, and the current position to the upstream point. Regarding each downstream point through which the gas will pass and the time t5 when the gas leaves the outlet of the cannula 410, for example, the average flow rate can be calculated based on the administration time, the administration interval time, and the dosage within a predetermined time, and can be calculated by dividing the volume from the current position to each point downstream by the average flow rate. Conversely, in continuous flow mode, the time of each upstream point though which the gas has already passed can be calculated, as in the case of the time t=t5, as the time when the integrated value of the current flow rate up to time t, and the volume between the current position and the point match. Regarding each downstream point through which the gas will flow and the time t5 when the gas leaves the outlet of the cannula 410, for example, it can be calculated by calculating the average flow rate within a predetermined time and dividing the volume from the current position to each point of the downstream by the average flow rate. When calculating the time of each upstream point, rather than calculating the time actually lapsed from the sum of the most recent dosage, the average flow rate is calculated based on the administration time, the administration interval time, and the dosage within the predetermined time, and may be calculated by dividing the volume from the current position to each upstream point by the average flow rate.

Next, the NO concentration y3 and $NO_2$ concentration x3 immediately after the gas Gt5 flows into the $NO_2$ adsorption unit 502 are estimated as direct problems from the residence time (t3–t2) between the $NO/NO_2$ densitometer 219 and the $NO_2$ adsorption unit 502, the oxygen concentration (for example, 21%), the NO concentration y2 and $NO_2$ concentration x2 of the gas Gt5 at time t2, and formulas (1) and (2).

The NO concentration y4 and $NO_2$ concentration x4 at time t4 when the gas Gt5 leaves the $NO_2$ adsorption unit 502 are then estimated. As described above, all of the $NO_2$ in the gas Gt5 is adsorbed in the $NO_2$ adsorption unit 502 and an equal amount of NO is reduced. When the time (t4–t3) required for the gas to pass through the interior of the $NO_2$ adsorption unit 502 is large, for example, an $NO_2$ concentration generated during passage from the NO concentration y3 immediately before passage, the oxygen concentration, the time (t4–t3) required for passage, and the equation (2) may be estimated, and some or all of them may be adsorbed. Similarly, NO may be adsorbed in an amount equal to the $NO_2$ generated and adsorbed during passage.

Next, the NO concentration y and $NO_2$ concentration x at the outlet of the cannula 410 are estimated from the NO concentration y4 and $NO_2$ concentration x4 at the time t4 when the gas Gt5 leaves the $NO_2$ adsorption unit 502, the oxygen concentration, the residence time (t–t4) between the $NO_2$ adsorption unit 502 and the outlet of the cannula 410, and formulas (1) and (2) as direct problems.

Depending on the estimated NO concentration y and $NO_2$ concentration x at the outlet of the cannula 410, the discharge parameters of the discharge unit 205 may be changed so as to increase or decrease the NO concentration y, or stoppage may be performed when an abnormality occurs in the value of the NO concentration y or $NO_2$ concentration x. In continuous flow mode, the opening or the opening time of the two-way valve 512 of the relay administration device 57 may be adjusted to adjust the dosage of the gas so as to match the predetermined amount.

Figure 28:
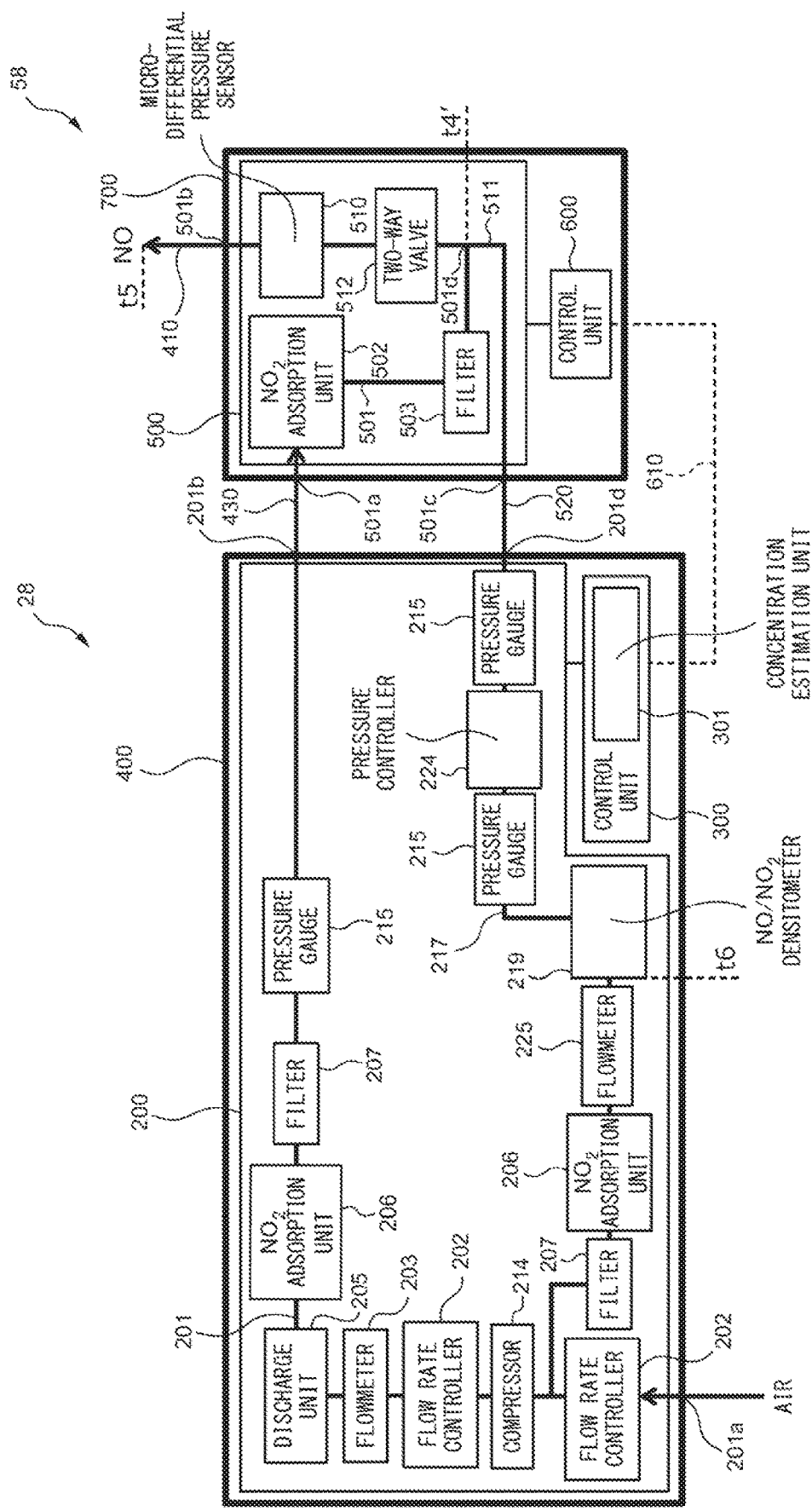
FIG. 28 is a schematic view of yet another nitric oxide administration device and relay administration device.

FIG. 28 is a schematic view of yet another nitric oxide administration device 28 and relay administration device 58. In the nitric oxide administration device 27 shown in FIG. 27, the concentrations of NO and $NO_2$ at the actual administration point were estimated taking the relay administration device 57 into consideration. In the nitric oxide administration device 28 and the relay administration device 58 shown in FIG. 28, the concentrations of NO and $NO_2$ at the actual administration point are estimated further taking the bypass flow path into consideration.

The nitric oxide administration device 28 comprises the second flow path 201 including the intake port 201*a* and the NO supply port 201*b*, the NO generation unit 200 arranged in the second flow path 201 and which generates NO from air introduced via the intake port 201*a*, the control unit 300, and the housing 400. The NO generation unit 200 and the control unit 300 are housed in the interior of the housing 400. The various operations of the NO generation unit 200 are controlled by the control unit 300.

The NO generation unit 200 comprises, in the second flow path 201, the flow controller 202 arranged downstream of the intake port 201*a*, the compressor 214 arranged downstream of the flow controller 202, the Dow controller 202 arranged downstream of the compressor 214, the flowmeter 203 arranged downstream of the flow controller 202, the discharge unit 205 arranged downstream of the flowmeter 203, the $NO_2$ adsorption unit 206 arranged downstream of the discharge unit 205, the filter 207 arranged downstream of the $NO_2$ adsorption unit 206, and the pressure meter 215 arranged downstream of the filter 207.

The upstream side of the relay administration device 58 is connected to the NO supply port 201*b* via the extension tube 430, and the downstream side of the relay administration device 58 is connected to the upstream end of the cannula 410. The relay administration device 58 comprises the third flow path 501 including the upstream connection end 501*a* and the downstream connection end 501*b*, the dosage adjustment unit 500 arranged in the third flow path 501 and which adjusts the dosage of the gas introduced via the upstream connection end 501*a*, the control unit 600, and the housing 700.

The gas adjusted by the dosage adjustment unit 500 is supplied via the downstream side connection end 501*b*. The various operations of the dosage adjustment unit 500 are controlled by the control unit 600. The communication path 610 is established between the control unit 300 of the nitric oxide administration device 28 and the control unit 600 of the relay administration device 58 by wire or wirelessly. The relay administration device 58 is connected to a power supply via a power cable (not illustrated). However, the relay administration device 58 may have a battery that can be housed in the interior of the housing 700, and may be a power source. In place of the control unit 600, the nitric oxide administration device 28 and the relay administration device 58 may be electrically connected, and the various operations of the dosage adjustment unit 500 may be controlled by the control unit 300.

The relay administration device 58 comprises, in the third flow path 501, the $NO_2$ adsorption part 502 arranged downstream of the upstream connection end 501*a*, the filter 503 arranged downstream of the $NO_2$ adsorption part 502, the two-way valve 512 arranged downstream of the filter 503, and the micro-differential pressure sensor 510 arranged downstream of the two-way valve 512. The third flow path 501 between the filter 503 and the two-way valve 512 branches at a branch point 501*d* and extends to a bypass upstream side connection end 501*c*. The bypass upstream connection end 501*c* of the relay administration device 58 is connected to the bypass downstream side connection end 201*d* of the nitric oxide administration device 28 via a bypass tube 520.

In the bypass flow path 217 extending from the bypass downstream side connection end 201*d*, the pressure gauge 215 is arranged downstream of the bypass downstream connection end 201*d*, a pressure controller 224 is arranged downstream of the pressure gauge 215, the pressure gauge 215 is arranged downstream of the pressure controller 224, the $NO/NO_2$ densitometer 219 is arranged downstream of the pressure gauge 215, the flowmeter 225 is arranged downstream of the $NO/NO_2$ densitometer 219, the $NO_2$ adsorption unit 206 is arranged downstream of the flowmeter 225, and the filter 207 is arranged downstream of the $NO_2$ adsorption unit 206. Bypass flow path 217, downstream of the filter 207, communicates with the second flow path 201 between the flow controller 202 and the compressor 214.

Since the relay administration device 58 comprises one two-way valve 512 in the branched third flow path 501, the gas of the relay administration device 58 can always be refluxed to the nitric oxide administration device 28 regardless of the opening and closing of the two-way valve 512.

The control unit 300 of the nitric oxide administration device 28 comprises the concentration estimation unit 301 for estimating the concentrations of NO and $NO_2$ at a predetermined position based on the oxygen concentration, the concentrations of NO and $NO_2$ measured by the $NO/NO_2$ densitometer 219, which is an NO concentration measurement unit, and the residence time of the gas between the $NO_2$ adsorption unit 502 of the relay administration device 58 and the predetermined position.

The $NO_2$ adsorption unit 502 of FIG. 28 corresponds to the $NO_2$ adsorption unit 420 of FIG. 26. Conversely, the NO % $NO_2$ densitometer 219 of FIG. 28 differs from the $NO/NO_2$ densitometer 219 of FIG. 26 in that it is arranged in the bypass flow path 217. However, though the estimation pathways are different, the concentration estimation method described with reference to FIGS. 25 and 26 can also be applied to the nitric oxide administration device 28 and the relay administration device 58 shown in FIG. 28.

First, from the flow path specification and the history of the flow rate, a time t4' when the gas Gt5 passes through the branch point 501d and time 6 when the gas Gt5 leaves the NO/NO$_2$ densitometer 219 via the bypass flow path 217 are calculated. Specifically, in synchronized flow mode, when the current time t=t5, the sum of the most recent dosage up to time t5 is calculated, and an administration number N4 corresponding to the volume between the branch point 501d and the outlet of the cannula 410 is calculated. The time t4' when the gas Gt5 passes through the branch point 501d is calculated from the administration number N4, and the histories of the administration time and the administration interval time.

At the current time t, in the case in which the gas has not reached the outlet of the cannula 410, i.e., in the case in which the current time t<t5, the time of each upstream point through which the gas has already passed and the time of each point through which the gas will pass can be calculated. Specifically, in the synchronized flow mode, the time of each upstream point through which the gas has already passed can be determined, as in the case of the time t=t5, based on the histories of the volume up to the each upstream point from the dosage up to the current time t, the administration time and the administration interval time, and the current position to the upstream point. Regarding each downstream point through which the gas will pass and the time t5 when the gas leaves the outlet of the cannula 410, for example, the average flow rate can be calculated based on the administration time, the administration interval time, and the dosage within a predetermined time, and can be calculated by dividing the volume from the current position to each point downstream by the average flow rate. Conversely, in continuous flow mode, the time of each upstream point though which the gas has already passed can be calculated, as in the case of the time t=t5, as the time when the integrated value of the current flow rate up to time t, and the volume between the current position and the each point match. Regarding each downstream point through which the gas will flow and the time t5 when the gas leaves the outlet of the cannula 410, for example, it can be calculated by calculating the average flow rate within a predetermined time and dividing the volume from the current position to each point of the downstream by the average flow rate. When calculating the time of each upstream point, rather than calculating the time actually lapsed from the sum of the most recent dosage, the average flow rate is calculated based on the administration time, the administration interval time, and the dosage within the predetermined time, and may be calculated by dividing the volume from the current position to each upstream point by the average flow rate.

Then, the time t6 when the gas Gt4' is at branch point 501d at time t4' and flowing toward the bypass flow path 217 has passed through the NO/NO$_2$ densitometer 219 is obtained. Specifically, the time at which an integrated value of the flow rate up to time t4' of the flowmeter 255 arranged in the bypass flow path 217 and the volume between the branch point 501d and the NO/NO$_2$ densitometer 219 match is defined as t6. Note that the flow rate of the bypass flow path 217 may be estimated by subtracting the dosage from the flow rate of the flowmeter 203.

Next, the NO concentration y 4' and NO$_2$ concentration x4' when the gas Gt4' passes through the branch point 501d are estimated as inverse problems from the residence time (t6−t4') between the NO/NO$_2$ concentration meter 219 and the branch point 501d, the oxygen concentration (for example, 21%), the NO concentration y6 and the NO$_2$ concentration x6 of the gas Gt4' at the time t6, and formulas (1) and (2).

The NO concentration y and NO$_2$ concentration x at the outlet of the cannula 410 are estimated as direct problems from the NO concentration y4' and the NO$_2$ concentration x4' at time t4' when the gas Gt5 leaves the branch point Sold, the oxygen concentration, the residence time (t−t4') between the branch point 501d and the outlet of the cannula 410, and formulas (1) and (2).

When t5≥time t6, the NO concentration y and NO$_2$ concentration x at the outlet of the cannula 410 can be estimated in nearly real time. Thus, the flow path volume and the reflux flow rate may be controlled so that the residence time of the gas Gt5 from the branch point 501d to the NO/NO$_2$ densitometer 219 becomes shorter than the residence time of the gas Gt5 from the branch point 501d to the outlet of the cannula 410.

Conversely, when time t5<time t6, the NO concentration y and NO$_2$ concentration x at the outlet of the cannula 410 cannot be estimated until time t=t6. At this time, for example, when the concentrations of NO and NO$_2$ measured by the NO/NO$_2$ densitometer 219 are nearly constant, the average flow rate within a predetermined time of the flowmeter 255 is calculated, and the time t6 is estimated by dividing the volume from the current position to the NO/NO$_2$ densitometer 219 by the average flow rate. The NO concentration y and NO$_2$ concentration x at the outlet of the cannula 410 at time t5 may then be estimated by assuming that the concentrations of NO and NO$_2$ measured by the NO/NO$_2$ densitometer 219 at time t5 are the concentrations of NO and NO$_2$ measured by the densitometer 219 at time t6. Conversely, when the concentrations of NO and NO$_2$ measured by the NO/NO$_2$ densitometer 219 fluctuate, the concentrations of NO and NO$_2$ measured by the NO/NO$_2$ densitometer 219 at time t6 may be estimated by obtaining an approximate expression for the concentration fluctuations within a predetermined time and integrating the time up to the estimated time t6.

Regarding dosage, the fluctuations in the dosage when the opening time of the two-way valve 512 changes while the third flow path 501 is maintained at a predetermined flow rate or pressure is measured in advance. By designing the third flow path 501 to maintain a predetermined flow rate or pressure, the dosage can be estimated from the time of opening of the two-way valve 512. Furthermore, the dosage may be determined by subtracting the total flow rate of the gas that has passed through the flowmeter 225 within the corresponding predetermined time from the total flow rate of the gas that has passed through the flowmeter 203 within the predetermined time. The dosage may be measured directly by installing a flowmeter between the branch point 501d and the outlet of the cannula 410.

Regarding the flow rate in the bypass flow path 217, instead of the flowmeter 225 arranged in the bypass flow path 217, it may be estimated by subtracting the dosage from the flow history of the flowmeter 203 arranged in the second flow path 201.

Figure 29:
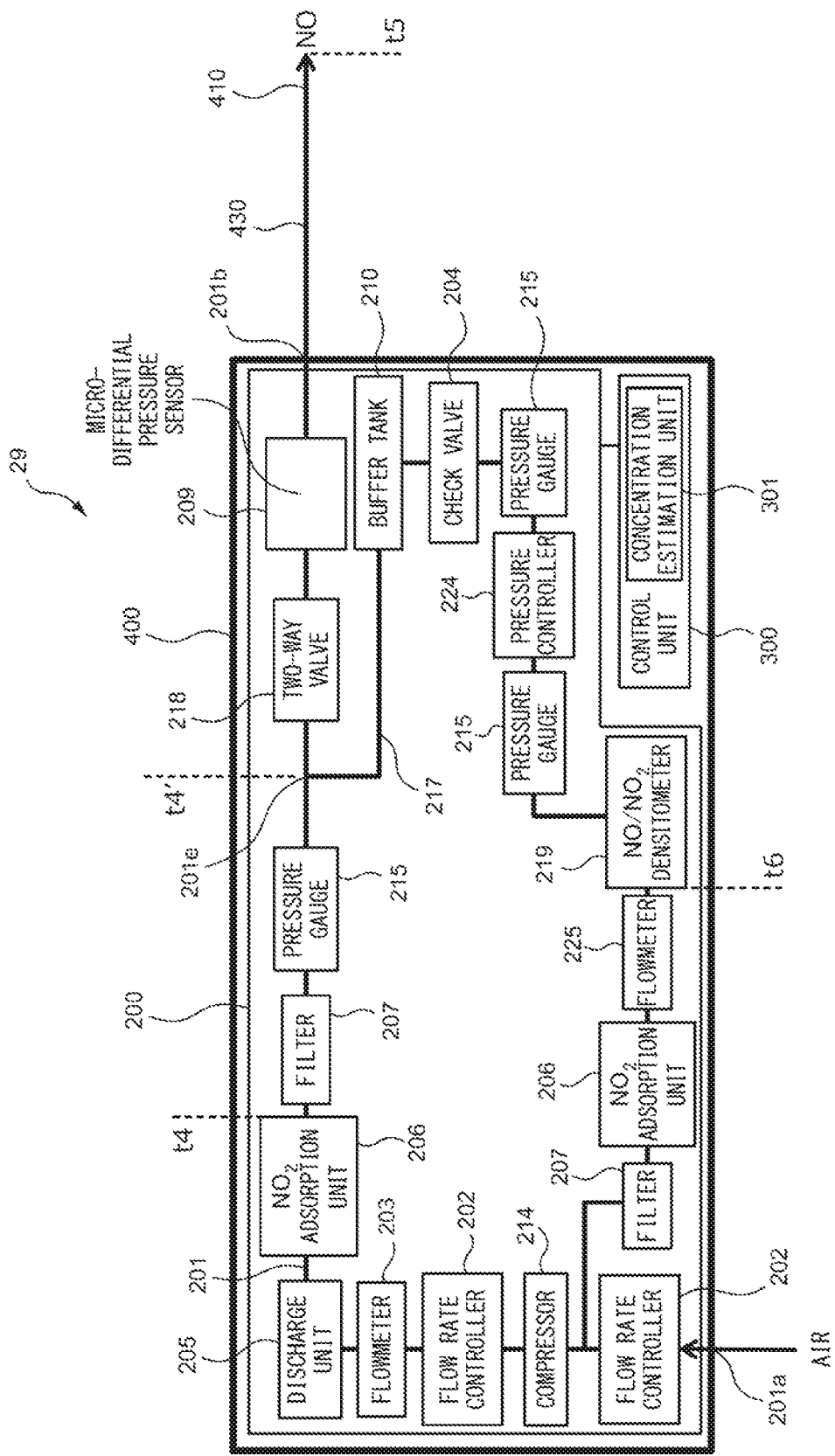
FIG. 29 is a schematic view of yet another nitric oxide administration device and relay administration device.

FIG. 29 is a schematic view of yet another nitric oxide administration device 29. In the nitric oxide administration device 29, the concentrations of NO and NO$_2$ at the actual administration point are estimated taking the bypass flow path 217 into consideration.

The nitric oxide administration device 29 comprises the second flow path 201 including the intake port 201a and the NO supply port 201b, the NO generation unit 200 arranged in the second flow path 201 and which generates NO from air introduced via the intake port 201a, the control unit 300, and the housing 400. The NO generation unit 200 and the control unit 300 are housed in the interior of the housing 400. The various operations of the NO generation unit 200 are controlled by the control unit 300.

The NO generation unit 200 comprises, in the second flow path 201, the flow controller 202 arranged downstream of the intake port 201a, the compressor 214 arranged downstream of the flow controller 202, the flow controller 202 arranged downstream of the compressor 214, the flowmeter 203 arranged downstream of the flow controller 202, the a discharge unit 205 arranged downstream of the flowmeter 203, the $NO_2$ adsorption unit 206 arranged downstream of the discharge unit 205, the filter 207 arranged downstream of the $NO_2$ adsorption unit 206, the pressure gauge 215 arranged downstream of the filter 207, the two-way valve 218 arranged downstream of the pressure gauge 215, and the differential pressure sensor 209 arranged downstream of the two-way valve 218.

From the second flow path 201 between the pressure gauge 215 and the two-way valve 218, the bypass flow path 217 branches at a branch point 201e and is connected to the buffer tank 210. In the bypass flow path 217, the check valve 204 is arranged downstream of the buffer tank 210, the pressure gauge 215 is arranged downstream of the check valve 204, the pressure controller 224 is arranged downstream of the pressure gauge 215, the pressure gauge 215 is arranged downstream of the pressure controller 224, the $NO/NO_2$ densitometer 219 is arranged downstream of the pressure gauge 215, the flowmeter 225 is arranged downstream of the $NO/NO_2$ densitometer 219, the $NO_2$ adsorption unit 206 is arranged downstream of the flowmeter 225, and the filter 207 is arranged downstream of the $NO_2$ adsorption unit 206. The bypass flow path 217, downstream of the filter 207, communicates with the second flow path 201 between the flow controller 202 and the compressor 214.

Since the nitric oxide administration device 29 comprises the two-way valve 512, the second flow path 201 and the bypass flow path 217 always communicate with each other regardless of the opening and closing of the two-way valve 512, whereby the gas is refluxed in the nitric oxide administration device 29.

The control unit 300 of the nitric oxide administration device 29 has the concentration estimation unit 301 for estimating the concentrations of NO and $NO_2$ at a predetermined position based on the oxygen concentration, the concentrations of NO and $NO_2$ measured by the $NO/NO_2$ densitometer 219, which is an NO concentration measurement unit, and the residence time of the gas between the $NO_2$ adsorption unit 206 and the predetermined position.

Though the nitric oxide administration device 29 shown in FIG. 29 differs from the nitric oxide administration device 28 shown in FIG. 28 in that it does not comprise a relay administration device, it is similar thereto in that it is necessary take the bypass flow path into consideration. Thus, since the estimation method of the concentration described with reference to FIG. 28 can also be applied to the nitric oxide administration device 29 shown in FIG. 29, description thereof has been omitted. Specifically, the time when the gas Gt5 passes through the branch point 201e may be set to time t4' in the same manner as in the method for estimating the concentration described with reference to FIG. 28.

According to the estimation method described in FIGS. 28 and 29, in particular, the impact on the NO concentration measurement unit due to pressure fluctuations in the flow path in the case of supplying an intermittent flow such as a synchronized flow mode can be reduced. Specifically, in FIGS. 28 and 29, the NO concentration measurement unit is arranged in the flow path that refluxes from the downstream side of a first $NO_2$ removal unit to the upstream side of the first $NO_2$ removal unit. Furthermore, since the gas is always refluxed by the two-way valve, pressure fluctuations are reduced as a result. In particular, pressure fluctuations are reduced by the bypass flow path 217 or bypass tube 520 serving as a buffer tank. Further, due to the bypass flow path 217 or the bypass tube 520 serving as a buffer tank, decreases in pressure at the time of administration are small, whereby the administration time can be shortened. When supplying intermittent flow, while stopping the supply of NO, the flow path of the upstream side of the two-way valve is maintained at a high pressure. In the nitric oxide administration devices and the relay administration devices shown in FIGS. 28 and 29, since the NO concentration measurement unit is arranged in the flow path from the downstream of the branch point 201e to the upstream of the compressor 214, it is possible to reduce the pressure load on the NO concentration measurement unit while the supply of NO is stopped. Furthermore, by arranging the pressure controller 224 in the flow path upstream of the NO concentration measurement unit, it is possible to further reduce the pressure load.

In the nitric oxide administration devices described above, in particular, various structures such as a pump, a pressure reducing valve, a buffer tank, a pressure gauge, a flowmeter, a leak valve, an adjustment valve, a shutoff valve, and combinations thereof have been exemplified, but these structures and combinations thereof may be optionally added or omitted in order to achieve the effects and objects described above.

The nitric oxide administration devices described above comprise an abnormality detection unit, and when an abnormality is detected during the supply of NO or concentrated oxygen, an alarm may be emitted to the user to alert to the abnormality. Furthermore, when there is an abnormality in the supply amount or concentration of either NO or concentrated oxygen, the other supply amount or concentration may be adjusted.

REFERENCE SIGNS LIST 1 nitric oxide administration device
100 oxygen generation unit
101 first flow path
102 compressor
103 pressure valve
104 pressure-reducing valve
105 suction tube
106 pressure-equalizing valve
107 check valve
108 buffer tank
109 flow rate controller
110 $O_2$ densitometer
111 flowmeter
200 NO generation unit
201 second flow path
202 flow rate controller
203 flowmeter
204 check valve
205 discharge unit
206 $NO_2$ adsorption unit
207 filter
208 NO densitometer

The invention claimed is:

1. A nitric oxide administration device, comprising:
a first flow path including a first intake port and an oxygen supply port,
an oxygen generation unit which is arranged in the first flow path and which generates concentrated oxygen from air introduced via the first intake port, the generated concentrated oxygen being supplied via the oxygen supply port,
a second flow path which is branched from the first flow path and which includes an NO supply port, and
an NO generation unit which is arranged in the second flow path and which generates NO from gas distributed from the first flow path, the generated NO being supplied via the NO supply port, the oxygen supply port being isolated from the NO supply port.

2. The nitric oxide administration device according to claim 1, wherein the oxygen generation unit and the NO generation unit are housed in an interior of the same housing.

3. The nitric oxide administration device according to claim 1, further comprising a compressor arranged in the first flow path.

4. The nitric oxide administration device according to claim 3, wherein the distributed gas is air compressed by the compressor.

5. The nitric oxide administration device according to claim 1, wherein the distributed gas is hypoxic gas generated along with the generation of concentrated oxygen in the oxygen generation unit.

6. The nitric oxide administration device according to claim 1, wherein the distributed gas is concentrated oxygen generated by the oxygen generation unit.

7. The nitric oxide administration device according to claim 1, wherein in the second flow path, hypoxic gas generated along with the generation of concentrated oxygen in the oxygen generation unit is mixed with generated NO.

8. The nitric oxide administration device according to claim 7, wherein a flow path switching valve for switching opening and closing of the flow path of the hypoxic gas from the first flow path to the second flow path is arranged.

9. The nitric oxide administration device according to claim 1, wherein an NO or $NO_2$ removal agent is arranged upstream of the first flow path or in the vicinity of the first intake port.

10. The nitric oxide administration device according to claim 1, further comprising a cannula which is connected to the oxygen supply port and the NO supply port and which has an independent flow path.

11. The nitric oxide administration device according to claim 1, wherein the NO generation unit has a second intake port.

* * * * *